US009024719B1

(12) United States Patent
Saunders

(10) Patent No.: US 9,024,719 B1
(45) Date of Patent: May 5, 2015

(54) RF TRANSACTION SYSTEM AND METHOD FOR STORING USER PERSONAL DATA

(75) Inventor: Peter D Saunders, Salt Lake City, UT (US)

(73) Assignee: Xatra Fund MX, LLC, Wilmington, DE (US)

( * ) Notice: Subject to any disclaimer, the term of this patent is extended or adjusted under 35 U.S.C. 154(b) by 2192 days.

(21) Appl. No.: 10/711,964

(22) Filed: Oct. 15, 2004

Related U.S. Application Data

(63) Continuation-in-part of application No. 10/340,352, filed on Jan. 10, 2003, now Pat. No. 7,889,052, which is a continuation-in-part of application No. 10/192,488, filed on Jul. 9, 2002, now Pat. No.

(Continued)

(51) Int. Cl.
*G05B 19/00* (2006.01)
*G06F 19/00* (2011.01)

(52) U.S. Cl.
CPC ................... *G06F 19/322* (2013.01)

(58) Field of Classification Search
CPC .............. G07C 9/00309; G07C 2009/00793; G07C 2209/63; G07C 9/00111; B60R 25/24; G06K 7/0008; G06K 19/0723; G06K 7/10039; G06K 2017/0045; G08B 13/2462
USPC .............. 340/5.61, 10.3; 235/381, 382, 382.5
See application file for complete search history.

(56) References Cited

U.S. PATENT DOCUMENTS

| D61,466 S | 9/1922 | Foltz |
| 2,767,756 A | 10/1956 | Niles |
| 3,376,661 A | 4/1968 | Hulett |
| 3,446,260 A | 5/1969 | Osher |
| 3,536,894 A | 10/1970 | Travioli |
| 3,573,731 A | 4/1971 | Schwend |

(Continued)

FOREIGN PATENT DOCUMENTS

| CH | 689070 | 8/1998 |
| CH | 689680 | 8/1999 |

(Continued)

OTHER PUBLICATIONS

"What's New: Timex Watch Features Speedpass System", http://www.speedpass.com/news/article.jsp?id=51 (1 page).

(Continued)

*Primary Examiner* — Brian Zimmerman
*Assistant Examiner* — Omer S Khan
(74) *Attorney, Agent, or Firm* — Brundidge & Stanger, P.C.

(57) ABSTRACT

A system and method for a RF transaction device for storing user personal data is disclosed. The invention includes a system and method for facilitating a healthcare transaction using a transponder system configured to store different healthcare information in different storage areas on a database. The invention includes providing account information in ISO/IEC 7816 magnetic stripe Track 1/Track 2 format. The invention also includes an RFID reader for transmitting account and database information. In one embodiment the invention provides an RFID reader as a free standing or a computer implemented device. In another embodiment, biometric security measures are used in conjunction with the transponder system. In another embodiment, the transponder system communicates with one or more third-party healthcare providers to facilitate the transfer of healthcare and personal information.

16 Claims, 24 Drawing Sheets

Related U.S. Application Data 7,239,226, said application No. 10/340,352 is a continuation-in-part of application No. 10/318,432, filed on Dec. 13, 2002, and a continuation-in-part of application No. 10/318,480, filed on Dec. 13, 2002, now Pat. No. 7,249,112.

(60) Provisional application No. 60/512,297, filed on Oct. 17, 2003, provisional application No. 60/304,216, filed on Jul. 10, 2001, provisional application No. 60/396,577, filed on Jul. 16, 2002.

(56) References Cited

U.S. PATENT DOCUMENTS

| | | | |
|---|---|---|---|
| 3,725,647 | A | 4/1973 | Retzky |
| 3,763,356 | A | 10/1973 | Berler |
| 3,829,662 | A | 8/1974 | Furahashi |
| 3,838,252 | A | 9/1974 | Hynes et al. |
| 3,873,813 | A | 3/1975 | Lahr et al. |
| 3,894,756 | A | 7/1975 | Ward |
| 3,914,762 | A | 10/1975 | Klensch |
| 3,929,177 | A | 12/1975 | Reis |
| 3,955,295 | A | 5/1976 | Mayer |
| 4,044,231 | A | 8/1977 | Beck et al. |
| 4,048,737 | A | 9/1977 | McDermott |
| 4,056,139 | A | 11/1977 | Murt |
| 4,058,839 | A | 11/1977 | Darjany |
| 4,066,873 | A | 1/1978 | Schatz |
| 4,119,361 | A | 10/1978 | Greenaway |
| 4,202,491 | A | 5/1980 | Suzuki |
| 4,206,965 | A | 6/1980 | McGrew |
| 4,222,516 | A | 9/1980 | Badet et al. |
| 4,277,863 | A | 7/1981 | Faneuf |
| 4,303,904 | A | 12/1981 | Chasek |
| 4,318,554 | A | 3/1982 | Anderson et al. |
| 4,356,646 | A | 11/1982 | Johnson, Jr. |
| 4,361,757 | A | 11/1982 | Ehrat |
| D270,303 | S | 8/1983 | Zautner |
| D270,546 | S | 9/1983 | Malmberg |
| 4,421,380 | A | 12/1983 | McGrew |
| 4,436,991 | A | 3/1984 | Albert et al. |
| 4,443,027 | A | 4/1984 | McNeely et al. |
| 4,450,535 | A | 5/1984 | dePommery et al. |
| 4,453,074 | A | 6/1984 | Weinstein |
| 4,475,308 | A | 10/1984 | Heise et al. |
| 4,504,084 | A | 3/1985 | Jauch |
| 4,507,652 | A | 3/1985 | Vogt et al. |
| D280,214 | S | 8/1985 | Opel |
| 4,538,059 | A | 8/1985 | Rudland |
| 4,547,002 | A | 10/1985 | Colgate, Jr. |
| 4,558,211 | A | 12/1985 | Berstein |
| 4,563,024 | A | 1/1986 | Blyth |
| 4,581,523 | A | 4/1986 | Okuno |
| 4,582,985 | A | 4/1986 | Lofberg |
| 4,583,766 | A | 4/1986 | Wessel |
| 4,589,686 | A | 5/1986 | McGrew |
| 4,593,936 | A | 6/1986 | Opel |
| 4,597,814 | A | 7/1986 | Colgate, Jr. |
| 4,639,765 | A | 1/1987 | dHont |
| 4,641,017 | A | 2/1987 | Lopata |
| 4,643,452 | A | 2/1987 | Chang |
| 4,656,463 | A | 4/1987 | Anders et al. |
| 4,663,518 | A | 5/1987 | Borror et al. |
| 4,672,021 | A | 6/1987 | Blumel et al. |
| 4,684,795 | A | 8/1987 | Colgate, Jr. |
| 4,692,394 | A | 9/1987 | Drexler |
| 4,694,148 | A | 9/1987 | Diekemper et al. |
| 4,697,073 | A | 9/1987 | Hara |
| 4,697,363 | A | 10/1987 | Gamm |
| 4,700,055 | A | 10/1987 | Kashkashian, Jr. |
| 4,711,690 | A | 12/1987 | Haghiri-Tehrani |
| 4,717,221 | A | 1/1988 | McGrew |
| 4,725,719 | A | 2/1988 | Oncken et al. |
| 4,736,094 | A | 4/1988 | Yoshida |
| 4,739,328 | A | 4/1988 | Koelle et al. |
| 4,744,497 | A | 5/1988 | O'Neal |
| 4,747,147 | A | 5/1988 | Sparrow |
| 4,768,811 | A | 9/1988 | Oshikoshi et al. |
| 4,779,898 | A | 10/1988 | Berning et al. |
| 4,794,142 | A | 12/1988 | Alberts et al. |
| 4,795,894 | A | 1/1989 | Sugimoto et al. |
| 4,801,790 | A | 1/1989 | Solo |
| 4,816,653 | A | 3/1989 | Anderl et al. |
| 4,829,690 | A | 5/1989 | Andros |
| 4,837,422 | A | 6/1989 | Dethloff et al. |
| 4,839,504 | A | 6/1989 | Nakano |
| 4,841,570 | A | 6/1989 | Cooper |
| 4,849,617 | A | 7/1989 | Ueda |
| 4,852,911 | A | 8/1989 | Hoppe |
| 4,853,525 | A | 8/1989 | Vogt et al. |
| 4,863,819 | A | 9/1989 | Drexler et al. |
| 4,868,849 | A | 9/1989 | Tamaoki |
| 4,884,507 | A | 12/1989 | Levy |
| 4,889,366 | A | 12/1989 | Fabbiani |
| 4,897,533 | A | 1/1990 | Lyszczarz |
| 4,897,947 | A | 2/1990 | Kass-Pious |
| 4,910,521 | A | 3/1990 | Mellon |
| 4,917,292 | A | 4/1990 | Drexler |
| 4,918,432 | A | 4/1990 | Pauley et al. |
| D307,979 | S | 5/1990 | Purvis |
| 4,937,963 | A | 7/1990 | Barnes |
| D310,386 | S | 9/1990 | Michels et al. |
| 4,961,142 | A | 10/1990 | Elliott et al. |
| 4,984,270 | A | 1/1991 | LaBounty |
| 4,993,068 | A | 2/1991 | Piosenka et al. |
| 4,998,753 | A | 3/1991 | Wichael |
| 5,004,899 | A | 4/1991 | Ueda |
| 5,010,243 | A | 4/1991 | Fukushima et al. |
| 5,015,830 | A | 5/1991 | Masuzawa et al. |
| 5,016,274 | A | 5/1991 | Micali et al. |
| 5,023,782 | A | 6/1991 | Lutz et al. |
| 5,023,908 | A | 6/1991 | Weiss |
| 5,025,372 | A | 6/1991 | Burton et al. |
| 5,052,328 | A | 10/1991 | Eppenbach |
| 5,053,774 | A | 10/1991 | Schuermann et al. |
| 5,068,894 | A | 11/1991 | Hoppe |
| 5,096,228 | A | 3/1992 | Rinderknecht |
| 5,099,226 | A | 3/1992 | Andrews |
| 5,101,200 | A | 3/1992 | Swett |
| 5,106,125 | A | 4/1992 | Antes |
| 5,111,033 | A | 5/1992 | Fujita et al. |
| 5,125,356 | A | 6/1992 | Galante |
| 5,142,383 | A | 8/1992 | Mallik |
| 5,171,039 | A | 12/1992 | Dusek |
| 5,175,416 | A | 12/1992 | Mansvelt et al. |
| 5,180,902 | A | 1/1993 | Schick et al. |
| 5,192,947 | A | 3/1993 | Neustein |
| 5,193,114 | A | 3/1993 | Moseley |
| 5,197,140 | A | 3/1993 | Balmer |
| 5,198,647 | A | 3/1993 | Mizuta |
| 5,202,826 | A | 4/1993 | McCarthy |
| 5,206,488 | A | 4/1993 | Teicher |
| 5,208,110 | A | 5/1993 | Smith et al. |
| 5,212,777 | A | 5/1993 | Gove et al. |
| 5,217,844 | A | 6/1993 | Fukushima et al. |
| 5,221,838 | A | 6/1993 | Gutman et al. |
| 5,222,282 | A | 6/1993 | Sukonnik et al. |
| 5,226,989 | A | 7/1993 | Sukonnik |
| 5,234,624 | A | 8/1993 | Bauer et al. |
| 5,239,654 | A | 8/1993 | IngSimmons et al. |
| 5,245,329 | A | 9/1993 | Gokcebay |
| 5,247,304 | A | 9/1993 | dHont |
| 5,251,937 | A | 10/1993 | Ojster |
| 5,256,473 | A | 10/1993 | Kotani et al. |
| 5,257,656 | A | 11/1993 | McLeroy |
| 5,259,649 | A | 11/1993 | Shomron |
| 5,272,326 | A | 12/1993 | Fujita et al. |
| 5,274,392 | A | 12/1993 | dHont et al. |
| 5,276,311 | A | 1/1994 | Hennige |
| 5,279,019 | A | 1/1994 | Knickle |
| 5,285,100 | A | 2/1994 | Byatt |
| 5,288,978 | A | 2/1994 | Iijima |
| 5,300,764 | A | 4/1994 | Hoshino et al. |

(56) References Cited

U.S. PATENT DOCUMENTS

| | | |
|---|---|---|
| 5,304,789 A | 4/1994 | Lob et al. |
| 5,305,002 A | 4/1994 | Holodak et al. |
| 5,308,121 A | 5/1994 | Gunn |
| 5,311,679 A | 5/1994 | Birch, Sr. |
| 5,321,751 A | 6/1994 | Ray et al. |
| 5,326,964 A | 7/1994 | Risser |
| 5,329,617 A | 7/1994 | Asal |
| 5,331,138 A | 7/1994 | Saroya |
| 5,339,447 A | 8/1994 | Balmer |
| 5,349,357 A | 9/1994 | Schurmann et al. |
| 5,351,052 A | 9/1994 | D'Hont et al. |
| 5,351,142 A | 9/1994 | Cueli |
| 5,355,411 A | 10/1994 | MacDonald |
| 5,359,522 A | 10/1994 | Ryan |
| 5,365,551 A | 11/1994 | Snodgrass et al. |
| 5,371,896 A | 12/1994 | Gove et al. |
| 5,373,303 A | 12/1994 | dHont |
| 5,383,687 A | 1/1995 | Suess et al. |
| 5,397,881 A | 3/1995 | Mannik |
| 5,407,893 A | 4/1995 | Koshizuka et al. |
| 5,408,243 A | 4/1995 | dHont |
| 5,410,142 A | 4/1995 | Tsuboi et al. |
| 5,410,649 A | 4/1995 | Gove |
| 5,412,192 A | 5/1995 | Hoss |
| 5,428,363 A | 6/1995 | dHont |
| 5,438,184 A | 8/1995 | Roberts et al. |
| 5,453,747 A | 9/1995 | D'Hont et al. |
| 5,461,217 A | 10/1995 | Claus |
| 5,461,219 A | 10/1995 | Cronvall |
| 5,471,592 A | 11/1995 | Gove et al. |
| 5,477,038 A | 12/1995 | Levine et al. |
| 5,477,040 A | 12/1995 | Lalonde |
| 5,478,629 A | 12/1995 | Norman |
| 5,479,494 A | 12/1995 | Clitherow |
| 5,479,530 A | 12/1995 | Nair et al. |
| 5,485,510 A | 1/1996 | Colbert |
| 5,488,376 A | 1/1996 | Hurta et al. |
| 5,489,411 A | 2/1996 | Jha et al. |
| 5,489,908 A | 2/1996 | Orthmann et al. |
| 5,490,079 A | 2/1996 | Sharpe et al. |
| 5,491,483 A | 2/1996 | dHont |
| 5,491,484 A | 2/1996 | Schuermann |
| 5,491,715 A | 2/1996 | Flaxl |
| 5,493,312 A | 2/1996 | Knebelkamp |
| 5,497,121 A | 3/1996 | dHont |
| 5,500,513 A | 3/1996 | Langhans et al. |
| 5,500,651 A | 3/1996 | Schuermann |
| 5,503,434 A | 4/1996 | Gunn |
| 5,504,808 A | 4/1996 | Hamrick, Jr. |
| 5,506,395 A | 4/1996 | Eppley |
| 5,513,272 A | 4/1996 | Bogosian, Jr. |
| 5,513,525 A | 5/1996 | Schurmann |
| 5,514,860 A | 5/1996 | Berson |
| 5,516,153 A | 5/1996 | Kaule |
| 5,518,810 A | 5/1996 | Nishihara et al. |
| 5,519,381 A | 5/1996 | Marsh et al. |
| 5,520,230 A | 5/1996 | Sumner, III |
| 5,521,966 A | 5/1996 | Friedes et al. |
| 5,522,083 A | 5/1996 | Gove et al. |
| 5,525,992 A | 6/1996 | Froschermeier |
| 5,525,994 A | 6/1996 | Hurta et al. |
| 5,528,222 A | 6/1996 | Moskowitz et al. |
| 5,530,232 A | 6/1996 | Taylor |
| 5,533,656 A | 7/1996 | Bonaldi |
| 5,534,857 A | 7/1996 | Laing et al. |
| 5,537,314 A | 7/1996 | Kanter |
| 5,539,825 A | 7/1996 | Akiyama |
| 5,541,582 A | 7/1996 | Wagner et al. |
| 5,541,604 A | 7/1996 | Meier |
| 5,543,798 A | 8/1996 | Schuermann |
| 5,544,246 A * | 8/1996 | Mandelbaum et al. ......... 705/65 |
| 5,548,291 A | 8/1996 | Meier et al. |
| 5,550,536 A | 8/1996 | Flaxl |
| 5,550,548 A | 8/1996 | Schuermann |
| 5,552,789 A | 9/1996 | Schuermann |
| 5,555,877 A | 9/1996 | Lockwood et al. |
| 5,557,279 A | 9/1996 | dHont |
| 5,557,516 A | 9/1996 | Hogan |
| 5,559,504 A | 9/1996 | Itsumi et al. |
| 5,559,887 A | 9/1996 | Davis et al. |
| 5,561,430 A | 10/1996 | Knebelkamp |
| 5,563,582 A | 10/1996 | dHont |
| 5,569,187 A | 10/1996 | Kaiser |
| 5,569,897 A | 10/1996 | Masuda |
| 5,572,226 A | 11/1996 | Tuttle |
| 5,572,815 A | 11/1996 | Kovner |
| 5,575,094 A | 11/1996 | Leake et al. |
| 5,577,109 A | 11/1996 | Stimson et al. |
| 5,577,120 A | 11/1996 | Penzias |
| 5,577,121 A | 11/1996 | Davis et al. |
| 5,577,609 A | 11/1996 | Hexter |
| 5,578,808 A | 11/1996 | Taylor |
| 5,581,630 A | 12/1996 | Bonneau, Jr. |
| 5,585,787 A | 12/1996 | Wallerstein |
| 5,590,038 A | 12/1996 | Pitroda |
| 5,590,197 A | 12/1996 | Chen et al. |
| 5,592,150 A | 1/1997 | dHont |
| 5,592,405 A | 1/1997 | Gove et al. |
| 5,592,767 A | 1/1997 | Treske |
| 5,594,227 A | 1/1997 | Deo |
| 5,594,233 A | 1/1997 | Kenneth et al. |
| 5,594,448 A | 1/1997 | dHont |
| 5,597,534 A | 1/1997 | Kaiser |
| 5,600,175 A | 2/1997 | Orthmann |
| 5,602,538 A | 2/1997 | Orthmann et al. |
| 5,602,918 A | 2/1997 | Chen et al. |
| 5,602,919 A | 2/1997 | Hurta et al. |
| 5,604,342 A | 2/1997 | Fujioka |
| 5,604,801 A | 2/1997 | Dolan et al. |
| 5,606,520 A | 2/1997 | Gove et al. |
| 5,606,594 A | 2/1997 | Register et al. |
| 5,607,522 A | 3/1997 | McDonnell |
| 5,608,203 A | 3/1997 | Finkelstein et al. |
| 5,608,406 A | 3/1997 | Eberth et al. |
| 5,608,778 A | 3/1997 | Partridge, III |
| 5,611,965 A | 3/1997 | Shouji et al. |
| 5,613,001 A | 3/1997 | Bakhoum |
| 5,613,131 A | 3/1997 | Moss et al. |
| 5,613,146 A | 3/1997 | Gove et al. |
| 5,614,703 A | 3/1997 | Martin et al. |
| 5,619,207 A | 4/1997 | dHont |
| 5,621,199 A | 4/1997 | Calari et al. |
| 5,621,396 A | 4/1997 | Flaxl |
| 5,621,411 A | 4/1997 | Hagl et al. |
| 5,621,412 A | 4/1997 | Sharpe et al. |
| 5,625,366 A | 4/1997 | dHont |
| 5,625,370 A | 4/1997 | dHont |
| 5,625,695 A | 4/1997 | MRaihi et al. |
| 5,629,981 A | 5/1997 | Nerlikar |
| 5,638,080 A | 6/1997 | Orthmann et al. |
| 5,640,002 A | 6/1997 | Ruppert et al. |
| 5,641,050 A | 6/1997 | Smith et al. |
| 5,646,607 A | 7/1997 | Schuermann et al. |
| 5,649,118 A | 7/1997 | Carlisle et al. |
| 5,657,388 A | 8/1997 | Weiss |
| 5,660,319 A | 8/1997 | Falcone et al. |
| 5,665,439 A | 9/1997 | Andersen et al. |
| 5,668,876 A | 9/1997 | Falk et al. |
| 5,673,106 A | 9/1997 | Thompson |
| D384,971 S | 10/1997 | Kawan |
| 5,675,342 A | 10/1997 | Sharpe |
| 5,677,953 A | 10/1997 | Dolphin |
| 5,686,920 A | 11/1997 | Hurta et al. |
| 5,689,100 A | 11/1997 | Carrithers |
| 5,691,731 A | 11/1997 | vanErven |
| 5,692,132 A | 11/1997 | Hogan |
| 5,694,596 A | 12/1997 | Campbell |
| 5,696,913 A | 12/1997 | Gove et al. |
| 5,697,649 A | 12/1997 | Dames et al. |
| 5,698,837 A | 12/1997 | Furuta |
| 5,699,528 A | 12/1997 | Hogan |
| 5,700,037 A | 12/1997 | Keller |
| 5,701,127 A | 12/1997 | Sharpe |
| 5,704,046 A | 12/1997 | Hogan |

(56) References Cited

U.S. PATENT DOCUMENTS

| | | | |
|---|---|---|---|
| 5,705,101 | A | 1/1998 | Oi et al. |
| 5,705,798 | A | 1/1998 | Tarbox |
| 5,705,852 | A | 1/1998 | Orihara et al. |
| 5,710,421 | A | 1/1998 | Kokubu |
| 5,715,399 | A | 2/1998 | Bezos |
| 5,720,500 | A | 2/1998 | Okazaki et al. |
| 5,721,781 | A | 2/1998 | Deo et al. |
| 5,724,424 | A | 3/1998 | Gifford |
| 5,725,098 | A | 3/1998 | Seifert et al. |
| 5,727,140 | A | 3/1998 | Ohtomo et al. |
| 5,727,696 | A | 3/1998 | Valiulis |
| 5,729,053 | A | 3/1998 | Orthmann |
| 5,729,236 | A | 3/1998 | Flaxl |
| 5,731,957 | A | 3/1998 | Brennan |
| 5,732,579 | A | 3/1998 | dHont et al. |
| 5,734,838 | A | 3/1998 | Robinson et al. |
| 5,737,439 | A | 4/1998 | Lapsley et al. |
| 5,739,512 | A | 4/1998 | Tognazzini |
| 5,742,756 | A | 4/1998 | Dillaway et al. |
| 5,742,845 | A | 4/1998 | Wagner |
| 5,745,571 | A | 4/1998 | Zuk |
| 5,748,137 | A | 5/1998 | dHont |
| 5,748,737 | A | 5/1998 | Daggar |
| 5,757,917 | A | 5/1998 | Rose et al. |
| 5,758,195 | A | 5/1998 | Balmer |
| 5,761,306 | A | 6/1998 | Lewis |
| 5,761,493 | A | 6/1998 | Blakeley et al. |
| 5,764,789 | A | 6/1998 | Pare, Jr. et al. |
| 5,768,385 | A | 6/1998 | Simon |
| 5,768,609 | A | 6/1998 | Gove et al. |
| 5,769,457 | A | 6/1998 | Warther |
| 5,770,843 | A | 6/1998 | Rose et al. |
| 5,773,812 | A | 6/1998 | Kreft |
| 5,774,882 | A | 6/1998 | Keen et al. |
| 5,777,903 | A | 7/1998 | Piosenka |
| 5,778,067 | A | 7/1998 | Jones et al. |
| 5,778,069 | A | 7/1998 | Thomlinson |
| 5,778,173 | A | 7/1998 | Apte |
| 5,785,680 | A | 7/1998 | Niezink et al. |
| 5,786,587 | A | 7/1998 | Colgate, Jr. |
| 5,789,733 | A | 8/1998 | Jachimowicz et al. |
| 5,791,474 | A | 8/1998 | Hansen |
| 5,792,337 | A | 8/1998 | Padovani et al. |
| 5,793,324 | A | 8/1998 | Aslanidis et al. |
| 5,794,095 | A | 8/1998 | Thompson |
| 5,796,831 | A | 8/1998 | Paradinas et al. |
| 5,797,060 | A | 8/1998 | Thompson |
| 5,797,085 | A | 8/1998 | Buek et al. |
| 5,797,133 | A | 8/1998 | Jones et al. |
| 5,798,709 | A | 8/1998 | Flaxl |
| 5,799,087 | A | 8/1998 | Rosen |
| 5,806,045 | A | 9/1998 | Biorge et al. |
| 5,808,758 | A | 9/1998 | Solmsdorf |
| 5,809,142 | A | 9/1998 | Hurta et al. |
| 5,809,288 | A | 9/1998 | Balmer |
| 5,809,633 | A | 9/1998 | Mundigl et al. |
| 5,815,252 | A | 9/1998 | Price-Francis |
| 5,815,657 | A | 9/1998 | Williams et al. |
| 5,823,359 | A | 10/1998 | Harris et al. |
| 5,825,007 | A | 10/1998 | Jesadanont |
| 5,825,302 | A | 10/1998 | Stafford |
| 5,826,077 | A | 10/1998 | Blakeley et al. |
| 5,826,241 | A | 10/1998 | Stein et al. |
| 5,826,242 | A | 10/1998 | Montulli |
| 5,826,243 | A | 10/1998 | Musmanno et al. |
| 5,828,044 | A | 10/1998 | Jun et al. |
| 5,834,756 | A | 11/1998 | Gutman et al. |
| 5,835,894 | A | 11/1998 | Adcock et al. |
| 5,838,257 | A | 11/1998 | Lambropoulos |
| 5,838,720 | A | 11/1998 | Morelli |
| 5,838,812 | A | 11/1998 | Pare, Jr. et al. |
| 5,841,364 | A | 11/1998 | Hagl et al. |
| 5,842,088 | A | 11/1998 | Thompson |
| 5,844,218 | A | 12/1998 | Kawan et al. |
| 5,844,230 | A | 12/1998 | Lalonde |
| 5,845,267 | A | 12/1998 | Ronen |
| 5,851,149 | A | 12/1998 | Xidos et al. |
| 5,852,812 | A | 12/1998 | Reeder |
| 5,854,891 | A | 12/1998 | Postlewaite et al. |
| 5,856,048 | A | 1/1999 | Tahara et al. |
| 5,857,079 | A | 1/1999 | Claus et al. |
| 5,857,152 | A | 1/1999 | Everett |
| 5,857,709 | A | 1/1999 | Chock |
| 5,858,006 | A | 1/1999 | Van der AA et al. |
| 5,859,419 | A | 1/1999 | Wynn |
| 5,859,587 | A | 1/1999 | Alicot et al. |
| 5,859,779 | A | 1/1999 | Giordano et al. |
| 5,862,325 | A | 1/1999 | Reed et al. |
| 5,864,306 | A | 1/1999 | Dwyer et al. |
| 5,864,323 | A | 1/1999 | Berthon |
| 5,864,830 | A | 1/1999 | Armetta et al. |
| 5,865,470 | A | 2/1999 | Thompson |
| 5,867,100 | A | 2/1999 | dHont |
| 5,869,822 | A | 2/1999 | Meadows et al. |
| 5,870,031 | A | 2/1999 | Kaiser et al. |
| 5,870,915 | A | 2/1999 | dHont |
| 5,875,432 | A | 2/1999 | Sehr |
| D406,861 | S | 3/1999 | Leedy, Jr. |
| 5,878,138 | A | 3/1999 | Yacobi |
| 5,878,141 | A | 3/1999 | Daly et al. |
| 5,878,215 | A | 3/1999 | Kling et al. |
| 5,878,337 | A | 3/1999 | Joao et al. |
| 5,878,403 | A | 3/1999 | DeFrancesco et al. |
| 5,880,675 | A | 3/1999 | Trautner |
| 5,881,272 | A | 3/1999 | Balmer |
| 5,883,377 | A | 3/1999 | Chapin, Jr. |
| 5,883,810 | A | 3/1999 | Franklin et al. |
| 5,884,271 | A * | 3/1999 | Pitroda .......................... 705/1 |
| 5,884,280 | A | 3/1999 | Yoshioka et al. |
| 5,884,292 | A | 3/1999 | Baker et al. |
| 5,884,310 | A | 3/1999 | Brichta et al. |
| 5,886,333 | A | 3/1999 | Miyake |
| 5,887,266 | A | 3/1999 | Heinonen et al. |
| 5,889,941 | A | 3/1999 | Tushie et al. |
| 5,890,137 | A | 3/1999 | Koreeda |
| D408,054 | S | 4/1999 | Leedy, Jr. |
| 5,892,211 | A | 4/1999 | Davis et al. |
| 5,897,622 | A | 4/1999 | Blinn et al. |
| 5,898,783 | A | 4/1999 | Rohrbach |
| 5,898,838 | A | 4/1999 | Wagner |
| 5,900,954 | A | 5/1999 | Katz et al. |
| 5,901,239 | A | 5/1999 | Kamei |
| 5,903,830 | A | 5/1999 | Joao et al. |
| 5,903,875 | A | 5/1999 | Kohara |
| 5,903,880 | A | 5/1999 | Biffar |
| 5,905,798 | A | 5/1999 | Nerlikar et al. |
| 5,905,908 | A | 5/1999 | Wagner |
| 5,907,620 | A | 5/1999 | Klemba et al. |
| 5,909,492 | A | 6/1999 | Payne et al. |
| 5,912,446 | A | 6/1999 | Wong et al. |
| 5,912,678 | A | 6/1999 | Saxena et al. |
| 5,913,203 | A | 6/1999 | Wong et al. |
| 5,914,472 | A | 6/1999 | Foladare et al. |
| 5,915,016 | A | 6/1999 | Savalle et al. |
| 5,915,023 | A | 6/1999 | Bernstein |
| 5,915,973 | A | 6/1999 | Hoehn-Saric et al. |
| 5,917,168 | A | 6/1999 | Nakamura et al. |
| 5,917,913 | A | 6/1999 | Wang |
| 5,917,925 | A | 6/1999 | Moore |
| 5,918,216 | A | 6/1999 | Miksovsky et al. |
| 5,920,058 | A | 7/1999 | Weber et al. |
| 5,920,628 | A | 7/1999 | Indeck et al. |
| 5,920,629 | A | 7/1999 | Rosen |
| 5,920,847 | A | 7/1999 | Kolling et al. |
| 5,923,734 | A | 7/1999 | Taskett |
| 5,923,884 | A | 7/1999 | Peyret et al. |
| 5,924,080 | A | 7/1999 | Johnson |
| 5,924,624 | A | 7/1999 | Martin |
| 5,928,788 | A | 7/1999 | Riedl |
| 5,929,801 | A | 7/1999 | Aslanidis et al. |
| 5,930,767 | A | 7/1999 | Reber et al. |
| 5,930,777 | A | 7/1999 | Barber |
| 5,931,917 | A | 8/1999 | Nguyen et al. |
| 5,932,870 | A | 8/1999 | Berson |

(56) References Cited

U.S. PATENT DOCUMENTS

| | | |
|---|---|---|
| 5,933,328 A | 8/1999 | Wallace et al. |
| 5,933,624 A | 8/1999 | Balmer |
| 5,936,226 A | 8/1999 | Aucsmith |
| 5,936,227 A | 8/1999 | Truggelmann et al. |
| 5,938,010 A | 8/1999 | Osterbye |
| 5,942,761 A | 8/1999 | Tuli |
| 5,943,624 A | 8/1999 | Fox et al. |
| 5,945,653 A | 8/1999 | Walker et al. |
| 5,948,116 A | 9/1999 | Aslanidis et al. |
| 5,949,044 A | 9/1999 | Walker et al. |
| 5,949,335 A | 9/1999 | Maynard |
| 5,949,876 A | 9/1999 | Ginter et al. |
| 5,950,174 A | 9/1999 | Brendzel |
| 5,950,179 A | 9/1999 | Buchanan et al. |
| 5,953,512 A | 9/1999 | Cai et al. |
| 5,953,710 A | 9/1999 | Fleming |
| 5,955,717 A | 9/1999 | Vanstone |
| 5,955,951 A | 9/1999 | Wischerop et al. |
| 5,955,969 A | 9/1999 | dHont |
| 5,956,024 A | 9/1999 | Strickland et al. |
| 5,956,693 A | 9/1999 | Geerlings |
| 5,956,699 A | 9/1999 | Wong et al. |
| 5,958,004 A | 9/1999 | Helland et al. |
| 5,960,411 A | 9/1999 | Hartman et al. |
| 5,960,416 A | 9/1999 | Block |
| 5,963,915 A | 10/1999 | Kirsch |
| 5,963,924 A | 10/1999 | Williams et al. |
| 5,966,697 A | 10/1999 | Fergerson et al. |
| 5,968,570 A | 10/1999 | Paulucci |
| 5,969,318 A | 10/1999 | Mackenthun |
| 5,970,148 A | 10/1999 | Meier |
| 5,970,470 A | 10/1999 | Walker |
| 5,970,471 A | 10/1999 | Hill |
| 5,970,472 A | 10/1999 | Allsop et al. |
| 5,970,473 A | 10/1999 | Gerszberg et al. |
| 5,970,475 A | 10/1999 | Barnes et al. |
| 5,971,276 A | 10/1999 | Sano et al. |
| 5,973,475 A | 10/1999 | Combaluzier |
| 5,974,238 A | 10/1999 | Chase, Jr. |
| RE36,365 E | 11/1999 | Levine et al. |
| 5,978,348 A | 11/1999 | Tamura |
| 5,978,840 A | 11/1999 | Nguyen et al. |
| 5,979,757 A | 11/1999 | Tracy et al. |
| 5,979,942 A | 11/1999 | Ivicic |
| 5,982,293 A | 11/1999 | Everett et al. |
| 5,983,200 A | 11/1999 | Slotznick |
| 5,983,207 A | 11/1999 | Turk et al. |
| 5,983,208 A | 11/1999 | Haller |
| 5,984,180 A | 11/1999 | Albrecht |
| 5,987,140 A | 11/1999 | Rowney et al. |
| 5,987,155 A | 11/1999 | Dunn et al. |
| 5,987,498 A | 11/1999 | Athing et al. |
| 5,988,497 A | 11/1999 | Wallace |
| 5,988,510 A | 11/1999 | Tuttle |
| 5,989,950 A | 11/1999 | Wu |
| 5,991,413 A | 11/1999 | Arditti et al. |
| 5,991,608 A | 11/1999 | Leyten |
| 5,991,748 A | 11/1999 | Taskett |
| 5,991,750 A | 11/1999 | Watson |
| 5,995,014 A | 11/1999 | DiMaria |
| 5,996,076 A | 11/1999 | Rowney et al. |
| 5,999,914 A | 12/1999 | Blinn et al. |
| 6,000,832 A | 12/1999 | Franklin et al. |
| 6,002,438 A | 12/1999 | Hocevar et al. |
| 6,002,767 A | 12/1999 | Kramer |
| 6,003,014 A | 12/1999 | Lee et al. |
| 6,005,942 A | 12/1999 | Chan et al. |
| 6,006,216 A | 12/1999 | Griffin et al. |
| 6,006,988 A | 12/1999 | Behrmann et al. |
| 6,009,412 A | 12/1999 | Storey |
| 6,011,487 A | 1/2000 | Plocher |
| 6,012,039 A | 1/2000 | Hoffman et al. |
| 6,012,049 A | 1/2000 | Kawan |
| 6,012,143 A | 1/2000 | Tanaka |
| 6,012,636 A | 1/2000 | Smith |
| 6,014,634 A | 1/2000 | Scroggie et al. |
| 6,014,635 A | 1/2000 | Harris et al. |
| 6,014,636 A | 1/2000 | Reeder |
| 6,014,645 A | 1/2000 | Cunningham |
| 6,014,646 A | 1/2000 | Vallee et al. |
| 6,014,648 A | 1/2000 | Brennan |
| 6,014,650 A | 1/2000 | Zampese |
| 6,014,748 A | 1/2000 | Tushi et al. |
| 6,016,476 A | 1/2000 | Maes et al. |
| 6,016,482 A | 1/2000 | Molinari et al. |
| 6,016,484 A | 1/2000 | Williams et al. |
| 6,018,717 A | 1/2000 | Lee et al. |
| 6,018,718 A | 1/2000 | Walker et al. |
| RE36,580 E | 2/2000 | Bogosian, Jr. |
| 6,021,943 A | 2/2000 | Chastain |
| 6,023,510 A | 2/2000 | Epstein |
| 6,024,286 A | 2/2000 | Bradley et al. |
| 6,024,385 A | 2/2000 | Goda |
| 6,025,283 A | 2/2000 | Roberts |
| 6,027,028 A | 2/2000 | Pieterse et al. |
| 6,029,147 A | 2/2000 | Horadan et al. |
| 6,029,149 A | 2/2000 | Dykstra et al. |
| 6,029,150 A | 2/2000 | Kravitz |
| 6,029,175 A | 2/2000 | Chow |
| 6,029,890 A | 2/2000 | Austin |
| 6,029,892 A | 2/2000 | Miyake |
| 6,032,136 A | 2/2000 | Brake, Jr. et al. |
| 6,032,866 A | 3/2000 | Knighton et al. |
| 6,036,100 A | 3/2000 | Asami |
| 6,038,292 A | 3/2000 | Thomas |
| 6,038,551 A | 3/2000 | Barlow et al. |
| 6,038,584 A | 3/2000 | Balmer |
| 6,041,308 A | 3/2000 | Walker et al. |
| 6,041,410 A | 3/2000 | Hsu et al. |
| 6,041,412 A | 3/2000 | Timson et al. |
| 6,044,360 A | 3/2000 | Picciallo |
| 6,044,388 A | 3/2000 | DeBellis et al. |
| 6,047,888 A | 4/2000 | Dethloff |
| 6,050,494 A | 4/2000 | Song et al. |
| 6,050,605 A | 4/2000 | Mikelionis et al. |
| 6,052,675 A | 4/2000 | Checchio |
| 6,058,418 A | 5/2000 | Kobata |
| 6,060,815 A | 5/2000 | Nysen |
| 6,061,344 A | 5/2000 | Wood, Jr. |
| 6,061,789 A | 5/2000 | Hauser et al. |
| 6,064,320 A | 5/2000 | dHont et al. |
| 6,064,751 A | 5/2000 | Smithies et al. |
| 6,064,981 A | 5/2000 | Barni et al. |
| 6,065,675 A | 5/2000 | Teicher |
| 6,068,184 A | 5/2000 | Barnett |
| 6,068,193 A | 5/2000 | Kreft |
| 6,070,003 A | 5/2000 | Gove et al. |
| 6,070,150 A | 5/2000 | Remington et al. |
| 6,070,154 A | 5/2000 | Tavor et al. |
| 6,072,870 A | 6/2000 | Nguyen et al. |
| 6,073,112 A | 6/2000 | Geerlings |
| 6,073,236 A | 6/2000 | Kusakabe et al. |
| 6,073,840 A | 6/2000 | Marion |
| 6,076,078 A | 6/2000 | Camp et al. |
| 6,076,296 A | 6/2000 | Schaeffer |
| 6,078,888 A | 6/2000 | Johnson, Jr. |
| 6,078,906 A | 6/2000 | Huberman |
| 6,078,908 A | 6/2000 | Schmitz |
| 6,081,790 A | 6/2000 | Rosen |
| RE36,788 E | 7/2000 | Mansvelt et al. |
| 6,082,422 A | 7/2000 | Kaminski |
| 6,084,967 A | 7/2000 | Kennedy et al. |
| 6,085,976 A | 7/2000 | Sehr |
| 6,086,971 A | 7/2000 | Haas et al. |
| 6,088,683 A | 7/2000 | Jalili |
| 6,088,686 A | 7/2000 | Walker et al. |
| 6,088,717 A | 7/2000 | Reed et al. |
| 6,088,755 A | 7/2000 | Kobayashi et al. |
| 6,088,797 A | 7/2000 | Rosen |
| 6,089,611 A | 7/2000 | Blank |
| 6,091,835 A | 7/2000 | Smithies et al. |
| 6,092,057 A | 7/2000 | Zimmerman et al. |
| 6,092,198 A | 7/2000 | Lanzy et al. |
| 6,095,413 A | 8/2000 | Tetro et al. |

(56) References Cited

U.S. PATENT DOCUMENTS

| | | | |
|---|---|---|---|
| 6,095,567 A | 8/2000 | Buell | |
| 6,098,053 A | 8/2000 | Slater | |
| 6,098,879 A | 8/2000 | Terranova | |
| 6,099,043 A | 8/2000 | Story | |
| 6,100,804 A | 8/2000 | Brady et al. | |
| 6,101,174 A | 8/2000 | Langston | |
| 6,101,477 A * | 8/2000 | Hohle et al. | 705/1 |
| 6,102,162 A | 8/2000 | Teicher | |
| 6,102,672 A | 8/2000 | Woollenweber | |
| 6,104,281 A | 8/2000 | Heinrich et al. | |
| 6,104,311 A | 8/2000 | Lastinger | |
| 6,104,922 A | 8/2000 | Baumann | |
| 6,105,008 A * | 8/2000 | Davis et al. | 705/41 |
| 6,105,013 A | 8/2000 | Curry et al. | |
| 6,105,865 A | 8/2000 | Hardesty | |
| 6,107,920 A | 8/2000 | Eberhardt et al. | |
| 6,108,641 A | 8/2000 | Kenna et al. | |
| 6,109,525 A | 8/2000 | Blomqvist et al. | |
| 6,112,152 A | 8/2000 | Tuttle | |
| 6,112,191 A | 8/2000 | Burke | |
| 6,112,984 A | 9/2000 | Snavely | |
| 6,115,040 A | 9/2000 | Bladow et al. | |
| 6,115,360 A | 9/2000 | Quay et al. | |
| 6,115,458 A | 9/2000 | Taskett | |
| 6,116,423 A | 9/2000 | Troxtell, Jr. et al. | |
| 6,116,505 A | 9/2000 | Withrow | |
| 6,116,655 A | 9/2000 | Thouin et al. | |
| 6,116,736 A | 9/2000 | Stark et al. | |
| 6,118,189 A | 9/2000 | Flaxl | |
| 6,120,461 A | 9/2000 | Smyth | |
| 6,121,544 A | 9/2000 | Petsinger | |
| 6,122,625 A | 9/2000 | Rosen | |
| 6,123,223 A | 9/2000 | Watkins | |
| 6,125,352 A | 9/2000 | Franklin et al. | |
| D432,939 S | 10/2000 | Hooglander | |
| 6,128,604 A | 10/2000 | Sakamaki et al. | |
| 6,129,274 A | 10/2000 | Suzuki | |
| 6,130,623 A | 10/2000 | MacLellan et al. | |
| 6,133,834 A | 10/2000 | Eberth et al. | |
| 6,138,913 A | 10/2000 | Cyr et al. | |
| 6,138,917 A | 10/2000 | Chapin, Jr. | |
| 6,141,651 A | 10/2000 | Riley et al. | |
| 6,141,752 A | 10/2000 | Dancs et al. | |
| 6,144,916 A | 11/2000 | Wood et al. | |
| 6,144,948 A | 11/2000 | Walker et al. | |
| 6,148,093 A | 11/2000 | McConnell et al. | |
| 6,148,484 A | 11/2000 | Andreae, Jr. | |
| 6,154,879 A | 11/2000 | Pare et al. | |
| 6,155,168 A | 12/2000 | Sakamoto | |
| 6,157,824 A | 12/2000 | Bailey | |
| 6,163,771 A | 12/2000 | Walker et al. | |
| 6,167,236 A | 12/2000 | Kaiser et al. | |
| 6,168,083 B1 | 1/2001 | Berger et al. | |
| 6,171,138 B1 | 1/2001 | Lefebvre et al. | |
| 6,173,269 B1 | 1/2001 | Solokl et al. | |
| 6,173,272 B1 | 1/2001 | Thomas et al. | |
| 6,173,897 B1 | 1/2001 | Halpern | |
| 6,173,898 B1 | 1/2001 | Mande | |
| 6,173,899 B1 | 1/2001 | Rozin | |
| 6,177,859 B1 | 1/2001 | Tuttle et al. | |
| 6,177,860 B1 | 1/2001 | Cromer et al. | |
| 6,179,205 B1 | 1/2001 | Sloan | |
| 6,179,206 B1 | 1/2001 | Matsumori | |
| 6,181,287 B1 | 1/2001 | Beigel | |
| 6,182,895 B1 | 2/2001 | Albrecht | |
| 6,184,788 B1 | 2/2001 | Middlemiss et al. | |
| 6,185,307 B1 * | 2/2001 | Johnson, Jr. | 380/270 |
| 6,188,994 B1 | 2/2001 | Egendorf | |
| 6,189,779 B1 | 2/2001 | Verdicchio et al. | |
| 6,189,787 B1 | 2/2001 | Dorf | |
| 6,192,255 B1 | 2/2001 | Lewis et al. | |
| 6,195,006 B1 | 2/2001 | Bowers et al. | |
| 6,196,465 B1 | 3/2001 | Awano | |
| 6,197,396 B1 | 3/2001 | Haas et al. | |
| 6,198,728 B1 | 3/2001 | Hulyalkar et al. | |
| 6,198,762 B1 | 3/2001 | Krasnov | |
| 6,198,875 B1 | 3/2001 | Edenson et al. | |
| 6,199,079 B1 | 3/2001 | Gupta et al. | |
| 6,199,762 B1 * | 3/2001 | Hohle | 235/492 |
| 6,200,272 B1 | 3/2001 | Linden | |
| 6,202,927 B1 | 3/2001 | Bashan et al. | |
| 6,205,151 B1 | 3/2001 | Quay et al. | |
| 6,206,293 B1 | 3/2001 | Gutman et al. | |
| 6,213,390 B1 | 4/2001 | Oneda | |
| 6,213,391 B1 | 4/2001 | Lewis | |
| 6,215,437 B1 | 4/2001 | Schurmann et al. | |
| 6,216,219 B1 | 4/2001 | Cai et al. | |
| 6,219,439 B1 | 4/2001 | Burger | |
| 6,220,510 B1 | 4/2001 | Everett et al. | |
| 6,222,914 B1 | 4/2001 | McMullin | |
| D442,627 S | 5/2001 | Webb et al. | |
| D442,629 S | 5/2001 | Webb et al. | |
| 6,223,977 B1 | 5/2001 | Hill | |
| 6,223,984 B1 | 5/2001 | Renner et al. | |
| 6,224,109 B1 | 5/2001 | Yang | |
| 6,226,382 B1 | 5/2001 | MRaihi et al. | |
| 6,227,424 B1 | 5/2001 | Roegner | |
| 6,227,447 B1 | 5/2001 | Campisano | |
| 6,230,270 B1 | 5/2001 | Laczko, Sr. | |
| 6,232,917 B1 | 5/2001 | Baumer et al. | |
| 6,233,348 B1 | 5/2001 | Fujii et al. | |
| 6,233,683 B1 | 5/2001 | Chan et al. | |
| 6,237,848 B1 | 5/2001 | Everett | |
| 6,239,675 B1 | 5/2001 | Flaxl | |
| 6,240,187 B1 | 5/2001 | Lewis | |
| 6,240,989 B1 | 6/2001 | Masoud | |
| 6,247,030 B1 | 6/2001 | Suzuki | |
| 6,248,199 B1 | 6/2001 | Smulson | |
| 6,248,314 B1 | 6/2001 | Nakashimada et al. | |
| 6,250,554 B1 | 6/2001 | Leo et al. | |
| 6,250,557 B1 | 6/2001 | Forslund et al. | |
| 6,255,031 B1 | 7/2001 | Yao et al. | |
| 6,257,486 B1 | 7/2001 | Teicher et al. | |
| 6,259,769 B1 | 7/2001 | Page | |
| 6,260,026 B1 | 7/2001 | Tomida et al. | |
| 6,260,088 B1 | 7/2001 | Gove et al. | |
| 6,263,316 B1 | 7/2001 | Khan et al. | |
| 6,263,446 B1 | 7/2001 | Kausik et al. | |
| 6,264,106 B1 | 7/2001 | Bridgelall | |
| 6,265,977 B1 | 7/2001 | Vega et al. | |
| 6,266,754 B1 | 7/2001 | Laczko, Sr. et al. | |
| 6,267,292 B1 | 7/2001 | Walker et al. | |
| 6,268,788 B1 | 7/2001 | Gray | |
| 6,269,348 B1 | 7/2001 | Pare, Jr. et al. | |
| 6,273,335 B1 | 8/2001 | Sloan | |
| 6,277,232 B1 | 8/2001 | Wang et al. | |
| 6,282,522 B1 | 8/2001 | Davis et al. | |
| D447,515 S | 9/2001 | Faenza, Jr. et al. | |
| 6,286,763 B1 | 9/2001 | Reynolds et al. | |
| 6,289,324 B1 | 9/2001 | Kawan | |
| 6,290,137 B1 | 9/2001 | Kiekhaefer | |
| 6,293,462 B1 | 9/2001 | Gangi | |
| 6,295,522 B1 | 9/2001 | Boesch | |
| 6,296,188 B1 | 10/2001 | Kiekhaefer | |
| 6,297,727 B1 | 10/2001 | Nelson, Jr. | |
| 6,304,223 B1 | 10/2001 | Hilton et al. | |
| 6,307,956 B1 | 10/2001 | Black | |
| 6,309,098 B1 | 10/2001 | Wong | |
| 6,315,193 B1 | 11/2001 | Hogan | |
| 6,315,195 B1 | 11/2001 | Ramacchandran | |
| 6,315,206 B1 | 11/2001 | Hansen et al. | |
| 6,317,721 B1 | 11/2001 | Hurta et al. | |
| 6,317,750 B1 | 11/2001 | Tortolani et al. | |
| 6,317,755 B1 * | 11/2001 | Rakers et al. | 707/204 |
| 6,318,636 B1 | 11/2001 | Reynolds et al. | |
| 6,323,566 B1 | 11/2001 | Meier | |
| 6,325,285 B1 | 12/2001 | Baratelli | |
| 6,325,293 B1 | 12/2001 | Moreno | |
| 6,326,934 B1 | 12/2001 | Kinzie | |
| 6,327,573 B1 | 12/2001 | Walker et al. | |
| 6,327,578 B1 | 12/2001 | Linehan | |
| 6,329,920 B1 | 12/2001 | Morrison et al. | |
| 6,330,544 B1 | 12/2001 | Walker et al. | |
| 6,331,972 B1 | 12/2001 | Harris et al. | |

(56) References Cited

U.S. PATENT DOCUMENTS

| | | | |
|---|---|---|---|
| 6,332,134 B1 | 12/2001 | Foster |
| 6,332,193 B1 | 12/2001 | Glass et al. |
| D453,160 S | 1/2002 | Pentz et al. |
| D453,161 S | 1/2002 | Pentz |
| 6,336,095 B1 | 1/2002 | Rosen |
| 6,338,048 B1 | 1/2002 | Mori |
| 6,339,384 B1 | 1/2002 | Valdes-Rodriguez |
| 6,342,844 B1 | 1/2002 | Rozin |
| D453,337 S | 2/2002 | Pentz et al. |
| D453,338 S | 2/2002 | Pentz et al. |
| D453,516 S | 2/2002 | Pentz |
| D454,910 S | 3/2002 | Smith et al. |
| 6,353,420 B1 | 3/2002 | Chung |
| 6,353,811 B1 | 3/2002 | Weissman |
| 6,360,953 B1 | 3/2002 | Lin et al. |
| 6,364,208 B1 | 4/2002 | Stanford et al. |
| 6,367,011 B1 | 4/2002 | Lee et al. |
| 6,374,245 B1 | 4/2002 | Park |
| 6,377,034 B1 | 4/2002 | Ivanov |
| 6,378,073 B1 | 4/2002 | Davis et al. |
| D457,556 S | 5/2002 | Hochschild |
| 6,386,444 B1 | 5/2002 | Sullivan |
| 6,388,533 B2 | 5/2002 | Swoboda |
| 6,390,375 B2 | 5/2002 | Kayanakis |
| 6,400,272 B1 | 6/2002 | Holtzman et al. |
| 6,402,026 B1 | 6/2002 | Schwier |
| 6,402,028 B1 | 6/2002 | Graham, Jr. et al. |
| 6,404,341 B1 | 6/2002 | Reid |
| 6,406,935 B2 | 6/2002 | Kayanakis et al. |
| 6,411,611 B1 | 6/2002 | Van der Tuijn |
| D460,455 S | 7/2002 | Pentz |
| 6,415,978 B1 | 7/2002 | McAllister |
| 6,419,158 B2 | 7/2002 | Hooglander |
| 6,421,650 B1 | 7/2002 | Goetz et al. |
| 6,422,462 B1 | 7/2002 | Cohen |
| 6,422,464 B1 | 7/2002 | Terranova |
| 6,422,472 B1 | 7/2002 | Thevenot et al. |
| 6,424,029 B1 | 7/2002 | Giesler |
| 6,424,249 B1 | 7/2002 | Houvener |
| RE37,822 E | 8/2002 | Anthonyson |
| D461,477 S | 8/2002 | Pentz |
| 6,427,910 B1 | 8/2002 | Barnes et al. |
| 6,434,159 B1 | 8/2002 | Woodward et al. |
| 6,435,415 B1 | 8/2002 | Catte |
| 6,438,235 B2 | 8/2002 | Sims, III |
| 6,439,455 B1 | 8/2002 | Everett et al. |
| 6,442,532 B1 | 8/2002 | Kawan |
| D462,965 S | 9/2002 | Pentz |
| D462,966 S | 9/2002 | Pentz et al. |
| 6,445,794 B1 | 9/2002 | Shefi |
| 6,446,862 B1 | 9/2002 | Mann |
| 6,457,000 B1 | 9/2002 | Witkowski et al. |
| 6,457,996 B1 | 10/2002 | Shih |
| 6,460,696 B1 | 10/2002 | Meyer |
| 6,466,804 B1 | 10/2002 | Pecen et al. |
| 6,471,127 B2 | 10/2002 | Pentz et al. |
| 6,473,500 B1 | 10/2002 | Risafi et al. |
| 6,480,100 B1 * | 11/2002 | Frieden et al. ............... 340/10.1 |
| 6,480,101 B1 | 11/2002 | Kelly et al. |
| 6,480,825 B1 | 11/2002 | Sharma et al. |
| 6,480,869 B1 | 11/2002 | Fujioka |
| 6,481,621 B1 | 11/2002 | Herrendoerfer et al. |
| 6,481,623 B1 | 11/2002 | Grant et al. |
| 6,481,632 B2 | 11/2002 | Wentker et al. |
| 6,483,427 B1 | 11/2002 | Werb |
| 6,483,477 B1 | 11/2002 | Plonka |
| 6,483,929 B1 | 11/2002 | Murakami et al. |
| 6,484,937 B1 | 11/2002 | Devaux et al. |
| 6,490,443 B1 | 12/2002 | Freeny, Jr. |
| 6,491,229 B1 | 12/2002 | Berney |
| 6,491,639 B1 | 12/2002 | Turcott |
| 6,494,367 B1 | 12/2002 | Zacharias |
| 6,494,380 B2 | 12/2002 | Jarosz |
| 6,496,594 B1 | 12/2002 | Prokoski |
| 6,501,832 B1 | 12/2002 | Saylor et al. |
| 6,505,772 B1 | 1/2003 | Mollett et al. |
| 6,507,662 B1 | 1/2003 | Brooks |
| 6,507,762 B1 | 1/2003 | Amro et al. |
| 6,510,983 B2 | 1/2003 | Horowitz et al. |
| 6,510,998 B1 | 1/2003 | Stanford et al. |
| 6,513,015 B2 | 1/2003 | Ogasawara |
| 6,519,565 B1 | 2/2003 | Clements et al. |
| 6,520,542 B2 | 2/2003 | Thompson et al. |
| 6,523,292 B2 | 2/2003 | Slavik |
| 6,529,880 B1 | 3/2003 | McKeen et al. |
| 6,535,726 B1 | 3/2003 | Johnson |
| 6,539,101 B1 | 3/2003 | Black |
| 6,546,373 B1 | 4/2003 | Cerra |
| 6,547,133 B1 | 4/2003 | DeVries, Jr. et al. |
| 6,549,912 B1 | 4/2003 | Chen |
| D474,234 S | 5/2003 | Nelms et al. |
| 6,560,581 B1 | 5/2003 | Fox et al. |
| 6,575,361 B1 | 6/2003 | Graves et al. |
| 6,577,229 B1 | 6/2003 | Bonneau et al. |
| 6,578,768 B1 | 6/2003 | Binder et al. |
| 6,581,839 B1 | 6/2003 | Lasch et al. |
| 6,587,835 B1 | 7/2003 | Treyz et al. |
| 6,588,660 B1 | 7/2003 | Buescher et al. |
| 6,588,673 B1 | 7/2003 | Chan et al. |
| 6,589,119 B1 | 7/2003 | Orus et al. |
| 6,591,249 B2 | 7/2003 | Zoka |
| 6,598,024 B1 | 7/2003 | Walker et al. |
| 6,601,622 B1 | 8/2003 | Young |
| 6,601,759 B2 | 8/2003 | Fife et al. |
| 6,601,762 B2 | 8/2003 | Pitrowski |
| 6,608,551 B1 | 8/2003 | Anderson et al. |
| 6,608,995 B1 | 8/2003 | Kawasaki et al. |
| 6,609,655 B1 | 8/2003 | Harrell |
| 6,609,656 B1 | 8/2003 | Elledge |
| 6,609,658 B1 * | 8/2003 | Sehr ............................... 235/384 |
| 6,623,039 B2 | 9/2003 | Thompson et al. |
| 6,626,356 B2 | 9/2003 | Davenport et al. |
| 6,628,961 B1 | 9/2003 | Ho et al. |
| 6,629,591 B1 | 10/2003 | Griswold et al. |
| 6,631,849 B2 | 10/2003 | Blossom |
| 6,636,620 B1 | 10/2003 | Hoshino |
| 6,636,833 B1 | 10/2003 | Flitcroft et al. |
| 6,644,551 B2 | 11/2003 | Clayman et al. |
| 6,650,887 B2 | 11/2003 | McGregor et al. |
| 6,651,168 B1 | 11/2003 | Kao et al. |
| 6,651,813 B2 | 11/2003 | Vallans et al. |
| 6,651,892 B2 | 11/2003 | Hooglander |
| 6,657,614 B1 | 12/2003 | Ito et al. |
| 6,662,166 B2 | 12/2003 | Pare, Jr. et al. |
| 6,665,405 B1 | 12/2003 | Lenstra |
| 6,669,086 B2 | 12/2003 | Abdi et al. |
| 6,671,358 B1 | 12/2003 | Seidman et al. |
| 6,674,786 B1 | 1/2004 | Nakamura et al. |
| 6,679,427 B1 | 1/2004 | Kuroiwa |
| 6,681,328 B1 | 1/2004 | Harris et al. |
| 6,681,926 B2 | 1/2004 | De Volpi |
| 6,684,269 B2 | 1/2004 | Wagner |
| 6,685,089 B2 | 2/2004 | Terranova et al. |
| 6,686,847 B1 | 2/2004 | Mittler |
| 6,687,714 B1 | 2/2004 | Kogen et al. |
| 6,687,875 B1 | 2/2004 | Suzuki |
| 6,690,930 B1 | 2/2004 | Dupre |
| 6,693,513 B2 | 2/2004 | Tuttle |
| 6,697,947 B1 | 2/2004 | Matyas, Jr. et al. |
| 6,697,971 B1 * | 2/2004 | Dwyer ............................... 714/54 |
| 6,703,918 B1 | 3/2004 | Kita |
| 6,704,039 B2 | 3/2004 | Pena |
| 6,704,608 B1 | 3/2004 | Azuma |
| 6,705,530 B2 | 3/2004 | Kiekhaefer |
| 6,708,375 B1 | 3/2004 | Johnson |
| 6,711,262 B1 | 3/2004 | Watanen |
| 6,725,202 B1 | 4/2004 | Hurta et al. |
| 6,732,919 B2 | 5/2004 | Macklin et al. |
| 6,732,936 B1 | 5/2004 | Kiekhaefer |
| 6,735,081 B1 | 5/2004 | Bishop et al. |
| 6,742,120 B1 | 5/2004 | Markakis et al. |
| 6,747,546 B1 | 6/2004 | Hikita et al. |
| 6,749,123 B2 | 6/2004 | Lasch et al. |
| 6,751,805 B1 | 6/2004 | Austion |

(56) References Cited

U.S. PATENT DOCUMENTS

| | | |
|---|---|---|
| 6,760,581 B2 | 7/2004 | Dutta |
| 6,763,500 B2 | 7/2004 | Black et al. |
| 6,764,014 B2 | 7/2004 | Lasch et al. |
| 6,765,470 B2 | 7/2004 | Shinzaki |
| 6,766,952 B2 | 7/2004 | Luu |
| 6,769,718 B1 | 8/2004 | Warther et al. |
| 6,771,981 B1 | 8/2004 | Zalewski et al. |
| 6,786,400 B1 | 9/2004 | Bucci |
| 6,789,012 B1 | 9/2004 | Childs et al. |
| 6,789,733 B2 | 9/2004 | Terranova et al. |
| 6,793,141 B1 | 9/2004 | Graham |
| 6,799,726 B2 | 10/2004 | Stockhammer |
| 6,816,058 B2 | 11/2004 | McGregor et al. |
| 6,819,219 B1 | 11/2004 | Bolle et al. |
| 6,823,910 B1 | 11/2004 | Elnekaveh |
| 6,830,193 B2 | 12/2004 | Tanaka |
| 6,834,270 B2 | 12/2004 | Pagani et al. |
| 6,834,795 B1 | 12/2004 | Rasmussen et al. |
| 6,842,106 B2 | 1/2005 | Hughes et al. |
| 6,843,415 B2 | 1/2005 | Vogler |
| 6,845,863 B1 | 1/2005 | Riley |
| 6,851,617 B2 | 2/2005 | Saint et al. |
| 6,853,087 B2 | 2/2005 | Neuhaus et al. |
| 6,853,894 B1 | 2/2005 | Kolls |
| 6,853,987 B1 | 2/2005 | Cook |
| 6,857,566 B2 | 2/2005 | Wankmueller |
| 6,859,672 B2 | 2/2005 | Roberts et al. |
| 6,873,974 B1 | 3/2005 | Schutzer |
| 6,877,097 B2 | 4/2005 | Hamid et al. |
| 6,883,715 B1 | 4/2005 | Fruhauf et al. |
| 6,895,310 B1 | 5/2005 | Kolls |
| 6,898,299 B1 | 5/2005 | Brooks |
| H2120 H | 7/2005 | Cudlitz |
| 6,914,517 B2 | 7/2005 | Kinsella |
| 6,915,277 B1 | 7/2005 | Manchester et al. |
| 6,920,560 B2 | 7/2005 | Wallace |
| 6,924,729 B1 | 8/2005 | Aschauer et al. |
| 6,925,439 B1 | 8/2005 | Pitroda |
| 6,925,565 B2 | 8/2005 | Black |
| 6,928,181 B2 | 8/2005 | Brooks |
| 6,931,538 B1 | 8/2005 | Sawaguchi |
| 6,934,861 B2 | 8/2005 | Haala |
| D509,243 S | 9/2005 | Hunter, Jr. et al. |
| 6,940,461 B2 | 9/2005 | Nantz et al. |
| 6,944,402 B1 | 9/2005 | Baker et al. |
| 6,944,768 B2 | 9/2005 | Siegel et al. |
| 6,959,874 B2 | 11/2005 | Bardwell |
| 6,961,448 B2 | 11/2005 | Nichols et al. |
| 6,970,583 B2 | 11/2005 | Black |
| 6,978,369 B2 | 12/2005 | Wheeler et al. |
| 6,978,933 B2 | 12/2005 | Yap et al. |
| 6,986,099 B2 | 1/2006 | Todd |
| 6,990,480 B1 | 1/2006 | Burt |
| 6,994,262 B1 | 2/2006 | Warther |
| 7,003,497 B2 | 2/2006 | Maes |
| 7,003,501 B2 | 2/2006 | Ostroff |
| 7,004,385 B1 | 2/2006 | Douglass |
| 7,006,993 B1 | 2/2006 | Cheong et al. |
| 7,049,962 B2 | 5/2006 | Atherton et al. |
| 7,051,925 B2 | 5/2006 | Schwarz, Jr. |
| 7,059,159 B2 | 6/2006 | Lanigan et al. |
| 7,068,148 B2 | 6/2006 | Shanks et al. |
| 7,069,444 B2 | 6/2006 | Lowensohn et al. |
| 7,070,112 B2 | 7/2006 | Beenau et al. |
| 7,093,767 B2 | 8/2006 | Faenza et al. |
| 7,096,204 B1 | 8/2006 | Chen et al. |
| 7,096,494 B1 | 8/2006 | Chen |
| 7,100,821 B2 | 9/2006 | Rasti |
| 7,102,523 B2 | 9/2006 | Shanks et al. |
| 7,103,575 B1 | 9/2006 | Linehan |
| 7,108,190 B2 | 9/2006 | Burgan et al. |
| 7,119,659 B2 | 10/2006 | Bonalle et al. |
| 7,127,672 B1 | 10/2006 | Patterson et al. |
| 7,131,574 B2 | 11/2006 | Sciupac et al. |
| 7,132,946 B2 | 11/2006 | Waldner et al. |
| 7,136,835 B1 | 11/2006 | Flitcroft et al. |
| 7,150,407 B1 | 12/2006 | Berger et al. |
| 7,154,375 B2 | 12/2006 | Beenau et al. |
| 7,171,662 B1 | 1/2007 | Misara et al. |
| 7,172,112 B2 | 2/2007 | Bonalle et al. |
| 7,184,747 B2 | 2/2007 | Bogat |
| 7,213,748 B2 | 5/2007 | Tsuei et al. |
| 7,237,121 B2 | 6/2007 | Cammack et al. |
| 7,239,226 B2 | 7/2007 | Berardi et al. |
| 7,254,557 B1 | 8/2007 | Gillin et al. |
| 7,281,135 B2 | 10/2007 | Black |
| 7,287,271 B1 | 10/2007 | Riggins |
| 7,287,695 B2 | 10/2007 | Wankmueller |
| 7,299,364 B2 | 11/2007 | Noble et al. |
| 7,303,120 B2 | 12/2007 | Beenau et al. |
| 7,314,164 B2 | 1/2008 | Bonalle et al. |
| 7,314,165 B2 | 1/2008 | Bonalle et al. |
| 7,318,550 B2 | 1/2008 | Bonalle et al. |
| 7,325,724 B2 | 2/2008 | Bonalle et al. |
| 7,341,181 B2 | 3/2008 | Bonalle et al. |
| 7,363,504 B2 | 4/2008 | Bonalle et al. |
| 7,363,505 B2 | 4/2008 | Black |
| 7,419,093 B1 | 9/2008 | Blackson et al. |
| 2001/0003071 A1 | 6/2001 | Mansutti et al. |
| 2001/0013542 A1 | 8/2001 | Horowitz et al. |
| 2001/0013546 A1 | 8/2001 | Ross |
| 2001/0013551 A1 | 8/2001 | Ramachandran |
| 2001/0017584 A1 | 8/2001 | Shinzaki |
| 2001/0018660 A1 | 8/2001 | Sehr |
| 2001/0022446 A1 | 9/2001 | Klure |
| 2001/0024157 A1 | 9/2001 | Hansmann et al. |
| 2001/0029493 A1 | 10/2001 | Pare et al. |
| 2001/0030238 A1 | 10/2001 | Arisawa |
| 2001/0032192 A1 | 10/2001 | Putta et al. |
| 2001/0034565 A1 | 10/2001 | Leatherman |
| 2001/0034623 A1* | 10/2001 | Chung .......................... 705/5 |
| 2001/0034720 A1 | 10/2001 | Armes et al. |
| 2001/0036301 A1 | 11/2001 | Yamaguchi et al. |
| 2001/0036835 A1 | 11/2001 | Leedom, Jr. |
| 2001/0039617 A1 | 11/2001 | Buhrlen et al. |
| 2001/0040507 A1 | 11/2001 | Eckstein et al. |
| 2001/0045469 A1 | 11/2001 | Hooglander |
| 2001/0049628 A1 | 12/2001 | Icho |
| 2001/0053239 A1 | 12/2001 | Takhar |
| 2001/0055411 A1 | 12/2001 | Black |
| 2002/0002468 A1 | 1/2002 | Spagna et al. |
| 2002/0005774 A1 | 1/2002 | Rudolph et al. |
| 2002/0011519 A1 | 1/2002 | Shults |
| 2002/0014529 A1 | 2/2002 | Tanaka |
| 2002/0014952 A1 | 2/2002 | Terranova |
| 2002/0016687 A1 | 2/2002 | Felsenstein et al. |
| 2002/0019807 A1 | 2/2002 | Halpern |
| 2002/0024590 A1 | 2/2002 | Pena |
| 2002/0026419 A1 | 2/2002 | Maritzen et al. |
| 2002/0026575 A1 | 2/2002 | Wheeler et al. |
| 2002/0028704 A1 | 3/2002 | Bloomfield et al. |
| 2002/0030579 A1 | 3/2002 | Albert et al. |
| 2002/0030581 A1 | 3/2002 | Janiak et al. |
| 2002/0035548 A1 | 3/2002 | Hogan et al. |
| 2002/0036237 A1 | 3/2002 | Atherton et al. |
| 2002/0038818 A1 | 4/2002 | Zingher et al. |
| 2002/0040935 A1 | 4/2002 | Weyant |
| 2002/0040936 A1 | 4/2002 | Wentker et al. |
| 2002/0041093 A1 | 4/2002 | Cox et al. |
| 2002/0042782 A1 | 4/2002 | Albazz et al. |
| 2002/0043566 A1 | 4/2002 | Goodman et al. |
| 2002/0046341 A1 | 4/2002 | Kazaks et al. |
| 2002/0052839 A1 | 5/2002 | Takatori |
| 2002/0062249 A1 | 5/2002 | Iannacci |
| 2002/0062284 A1 | 5/2002 | Kawan |
| 2002/0062291 A1 | 5/2002 | Zoka |
| 2002/0066784 A1 | 6/2002 | Segal et al. |
| 2002/0072349 A1 | 6/2002 | Geiselman et al. |
| 2002/0073025 A1 | 6/2002 | Tanner et al. |
| 2002/0074398 A1 | 6/2002 | Lancos et al. |
| 2002/0077837 A1 | 6/2002 | Krueger et al. |
| 2002/0077895 A1 | 6/2002 | Howell |
| 2002/0077992 A1 | 6/2002 | Tobin |
| 2002/0079367 A1 | 6/2002 | Montani |

(56) References Cited

U.S. PATENT DOCUMENTS

| | | |
|---|---|---|
| 2002/0083320 A1 | 6/2002 | Vatanen |
| 2002/0087869 A1 | 7/2002 | Kim |
| 2002/0090117 A1* | 7/2002 | Kramer .......... 382/124 |
| 2002/0092914 A1 | 7/2002 | Pentz et al. |
| 2002/0095298 A1 | 7/2002 | Ewing |
| 2002/0095343 A1 | 7/2002 | Barton et al. |
| 2002/0095389 A1 | 7/2002 | Gaines |
| 2002/0095587 A1 | 7/2002 | Doyle et al. |
| 2002/0095588 A1 | 7/2002 | Shigematsu et al. |
| 2002/0097142 A1 | 7/2002 | Janiak et al. |
| 2002/0097144 A1 | 7/2002 | Collins et al. |
| 2002/0099665 A1 | 7/2002 | Burger et al. |
| 2002/0107007 A1 | 8/2002 | Gerson |
| 2002/0107742 A1 | 8/2002 | Magill |
| 2002/0107791 A1 | 8/2002 | Nobrega et al. |
| 2002/0108062 A1 | 8/2002 | Nakajima et al. |
| 2002/0109580 A1 | 8/2002 | Shreve et al. |
| 2002/0111210 A1 | 8/2002 | Luciano, Jr. et al. |
| 2002/0111917 A1 | 8/2002 | Hoffman et al. |
| 2002/0111919 A1 | 8/2002 | Weller et al. |
| 2002/0112177 A1 | 8/2002 | Voltmer et al. |
| 2002/0113082 A1 | 8/2002 | Leatherman et al. |
| 2002/0116274 A1 | 8/2002 | Hind et al. |
| 2002/0120584 A1 | 8/2002 | Hogan et al. |
| 2002/0125164 A1 | 9/2002 | Bassinson |
| 2002/0126010 A1 | 9/2002 | Trimble et al. |
| 2002/0128977 A1 | 9/2002 | Nambiar et al. |
| 2002/0129248 A1 | 9/2002 | Wheeler et al. |
| 2002/0130186 A1 | 9/2002 | Lasch et al. |
| 2002/0130187 A1 | 9/2002 | Berg et al. |
| 2002/0131567 A1 | 9/2002 | Maginas |
| 2002/0133467 A1 | 9/2002 | Hobson et al. |
| 2002/0133725 A1 | 9/2002 | Roy et al. |
| 2002/0138351 A1 | 9/2002 | Houvener et al. |
| 2002/0138425 A1 | 9/2002 | Shimizu et al. |
| 2002/0138438 A1 | 9/2002 | Bardwell |
| 2002/0139839 A1 | 10/2002 | Catan |
| 2002/0140542 A1 | 10/2002 | Prokoski et al. |
| 2002/0145043 A1 | 10/2002 | Challa et al. |
| 2002/0147002 A1 | 10/2002 | Trop et al. |
| 2002/0147600 A1 | 10/2002 | Waters et al. |
| 2002/0147913 A1 | 10/2002 | Lun Yip |
| 2002/0148892 A1 | 10/2002 | Bardwell |
| 2002/0149467 A1 | 10/2002 | Calvesio et al. |
| 2002/0152123 A1 | 10/2002 | Giordano et al. |
| 2002/0153410 A1 | 10/2002 | Santini |
| 2002/0153424 A1 | 10/2002 | Li |
| 2002/0154795 A1 | 10/2002 | Lee et al. |
| 2002/0158747 A1 | 10/2002 | McGregor et al. |
| 2002/0163421 A1 | 11/2002 | Wang et al. |
| 2002/0165931 A1 | 11/2002 | Greer et al. |
| 2002/0166891 A1 | 11/2002 | Stoutenburg et al. |
| 2002/0166897 A1 | 11/2002 | Hooglander |
| 2002/0169673 A1 | 11/2002 | Prorock et al. |
| 2002/0174067 A1 | 11/2002 | Hoffman et al. |
| 2002/0175805 A9 | 11/2002 | Armstrong et al. |
| 2002/0176522 A1 | 11/2002 | Fan |
| 2002/0178063 A1 | 11/2002 | Gravelle et al. |
| 2002/0178124 A1 | 11/2002 | Lewis |
| 2002/0178369 A1 | 11/2002 | Black |
| 2002/0179704 A1 | 12/2002 | Deaton |
| 2002/0185543 A1 | 12/2002 | Pentz et al. |
| 2002/0186133 A1 | 12/2002 | Loof |
| 2002/0186838 A1 | 12/2002 | Brandys |
| 2002/0188501 A1 | 12/2002 | Lefkowith |
| 2002/0188854 A1 | 12/2002 | Heaven et al. |
| 2002/0188855 A1 | 12/2002 | Nakayama et al. |
| 2002/0190124 A1 | 12/2002 | Piotrowski |
| 2002/0190125 A1 | 12/2002 | Stockhammer |
| 2002/0191816 A1 | 12/2002 | Maritzen et al. |
| 2002/0192856 A1 | 12/2002 | Halope et al. |
| 2002/0193102 A1 | 12/2002 | Hyyppa et al. |
| 2002/0194137 A1 | 12/2002 | Park et al. |
| 2002/0194303 A1 | 12/2002 | Suila et al. |
| 2002/0194503 A1 | 12/2002 | Faith et al. |
| 2002/0196963 A1 | 12/2002 | Bardwell |
| 2003/0001006 A1 | 1/2003 | Lee |
| 2003/0001459 A1 | 1/2003 | Scott |
| 2003/0001755 A1 | 1/2003 | Tiernay et al. |
| 2003/0004866 A1 | 1/2003 | Huennekens et al. |
| 2003/0004881 A1 | 1/2003 | Shinzaki et al. |
| 2003/0005310 A1 | 1/2003 | Shinzaki |
| 2003/0006901 A1 | 1/2003 | Kim et al. |
| 2003/0009382 A1 | 1/2003 | Arbeloff et al. |
| 2003/0014307 A1 | 1/2003 | Heng |
| 2003/0014357 A1 | 1/2003 | Chrisekos et al. |
| 2003/0014891 A1 | 1/2003 | Nelms et al. |
| 2003/0018532 A1 | 1/2003 | Dudek et al. |
| 2003/0018567 A1 | 1/2003 | Flitcroft et al. |
| 2003/0018893 A1 | 1/2003 | Hess |
| 2003/0025600 A1 | 2/2003 | Blanchard |
| 2003/0028481 A1 | 2/2003 | Flitcroft et al. |
| 2003/0033697 A1 | 2/2003 | Hicks et al. |
| 2003/0037264 A1 | 2/2003 | Ezaki et al. |
| 2003/0037851 A1 | 2/2003 | Hogganvik |
| 2003/0046228 A1 | 3/2003 | Berney |
| 2003/0046237 A1 | 3/2003 | Uberti |
| 2003/0046540 A1 | 3/2003 | Nakamura et al. |
| 2003/0047482 A1 | 3/2003 | Jones et al. |
| 2003/0054836 A1 | 3/2003 | Michot |
| 2003/0055727 A1 | 3/2003 | Walker et al. |
| 2003/0057226 A1 | 3/2003 | Long |
| 2003/0057278 A1 | 3/2003 | Wong |
| 2003/0061172 A1 | 3/2003 | Robinson |
| 2003/0069828 A1 | 4/2003 | Blazey et al. |
| 2003/0069846 A1 | 4/2003 | Marcon |
| 2003/0074317 A1 | 4/2003 | Hofi |
| 2003/0086591 A1 | 5/2003 | Simon |
| 2003/0093187 A1 | 5/2003 | Walker |
| 2003/0097344 A1 | 5/2003 | Chaum et al. |
| 2003/0106935 A1 | 6/2003 | Burchette, Jr. |
| 2003/0112120 A1 | 6/2003 | K. |
| 2003/0112972 A1 | 6/2003 | Hattick et al. |
| 2003/0115126 A1 | 6/2003 | Pitroda |
| 2003/0120554 A1 | 6/2003 | Hogan et al. |
| 2003/0120626 A1 | 6/2003 | Piotrowski |
| 2003/0121969 A1 | 7/2003 | Wankmueller |
| 2003/0122120 A1 | 7/2003 | Brazis et al. |
| 2003/0123714 A1 | 7/2003 | O'Gorman et al. |
| 2003/0124294 A1 | 7/2003 | Hodson et al. |
| 2003/0125054 A1 | 7/2003 | Garcia |
| 2003/0130820 A1 | 7/2003 | Lane, III |
| 2003/0132132 A1 | 7/2003 | Small |
| 2003/0132284 A1 | 7/2003 | Reynolds et al. |
| 2003/0132297 A1 | 7/2003 | McCall et al. |
| 2003/0140228 A1 | 7/2003 | Binder |
| 2003/0149661 A1 | 8/2003 | Mitchell et al. |
| 2003/0149662 A1 | 8/2003 | Shore |
| 2003/0150911 A1 | 8/2003 | Joseph |
| 2003/0152252 A1 | 8/2003 | Kondo et al. |
| 2003/0153356 A1 | 8/2003 | Liu |
| 2003/0155416 A1 | 8/2003 | Macklin et al. |
| 2003/0159044 A1 | 8/2003 | Doyle et al. |
| 2003/0160074 A1 | 8/2003 | Pineda |
| 2003/0163699 A1 | 8/2003 | Pailles et al. |
| 2003/0167207 A1 | 9/2003 | Berardi et al. |
| 2003/0173408 A1 | 9/2003 | Mosher, Jr. et al. |
| 2003/0177102 A1 | 9/2003 | Robinson |
| 2003/0177347 A1 | 9/2003 | Schneier et al. |
| 2003/0178495 A1 | 9/2003 | Jones et al. |
| 2003/0183689 A1 | 10/2003 | Swift et al. |
| 2003/0183695 A1 | 10/2003 | Labrec et al. |
| 2003/0183699 A1 | 10/2003 | Masui |
| 2003/0187786 A1 | 10/2003 | Swift et al. |
| 2003/0187787 A1 | 10/2003 | Freund |
| 2003/0187790 A1 | 10/2003 | Swift et al. |
| 2003/0187796 A1 | 10/2003 | Swift et al. |
| 2003/0191949 A1 | 10/2003 | Odagawa |
| 2003/0195037 A1 | 10/2003 | Vuong et al. |
| 2003/0195842 A1 | 10/2003 | Reece |
| 2003/0195843 A1 | 10/2003 | Matsuda et al. |
| 2003/0197593 A1 | 10/2003 | Siegel et al. |
| 2003/0200184 A1 | 10/2003 | Dominguez et al. |
| 2003/0208439 A1 | 11/2003 | Rast |

(56) References Cited

U.S. PATENT DOCUMENTS

| | | |
|---|---|---|
| 2003/0218066 A1 | 11/2003 | Fernandes et al. |
| 2003/0220876 A1 | 11/2003 | Burger et al. |
| 2003/0222153 A1 | 12/2003 | Pentz et al. |
| 2003/0223625 A1 | 12/2003 | Hillhouse et al. |
| 2003/0225623 A1 | 12/2003 | Wankmueller |
| 2003/0225713 A1 | 12/2003 | Atkinson et al. |
| 2003/0226041 A1 | 12/2003 | Palmer et al. |
| 2003/0227550 A1 | 12/2003 | Manico et al. |
| 2003/0229793 A1 | 12/2003 | McCall et al. |
| 2003/0230514 A1 | 12/2003 | Baker |
| 2003/0233334 A1 | 12/2003 | Smith |
| 2003/0236704 A1 | 12/2003 | Antonucci |
| 2004/0006497 A1 | 1/2004 | Nestor et al. |
| 2004/0006539 A1 | 1/2004 | Royer et al. |
| 2004/0010462 A1 | 1/2004 | Moon et al. |
| 2004/0011877 A1 | 1/2004 | Reppermund |
| 2004/0014457 A1 | 1/2004 | Stevens |
| 2004/0015451 A1 | 1/2004 | Sahota et al. |
| 2004/0016796 A1 | 1/2004 | Hanna et al. |
| 2004/0017934 A1 | 1/2004 | Kocher |
| 2004/0019494 A1 | 1/2004 | Ridgeway et al. |
| 2004/0019564 A1 | 1/2004 | Goldthwaite et al. |
| 2004/0020982 A1 | 2/2004 | Hoffman et al. |
| 2004/0021552 A1 | 2/2004 | Koo |
| 2004/0024694 A1 | 2/2004 | Lawrence et al. |
| 2004/0026518 A1 | 2/2004 | Kudo et al. |
| 2004/0029569 A1 | 2/2004 | Khan et al. |
| 2004/0030601 A1 | 2/2004 | Pond et al. |
| 2004/0031856 A1 | 2/2004 | Atsmon et al. |
| 2004/0039814 A1 | 2/2004 | Crabtree et al. |
| 2004/0039860 A1 | 2/2004 | Mills et al. |
| 2004/0041021 A1 | 3/2004 | Nugent, Jr. |
| 2004/0041690 A1 | 3/2004 | Yamagishi |
| 2004/0044627 A1 | 3/2004 | Russell et al. |
| 2004/0046034 A1 | 3/2004 | Ey Yamani et al. |
| 2004/0049687 A1 | 3/2004 | Orsini |
| 2004/0050930 A1 | 3/2004 | Rowe |
| 2004/0052406 A1 | 3/2004 | Brooks |
| 2004/0059923 A1 | 3/2004 | ShamRao |
| 2004/0061593 A1 | 4/2004 | Lane |
| 2004/0062423 A1 | 4/2004 | Doi |
| 2004/0073792 A1 | 4/2004 | Noble et al. |
| 2004/0083184 A1 | 4/2004 | Tsuei et al. |
| 2004/0083380 A1 | 4/2004 | Janke |
| 2004/0084524 A1 | 5/2004 | Ramachandran |
| 2004/0089724 A1 | 5/2004 | Lasch et al. |
| 2004/0098336 A1 | 5/2004 | Flink |
| 2004/0104266 A1 | 6/2004 | Bolle et al. |
| 2004/0104268 A1 | 6/2004 | Bailey |
| 2004/0118930 A1 | 6/2004 | Berardi et al. |
| 2004/0124104 A1 | 7/2004 | DeVolpi |
| 2004/0124246 A1 | 7/2004 | Allen et al. |
| 2004/0127256 A1 | 7/2004 | Goldthwaite et al. |
| 2004/0129787 A1 | 7/2004 | Saito et al. |
| 2004/0131237 A1 | 7/2004 | Machida |
| 2004/0133787 A1 | 7/2004 | Doughty et al. |
| 2004/0136573 A1 | 7/2004 | Sato |
| 2004/0139021 A1 | 7/2004 | Reed et al. |
| 2004/0144841 A1 | 7/2004 | Tsukamoto et al. |
| 2004/0144846 A1 | 7/2004 | Lasch et al. |
| 2004/0149820 A1 | 8/2004 | Zuili |
| 2004/0155101 A1 | 8/2004 | Royer et al. |
| 2004/0158723 A1 | 8/2004 | Root |
| 2004/0160310 A1 | 8/2004 | Chen et al. |
| 2004/0161135 A1 | 8/2004 | Sano et al. |
| 2004/0165753 A1 | 8/2004 | Takhiri et al. |
| 2004/0169071 A1 | 9/2004 | Burgan et al. |
| 2004/0172541 A1 | 9/2004 | Ando et al. |
| 2004/0176071 A1 | 9/2004 | Gehrmann et al. |
| 2004/0177045 A1 | 9/2004 | Brown |
| 2004/0180657 A1 | 9/2004 | Yaqub et al. |
| 2004/0188519 A1 | 9/2004 | Cassone |
| 2004/0190757 A1 | 9/2004 | Murphy et al. |
| 2004/0193676 A1 | 9/2004 | Marks |
| 2004/0195314 A1 | 10/2004 | Lee |
| 2004/0199469 A1 | 10/2004 | Barillova et al. |
| 2004/0202354 A1 | 10/2004 | Togino |
| 2004/0208343 A1 | 10/2004 | Golden et al. |
| 2004/0215575 A1 | 10/2004 | Garrity |
| 2004/0222803 A1 | 11/2004 | Tartagni |
| 2004/0230488 A1 | 11/2004 | Beenau et al. |
| 2004/0232220 A1 | 11/2004 | Beenau et al. |
| 2004/0232224 A1 | 11/2004 | Beenau et al. |
| 2004/0233039 A1 | 11/2004 | Beenau et al. |
| 2004/0235450 A1 | 11/2004 | Rosenberg |
| 2004/0236680 A1* | 11/2004 | Luoffo et al. .................. 705/39 |
| 2004/0236699 A1 | 11/2004 | Beenau et al. |
| 2004/0236700 A1 | 11/2004 | Beenau et al. |
| 2004/0236701 A1 | 11/2004 | Beenau et al. |
| 2004/0236819 A1 | 11/2004 | Anati et al. |
| 2004/0239480 A1 | 12/2004 | Beenau et al. |
| 2004/0240711 A1 | 12/2004 | Hamza et al. |
| 2004/0255168 A1 | 12/2004 | Murashita et al. |
| 2004/0257196 A1 | 12/2004 | Kotzin |
| 2004/0258282 A1 | 12/2004 | Bjorn et al. |
| 2005/0001711 A1 | 1/2005 | Doughty et al. |
| 2005/0004921 A1 | 1/2005 | Beenau et al. |
| 2005/0005172 A1 | 1/2005 | Haala |
| 2005/0011776 A1 | 1/2005 | Nagel |
| 2005/0017068 A1 | 1/2005 | Zalewski et al. |
| 2005/0018658 A1 | 1/2005 | Ikeda et al. |
| 2005/0020304 A1 | 1/2005 | Shinzaki |
| 2005/0021457 A1 | 1/2005 | Johnson et al. |
| 2005/0023157 A1 | 2/2005 | Logan |
| 2005/0033686 A1 | 2/2005 | Peart et al. |
| 2005/0033687 A1 | 2/2005 | Beenau et al. |
| 2005/0033689 A1 | 2/2005 | Bonalle et al. |
| 2005/0033992 A1 | 2/2005 | Inabe |
| 2005/0035192 A1 | 2/2005 | Bonalle et al. |
| 2005/0035847 A1 | 2/2005 | Bonalle et al. |
| 2005/0036665 A1 | 2/2005 | Higuchi |
| 2005/0038718 A1 | 2/2005 | Barnes et al. |
| 2005/0040221 A1 | 2/2005 | Schwarz, Jr. |
| 2005/0040272 A1 | 2/2005 | Argumedo et al. |
| 2005/0045718 A1 | 3/2005 | Bortolin et al. |
| 2005/0050367 A1 | 3/2005 | Burger et al. |
| 2005/0054438 A1 | 3/2005 | Rothschild et al. |
| 2005/0058262 A1 | 3/2005 | Timmins et al. |
| 2005/0060233 A1 | 3/2005 | Bonalle et al. |
| 2005/0065842 A1 | 3/2005 | Summers |
| 2005/0065872 A1 | 3/2005 | Moebs et al. |
| 2005/0071231 A1 | 3/2005 | Beenau et al. |
| 2005/0087597 A1 | 4/2005 | Gotfried et al. |
| 2005/0091325 A1 | 4/2005 | Kuwana et al. |
| 2005/0097038 A1 | 5/2005 | Yu et al. |
| 2005/0098621 A1 | 5/2005 | deSylva |
| 2005/0100199 A1 | 5/2005 | Boshra |
| 2005/0102524 A1 | 5/2005 | Haala |
| 2005/0103839 A1 | 5/2005 | Hewel |
| 2005/0109836 A1 | 5/2005 | Ben-Aissa |
| 2005/0113137 A1 | 5/2005 | Rodriguez et al. |
| 2005/0116024 A1 | 6/2005 | Beenau et al. |
| 2005/0119978 A1 | 6/2005 | Ates |
| 2005/0121512 A1 | 6/2005 | Wankmueller |
| 2005/0122209 A1 | 6/2005 | Black |
| 2005/0123137 A1 | 6/2005 | McCallum |
| 2005/0125312 A1 | 6/2005 | Dearing et al. |
| 2005/0125317 A1 | 6/2005 | Winkelman, III et al. |
| 2005/0125343 A1 | 6/2005 | Mendelovich |
| 2005/0127164 A1 | 6/2005 | Wankmueller |
| 2005/0137977 A1 | 6/2005 | Wankmueller |
| 2005/0139021 A1 | 6/2005 | Arnouse |
| 2005/0144133 A1 | 6/2005 | Hoffman et al. |
| 2005/0149358 A1* | 7/2005 | Sacco et al. .................. 705/2 |
| 2005/0149926 A1 | 7/2005 | Saltz |
| 2005/0160271 A9 | 7/2005 | Brundage et al. |
| 2005/0160790 A1 | 7/2005 | Tanaka et al. |
| 2005/0165684 A1 | 7/2005 | Jensen et al. |
| 2005/0166062 A1 | 7/2005 | Sanchez-Cifuentes |
| 2005/0169504 A1 | 8/2005 | Black |
| 2005/0171787 A1 | 8/2005 | Zagami |
| 2005/0171905 A1 | 8/2005 | Wankmueller |
| 2005/0180618 A1 | 8/2005 | Black |
| 2005/0187883 A1 | 8/2005 | Bishop et al. |

(56) References Cited

U.S. PATENT DOCUMENTS

| | | |
|---|---|---|
| 2005/0187916 A1 | 8/2005 | Levin et al. |
| 2005/0197923 A1 | 9/2005 | Kilner et al. |
| 2005/0203857 A1 | 9/2005 | Friedman |
| 2005/0207002 A1 | 9/2005 | Liu et al. |
| 2005/0211784 A1 | 9/2005 | Justin |
| 2005/0212657 A1 | 9/2005 | Simon |
| 2005/0216424 A1 | 9/2005 | Gandre et al. |
| 2005/0221853 A1 | 10/2005 | Silvester |
| 2005/0223230 A1 | 10/2005 | Zick |
| 2005/0232471 A1 | 10/2005 | Baer |
| 2005/0240778 A1 | 10/2005 | Saito |
| 2005/0246292 A1 | 11/2005 | Sarcanin |
| 2005/0251688 A1 | 11/2005 | Nanavati et al. |
| 2005/0261972 A1 | 11/2005 | Black |
| 2005/0275505 A1 | 12/2005 | Himmelstein |
| 2005/0278222 A1 | 12/2005 | Northrup |
| 2006/0000892 A1 | 1/2006 | Bonalle et al. |
| 2006/0000893 A1 | 1/2006 | Bonalle et al. |
| 2006/0000894 A1 | 1/2006 | Bonalle et al. |
| 2006/0000895 A1 | 1/2006 | Bonalle et al. |
| 2006/0000896 A1 | 1/2006 | Bonalle et al. |
| 2006/0000897 A1 | 1/2006 | Bonalle et al. |
| 2006/0000898 A1 | 1/2006 | Bonalle et al. |
| 2006/0000899 A1 | 1/2006 | Bonalle et al. |
| 2006/0005022 A1 | 1/2006 | Wakamori et al. |
| 2006/0005042 A1 | 1/2006 | Black |
| 2006/0016868 A1 | 1/2006 | Bonalle et al. |
| 2006/0016869 A1 | 1/2006 | Bonalle et al. |
| 2006/0016871 A1 | 1/2006 | Bonalle et al. |
| 2006/0016874 A1 | 1/2006 | Bonalle et al. |
| 2006/0016875 A1 | 1/2006 | Bonalle et al. |
| 2006/0016877 A1 | 1/2006 | Bonalle et al. |
| 2006/0033609 A1 | 2/2006 | Bridgelall |
| 2006/0034492 A1 | 2/2006 | Siegel et al. |
| 2006/0066444 A1 | 3/2006 | Steeves |
| 2006/0069635 A1 | 3/2006 | Ram et al. |
| 2006/0071756 A1 | 4/2006 | Steeves |
| 2006/0077034 A1 | 4/2006 | Hillier |
| 2006/0080552 A1 | 4/2006 | Lauper |
| 2006/0095369 A1 | 5/2006 | Hofi |
| 2006/0104485 A1 | 5/2006 | Miller et al. |
| 2006/0123240 A1 | 6/2006 | Chaiken |
| 2006/0136336 A1 | 6/2006 | Drummond et al. |
| 2006/0156395 A1 | 7/2006 | Fontaine |
| 2006/0158434 A1 | 7/2006 | Zank et al. |
| 2006/0173291 A1 | 8/2006 | Glossop |
| 2006/0173791 A1 | 8/2006 | Mann et al. |
| 2006/0177061 A1 | 8/2006 | Orsini et al. |
| 2006/0178937 A1 | 8/2006 | Rau et al. |
| 2006/0190419 A1 | 8/2006 | Bunn et al. |
| 2006/0202835 A1 | 9/2006 | Thibault |
| 2006/0208066 A1 | 9/2006 | Finn et al. |
| 2006/0213986 A1 | 9/2006 | Register et al. |
| 2006/0229988 A1 | 10/2006 | Oshima et al. |
| 2006/0237528 A1 | 10/2006 | Bishop et al. |
| 2006/0242423 A1 | 10/2006 | Kussmaul |
| 2006/0278723 A1 | 12/2006 | Dan et al. |
| 2007/0008131 A1 | 1/2007 | Doan et al. |
| 2007/0046468 A1 | 3/2007 | Davis |
| 2007/0057797 A1 | 3/2007 | Waldner et al. |
| 2007/0075841 A1 | 4/2007 | Maltsev et al. |
| 2007/0112957 A1 | 5/2007 | Shastri et al. |
| 2007/0119924 A1 | 5/2007 | Register et al. |
| 2007/0241861 A1 | 10/2007 | Venkatanna et al. |
| 2007/0252001 A1 | 11/2007 | Kail et al. |
| 2007/0252010 A1 | 11/2007 | Gonzalez et al. |
| 2007/0284432 A1 | 12/2007 | Abouyounes |
| 2007/0296544 A1 | 12/2007 | Beenau et al. |
| 2007/0296551 A1 | 12/2007 | Beenau et al. |
| 2007/0299782 A1 | 12/2007 | Beenau et al. |
| 2007/0299783 A1 | 12/2007 | Beenau et al. |
| 2008/0006691 A1 | 1/2008 | Bonalle et al. |
| 2008/0008359 A1 | 1/2008 | Beenau et al. |
| 2008/0008363 A1 | 1/2008 | Bonalle et al. |
| 2008/0010214 A1 | 1/2008 | Bonalle et al. |
| 2008/0011830 A1 | 1/2008 | Bonalle et al. |
| 2008/0011831 A1 | 1/2008 | Bonalle et al. |
| 2008/0013796 A1 | 1/2008 | Bonalle et al. |
| 2008/0013807 A1 | 1/2008 | Bonalle et al. |
| 2008/0015941 A1 | 1/2008 | Beenau et al. |
| 2008/0015992 A1 | 1/2008 | Bonalle et al. |
| 2008/0015993 A1 | 1/2008 | Bonalle et al. |
| 2008/0015994 A1 | 1/2008 | Bonalle et al. |
| 2008/0016002 A1 | 1/2008 | Beenau et al. |
| 2008/0033722 A1 | 2/2008 | Beenau et al. |
| 2008/0067242 A1 | 3/2008 | Bonalle et al. |
| 2008/0072065 A1 | 3/2008 | Bonalle et al. |

FOREIGN PATENT DOCUMENTS

| | | |
|---|---|---|
| DE | 2847756 | 5/1980 |
| DE | 29702538 | 4/1997 |
| EP | 0181770 | 5/1986 |
| EP | 0343829 | 11/1989 |
| EP | 0354817 | 2/1990 |
| EP | 0 358 525 A2 | 3/1990 |
| EP | 0368570 | 5/1990 |
| EP | 0388090 | 9/1990 |
| EP | 0 424 726 A1 | 10/1990 |
| EP | 0403134 | 12/1990 |
| EP | 0411602 | 2/1991 |
| EP | 0473998 | 3/1992 |
| EP | 0481388 | 4/1992 |
| EP | 0531605 | 3/1993 |
| EP | 0552047 | 7/1993 |
| EP | 0560318 | 9/1993 |
| EP | 0568185 | 11/1993 |
| EP | 0657297 | 6/1995 |
| EP | 0721850 | 7/1996 |
| EP | 0780839 | 6/1997 |
| EP | 0789316 | 8/1997 |
| EP | 0866420 | 9/1998 |
| EP | 0894620 | 2/1999 |
| EP | 0916519 | 5/1999 |
| EP | 0 933 717 A2 | 8/1999 |
| EP | 0949595 | 10/1999 |
| EP | 0 956 818 A1 | 11/1999 |
| EP | 0 959 440 A2 | 11/1999 |
| EP | 0 984 404 A2 | 3/2000 |
| EP | 1 016 947 A2 | 7/2000 |
| EP | 1 039 403 A2 | 9/2000 |
| EP | 1 104 909 A2 | 6/2001 |
| EP | 1 113 387 A2 | 7/2001 |
| EP | 1 199 684 A2 | 4/2002 |
| EP | 1 251 450 A1 | 10/2002 |
| EP | 1345146 | 9/2003 |
| GB | 1371254 | 10/1974 |
| GB | 2108906 | 5/1985 |
| GB | 2240948 | 8/1991 |
| GB | 2 347 537 A | 9/2000 |
| GB | 2350021 | 11/2000 |
| JP | 62-043774 | 3/1987 |
| JP | 62-264999 | 11/1987 |
| JP | 63-071794 | 4/1988 |
| JP | 63-098689 | 4/1988 |
| JP | 63-072721 | 5/1988 |
| JP | 63-175987 | 7/1988 |
| JP | 64-004934 | 1/1989 |
| JP | 64-037397 | 3/1989 |
| JP | 64-087395 | 3/1989 |
| JP | 64-087396 | 3/1989 |
| JP | 02-130737 | 5/1990 |
| JP | 02-252149 | 10/1990 |
| JP | 03-290780 | 12/1991 |
| JP | 42-005596 | 7/1992 |
| JP | 04-303692 | 10/1992 |
| JP | 05-069689 | 3/1993 |
| JP | 05-254283 | 10/1993 |
| JP | 06-183187 | 7/1994 |
| JP | 06-191137 | 7/1994 |
| JP | 06-234287 | 8/1994 |
| JP | 07-173358 | 7/1995 |
| JP | 07-205569 | 8/1995 |
| JP | 08-244385 | 9/1996 |

(56) References Cited

FOREIGN PATENT DOCUMENTS

| | | |
|---|---|---|
| JP | 08-324163 | 12/1996 |
| JP | 09-050505 | 2/1997 |
| JP | 09-052240 | 2/1997 |
| JP | 09-274640 | 10/1997 |
| JP | 10-129161 | 5/1998 |
| JP | 10-289296 | 10/1998 |
| JP | 10302160 | 11/1998 |
| JP | 10-334206 | 12/1998 |
| JP | 10-340231 | 12/1998 |
| JP | 11-175640 | 7/1999 |
| JP | 11-227367 | 8/1999 |
| JP | 11-353425 | 12/1999 |
| JP | 2000-1109 A | 1/2000 |
| JP | 2000-015288 A | 1/2000 |
| JP | 2000-40181 A | 2/2000 |
| JP | 2000-048153 | 2/2000 |
| JP | 2000-67312 A | 3/2000 |
| JP | 2000-163538 | 6/2000 |
| JP | 2000-177229 | 6/2000 |
| JP | 2000-194799 | 7/2000 |
| JP | 2000-207641 A | 7/2000 |
| JP | 2000-222176 | 8/2000 |
| JP | 2000-252854 | 9/2000 |
| JP | 2001-5931 A | 1/2001 |
| JP | 2001-504406 | 4/2001 |
| JP | 2001-134536 | 5/2001 |
| JP | 2001-160105 | 6/2001 |
| JP | 2001-283122 A | 10/2001 |
| JP | 2001-315475 | 11/2001 |
| JP | 2002-109584 | 4/2002 |
| JP | 2002-133335 | 5/2002 |
| JP | 2002-157530 | 5/2002 |
| JP | 2002-274087 | 9/2002 |
| JP | 2003-288646 | 10/2003 |
| WO | WO 81/00776 | 3/1981 |
| WO | WO 89/03760 | 5/1989 |
| WO | WO 90/08661 | 8/1990 |
| WO | WO 92/16913 | 10/1992 |
| WO | WO 95/32919 A1 | 12/1995 |
| WO | WO 95/35546 | 12/1995 |
| WO | WO 96/18972 | 6/1996 |
| WO | WO 97/40459 | 10/1997 |
| WO | WO 99/03057 A1 | 1/1999 |
| WO | WO 99/12136 | 3/1999 |
| WO | WO 99/14055 | 3/1999 |
| WO | WO 99/27492 | 6/1999 |
| WO | WO 99/40548 | 8/1999 |
| WO | WO 99/47983 | 9/1999 |
| WO | WO 00/10144 A1 | 2/2000 |
| WO | WO 00/38088 A1 | 6/2000 |
| WO | WO 01/04825 A1 | 1/2001 |
| WO | WO 01/15098 A1 | 3/2001 |
| WO | WO 01/43095 A2 | 6/2001 |
| WO | WO 01/55955 | 8/2001 |
| WO | WO 01/72224 A1 | 10/2001 |
| WO | WO 01/77856 A1 | 10/2001 |
| WO | WO 01/80473 A2 | 10/2001 |
| WO | WO 01/86535 A1 | 11/2001 |
| WO | WO 01/90962 A1 | 11/2001 |
| WO | WO 01/95243 A2 | 12/2001 |
| WO | WO 02/01485 A1 | 1/2002 |
| WO | WO 02/13134 A2 | 2/2002 |
| WO | WO 02/21903 A1 | 3/2002 |
| WO | WO 02/063545 A2 | 8/2002 |
| WO | WO 02/065246 A2 | 8/2002 |
| WO | WO 02/065404 A2 | 8/2002 |
| WO | WO 02/069221 A1 | 9/2002 |
| WO | WO 02/073512 A1 | 9/2002 |
| WO | WO 02/086665 A2 | 10/2002 |
| WO | WO 02/091281 A2 | 11/2002 |
| WO | WO 02/097575 A2 | 12/2002 |
| WO | WO 02/101670 A2 | 12/2002 |
| WO | WO 03/007623 | 1/2003 |

OTHER PUBLICATIONS

"Physical Reality: A Second Look", Ken Sharp, Senior Technical Editor, http://www.idsystems.com/reader/1999_03/phys0399_pt2/phys0399_pt2.htm (6 pages).

"'Magic Wands' to Speed Mobile Sales", Bob Brewin, Jan. 15, 2001, http://www.computerworld.com/mobiletopics/mobile/story/1,10801,563300.html (4 pages).

"Mobile Speedpass Goes Global as Mobil Singapore Rolls Out Asia's First RFID-Based Pay-At-The-Pump System", Press Release, Apr. 5, 1999, http://www.ti.com/tiris/docs/news_releases/rel12.htm (3 pages).

"Speedpass Unleashed", Jun. 4, 2002 http://www.cardweb.com/cardtrak/news/cf2_20a_97.html (2 pages).

Prophecy Central Update #9, Oct. 10, 1997, http://www.bible-prophecy.com/pcu9.htm (5 pages).

International Newsletter of the TI RFID Group, Issue 20, 2000 (12 pages).

"CES: Microsoft's SPOT Technology has Humble Origins", by James Niccolai, Jan. 10, 2003, http://archive.inforworld.com/articles/hn/xml/03/01/10/030110hnspot.xml?s=IDGNS (3 pages).

"Microsoft: See SPOT Run on Your Wrist", by Richard Shim, Jun. 5, 2003, http://news.com.com/2100-1041_3-1013442.html?tag=fd_top (1 page).

"Networking: Microsoft SPOT", by Jeremy A. Kaplan, Jul. 1, 2003, http://www.pcmag.com/print_article/0,3048,a=43561,00.asp (2 pages).

"Microsoft Launches Smart Personal Object Technology Initiative", Press Release from COMDEX Fall 2002, Nov. 17, 2002, http://www.Microsoft.com/presspass/features/2002/nov02/11-17SPOT.asp (4 pages).

http://www.semiconductors.phillips.com/news/content/file_878.html, Apr. 7, 2003.

http://www.palowireless.com/infotooth/whatis.asp, Apr. 28, 2003.

http://www.palowireless.com/infotooth/tutorial.asp, Apr. 28, 2003.

http://www.palowireless.com/infotooth/tutorial/profiles.asp, Apr. 28, 2003.

http://www.palowireless.com/infotooth/tutorial/radio.asp, Apr. 28, 2003.

http://www.polowireless.com/infotooth/tutorial/baseband.asp, Apr. 28, 2003.

http://www.palowireless.com/infotooth/tutorial/lmp.asp, Apr. 28, 2003.

http://www.palowireless.com/infotooth/tutorial/hci.asp, Apr. 28, 2003.

http://www.palowireless.com/infotooth/tutorial/l2cap.asp, Apr. 28, 2003.

http://www.palowireless.com/infotooth/tutorial/rfcomm.asp, Apr. 28, 2003.

http://www.palowireless.com/infotooth/tutorial/sdp.asp, Apr. 28, 2003.

http://www.palowireless.com/infotooth/tutorialk1_gap.asp, Apr. 28, 2003.

"Sony, Phillips to Test RFID Platform", RFID Journal, May 8, 2003.

ISO/IEC 7816-6:1996(E)—First Edition—May 15, 1996.

ISO/IEC 7816-4:1995(E)—First Edition—Sep. 1, 1995.

USBanker, Article 5, 1995, http://www.banking.com/us-banker/art5.

Financial Technology International Bulletin, V14, n1, p. 4, Sep. 1996.

Green, Thomas C., "American Express Offers temporary CC numbers for the web," Sep. 9, 2000, The Register, www.theregister.c.uk/c.

CNN.com, U.S. News, "American Express to offer disposable credit card numbers," Sep. 8, 2000, Associated Press, www.cnn.com.

American Express, "Private Payments (sm); A New Level of Security from American Express," American Express Website, Cards.

Martin Zack, "One-Time Nos. Stop Web Hackers From Pilfering Data," Jan. 2001, Card Marketing, Thomson Financial, www.c rdf rum.c.

The Dollar Stretcher, "Disposable Credit Card Numbers," Jan. 2001, CardRatings.org, www.stretcher.com.

Canadian Office Action dated Apr. 25, 2008.

(56) References Cited

OTHER PUBLICATIONS

International Search Report and Written Opinion of the International Searching Authority, PCT/US05/26067, May 23, 2007.
"What's New: Timex Watch Features Speedpass System" http://www.speedpass.com/news/article.jsp?id=51 (1 page).
"'Magic Wands' to Speed Mobile Sales", BobBrewin, Jan. 15, 2001, http://www.computerworld.com/mobiletopics/mobile/story/1,10801,563300.html (4 pages).
"Mobile Speedpass Goes Global as Mobil Singapore Rolls Out Asia's First RFID-Based Pay-At-The-Pump System", Press Release, Apr. 5, 1999, http://www.ti.com/tiris/docs/news_releases/re112.htm (3 pages).
"Bank Extends RFID Payment Pilot: Bank of America will continue to test its QuickWave RFID payment card for another three months", RFID Journal, Jan. 23, 2003.
"MasterCard to Test RFID Card: Pilot will test whether consumers, merchants and credit card issuers value "contactless" payments", RFID Journal, Dec. 20, 2002.
"Vendors Target Amusement Parks: Protecting children and enabling cashless payments make RFID an appealing option for the entertainment industry", RFID Journal, Nov. 27, 2002.
"Inside's Next-Gen Smart Card: The French company plans to introduce an RFID card that uses a 16-bit microprocessor and new encryption technology", RFID Journal, Oct. 29, 2002.
"Sony, Philips Creating RFID Link: Consumer electronics giants are jointly developing a new RFID standard for payments and for communication between devices", RFID Journal, Sep. 17, 2002.
"Japan Gets Digital Ticket System: A national ticket seller and phone company are teaming up to create an electronic ticket", RFID Journal, Aug. 31, 2002.
"Security for Wireless Java: NTRU, a startup that offers security software, has relased of Java version of its NTRU encryption algorithm", RFID Journal, Jun. 27, 2002.
"Making RFID Payments Ubiquitous: Philips and Visa want people to be able to pay for goods and services anywhere by using RFID chips embedded in the phones and other devices", RFID Journal, Jun. 2, 20003.
"RFID Smart Cards Gain Ground: The convenience of contactless transactions is driving widespread adoption of contactless smart cards", RFID Journal, Apr. 9, 2003.
"TI Embarces Prox Card Standard: Texas Instruments ISO 14443 payment platform promises faster data transfer rates and more security", RFID Journal, Mar. 6, 2003.
"Multiple Frequency Transponders: Volume production of dual-band RFID chips begins", Frontline Solutions, Jul. 16, 2003.
Functional Specification, Standard Card IC MFI IC S50, Philips Semiconductors, Product Specification Rev. 5.1 May 2001.

* cited by examiner

\*\*\* Track 2 Layout: \*\*\* | SS | PAN | FS | Additional Data | ES | LRC |

FIG. 17

\*\*\*MasterCard Track Layout in Track 2\*\*\*

| SS | PAN | FS | ADDITIONAL DATA | ES | LRC |

;3111222233334444=9912101000000000000?

FIG. 18

RF TRANSACTION SYSTEM AND METHOD FOR STORING USER PERSONAL DATA

CROSS-REFERENCE TO RELATED APPLICATIONS

This application (the "'964 application") is a non-provisional of U.S. Provisional Application No. 60/512,297, filed Oct. 17, 2003, entitled "IMPROVED TRANSPONDER SYSTEM AND METHOD." The '964 application is also a continuation-in-part U.S. patent application Ser. No. 10/340,352, filed Jan. 10, 2003, entitled "SYSTEM AND METHOD FOR INCENTING PAYMENT USING RADIO FREQUENCY IDENTIFICATION IN CONTACT AND CONTACTLESS TRANSACTIONS." The '352 application is a non-provisional of U.S. Provisional Application No. 60/396,577 filed Jul. 16, 2002. The '352 application is also a continuation-in-part of U.S. patent application Ser. No. 10/192,488, entitled "SYSTEM AND METHOD FOR PAYMENT USING RADIO FREQUENCY IDENTIFICATION IN CONTACT AND CONTACTLESS TRANSACTIONS," filed on Jul. 9, 2002, and now issued as U.S. Pat. No. 7,239,226 on Jul. 3, 2007. The '488 application is a non-provisional of U.S. Provisional Patent Application No. 60/304,216, filed Jul. 10, 2001. The '352 application is also a continuation-in-part of U.S. patent application Ser. No. 10/318,432, entitled "SYSTEM AND METHOD FOR SELECTING LOAD OPTIONS FOR USE IN RADIO FREQUENCY IDENTIFICATION IN CONTACT AND CONTACTLESS TRANSACTIONS," filed Dec. 13, 2002[;] The '432 application is a non-provisional of U.S. Provisional Application No. 60/396,577, filed Jul. 16, 2002. The '352 application is also a continuation-in-part of U.S. patent application Ser. No. 10/318,480, entitled "SYSTEM AND METHOD FOR PAYMENT USING RADIO FREQUENCY IDENTIFICATION IN CONTACT AND CONTACTLESS TRANSACTIONS," filed Dec. 13, 2002, and issued as U.S. Pat. No. 7,249,112 on Jul. 24, 2007. The '480 application is also a non-provisional of U.S. Provisional Patent Application No. 60/396,577, filed Jul. 16, 2002. All of the foregoing applications are incorporated herein by reference.

FIELD OF INVENTION

This invention generally relates to systems and methods for storing and accessing personal information on a Radio Frequency (RF) transponder, more specifically, to storing and accessing healthcare information.

BACKGROUND OF INVENTION

The U.S. Department of Health and Human Services has recently launched a new plan to convert the present healthcare information infrastructure to a nationwide, electronic network for healthcare information. Currently, only thirteen percent of hospitals nationwide have electronic systems, and only 14 to 28 percent of other physicians maintain electronic systems.

Electronic healthcare systems provide many challenges. For example, oftentimes, physicians and hospitals use computer systems for billing, while they use manual filing systems for tracking medical records. Therefore, information can be lost, mislaid, or inputted incorrectly for billing purposes. Recently, different software systems, such as CareRevolution by Electronic Healthcare Systems, have provided single point-of-care products that provide one database for both billing and medical information.

Nevertheless, medical and billing information must still be transferred from the patients to the physicians manually. Further, with patients moving and increased traveling, often the patient may not have all his medical information in one place and/or on hand when he needs medical attention. While current healthcare systems allow information to be maintained and held by the healthcare provider, it is desirable for such information to be portable and held with the patent instead.

Having the proper patient medical history has been shown to improve medical care and reduce medical errors. Further, improvements in health information technology have been estimated to produce savings of up to ten percent. Therefore, there is a need for a portable device for healthcare information.

SUMMARY OF INVENTION

A system and method for a RF transaction device for storing user personal data is disclosed. The invention includes a system and method for facilitating a healthcare transaction comprising an RF transponder system configured to store different healthcare information in different storage areas on a database. For example, medical insurance information may be stored in one type of format, while dental insurance information may be stored in a different format. The system and method for facilitating a healthcare transaction provides account information in ISO/IEC 7816 magnetic stripe Track 1/Track 2 format. The invention includes an RFID reader for transmitting account and database information.

In one exemplary embodiment the invention provides an RFID reader as a free standing or a computer implemented device. In another embodiment, biometric security measures are used in conjunction with the transponder system. The biometric security measures include pre-registration of biometric information and proffering biometric samples at biometric sensors configured with the transponder system.

In another exemplary embodiment, the transponder system communicates with one or more third-party healthcare providers to facilitate the transfer of healthcare and personal information. In another embodiment, the transponder system is configured with a GPS device to monitor and track locational information to provide local healthcare information and services.

These features and other advantages of the system and method, as well as the structure and operation of various exemplary embodiments of the system and method, are described below.

BRIEF DESCRIPTION OF THE DRAWINGS

The accompanying drawings, wherein like numerals depict like elements, illustrate exemplary embodiments of the present invention, and together with the description, serve to explain the principles of the invention. In the drawings:

FIG. 17 is an exemplary layout of the data stored in track 2 format; and

FIG. 18 is an example of a conventional magnetic stripe track 2 layout for MasterCard;

DETAILED DESCRIPTION

Figure 1A:
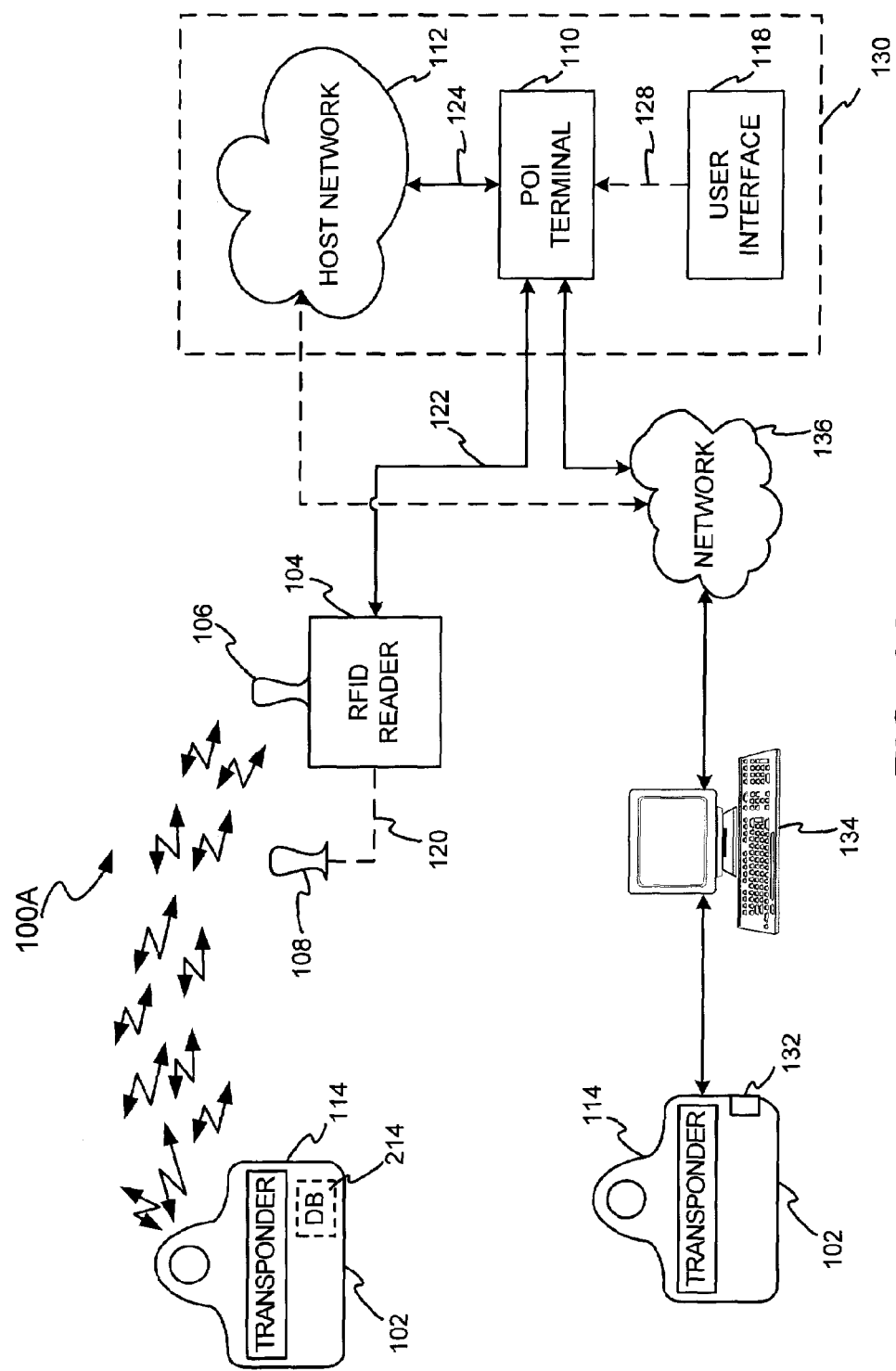
FIG. 1A illustrates an exemplary RFID-based system in accordance with the present invention, wherein exemplary components used for fob healthcare information are depicted.

The detailed description of exemplary embodiments of the invention herein makes reference to the accompanying block diagrams and flowcharts, which show the exemplary embodiment by way of illustration and its best mode. While these exemplary embodiments are described in sufficient detail to enable those skilled in the art to practice the invention, it should be understood that other embodiments may be realized and that logical and mechanical changes may be made without departing from the spirit and scope of the invention. Thus, the detailed description herein is presented for purposes of illustration only and not of limitation. For example, the steps recited in any of the method or process descriptions may be executed in any order and are not limited to the order presented.

Moreover, it should be appreciated that the particular implementations shown and described herein are illustrative of the invention and its best mode and are not intended to otherwise limit the scope of the present invention in any way. Indeed, for the sake of brevity, certain sub-components of the individual operating components, conventional data networking, application development and other functional aspects of the systems may not be described in detail herein. Furthermore, the connecting lines shown in the various figures contained herein are intended to represent exemplary functional relationships and/or physical couplings between the various elements. It should be noted that many alternative or additional functional relationships or physical connections may be present in a practical system.

The present invention may be described herein in terms of block diagrams, screen shots and flowcharts, optional selections and various processing steps. Such functional blocks may be realized by any number of hardware and/or software components configured to perform to specified functions. For example, the present invention may employ various integrated circuit components (e.g., memory elements, processing elements, logic elements, look-up tables, and the like), which may carry out a variety of functions under the control of one or more microprocessors or other control devices. Similarly, the software elements of the present invention may be implemented with any programming or scripting language such as C, C++, Java, COBOL, assembler, PERL, extensible markup language (XML), smart card technologies with the various algorithms being implemented with any combination of data structures, objects, processes, routines or other programming elements. Further, it should be noted that the present invention may employ any number of conventional techniques for data transmission, signaling, data processing, network control, and the like.

In addition, many applications of the present invention could be formulated. The exemplary network disclosed herein may include any system for accessing, storing, exchanging and/or otherwise manipulating user information, such as a distributed system, a thin cable network, an Ethernet, a token ring network, the Internet, an intranet, an extranet, wide area network (WAN), local area network (LAN), satellite communications, and/or the like. It is noted that the network may be implemented as other types of networks, such as an interactive television network (ITN).

The system user may interact with the system via any input device such as, a keypad, keyboard, mouse, kiosk, personal digital assistant, handheld computer (e.g., Palm Pilot®, Blueberry®), cellular phone and/or the like). For example, any input device may also be a "pervasive computing device," such as a traditionally non-computerized device that is embedded with a computing unit, such as, for example, watches, Internet-enabled kitchen appliances, restaurant tables embedded with RF readers, wallets or purses with imbedded transponders, etc. Similarly, the invention could be used in conjunction with any type of personal computer, network computer, work station, minicomputer, mainframe, or the like running any operating system such as any version of Windows, Windows NT, Windows 2000, Windows 98, Windows 95, MacOS, OS/2, BeOS, Linux, UNIX, Solaris, MVS or the like. Moreover, although the invention may frequently be described as being implemented with TCP/IP communications protocol, it should be understood that the invention could also be implemented using SNA, IPX, Appletalk, IPte, NetBIOS, OSI or any number of communications protocols. Moreover, the system contemplates, the use, sale, or distribution of any goods, services or information over any network having a similar functionality described herein.

FIG. 1A illustrates an exemplary RFID personal data system 100A that may include fob 102 having a transponder 114 and a RFID reader 104 in radio frequency (RF) communication with fob 102. In general, fob 102 may comprise one or more user databases 214 configured to store user information. These user databases 214 will be described in greater detail herein.

System 100A may be configured to provide access and/or to store user information in databases 214 in order to facilitate healthcare transactions, financial transactions, and/or any other type of transaction.

Fob 102 in accordance with this invention may be used to provide healthcare information, provide user information, pay for medical care, obtain healthcare access, provide identification, pay an amount, receive a payment, redeem reward points and/or the like. In the radio frequency ("RF") embodiments of fob 102, instrument to instrument transactions may also be performed. See, for example, Sony's "Near Field Communication" ("NFC") emerging standard which is touted as operating on 13.56 MHz and allowing the transfer of any kind of data between NFC enabled devices across a distance of up to twenty centimeters. See also, Bluetooth chaotic network configurations; described in more detail at http://www.palowireless.com/infotooth/whatis.asp, which is incorporated herein by reference. Furthermore, data on a first RF device may be transmitted directly or indirectly to another RF device to create a copy of all or part of the original device.

Although the present invention is described with respect to fob 102, the invention is not to be so limited. Indeed, system 100A may include any device having a transponder which is configured to communicate with a RFID reader 104 via RF communication. Typical devices may include, for example, a key ring, tag, card, cell phone, wristwatch, clothing or any such form capable of being presented for interrogation. System 100A may also include any non-transponder device configured to facilitate information transactions, such as, for example, credit cards, debit cards, loyalty cards, and the like.

RFID reader 104 may be configured to communicate using a RFID internal antenna 106. Alternatively, RFID reader 104 may include an external antenna 108 for communications with fob 102, where the external antenna may be made remote to RFID reader 104 using a suitable cable and/or data link 120. RFID reader 104 may be further in communication with a healthcare system 130 via a data link 122. System 100A may include a point-of-interaction device such as, for example, a healthcare point-of-interaction (POI) device 110 or a computer interface (e.g., user interface) 134. In one exemplary embodiment system 100A may include healthcare system 130 including POI device 110 in communication with RFID reader 104 (via data link 122). As described more fully below, system 100A may include the user interface 134 connected to a network 136 and to the transponder via a USB connector 132.

As used herein, a user may include any person, resource, product, employee, employer officer, nurse, doctor, health practitioner, hospital administrator, dentist, chiropractor, entity, manager, business, client, corporation, customer, contractor, administrator, operator, pet, equipment, supply, package, hardware and/or software.

The phrase "user information" as used herein, may include any user information such as transaction account information; personal information such as names, addresses, dates of birth, social security numbers, passport numbers, and employment information; healthcare information such as medical history, allergies, medical insurance information, dental insurance information; mortgage information; loyalty point information; membership information and/or any other type of information corresponding to a user. While the invention contemplates the communication, transfer, access and/or storage of any type of user information, the communication, transfer, access and/or storage of healthcare information may be used throughout for exemplary purposes.

Although the point-of-interaction device is described herein with respect to a healthcare point-of-interaction (POI) device, the invention is not to be so limited. Indeed, a healthcare POI device is used herein by way of example, and the point-of-interaction device may be any device capable of receiving fob account data. In this regard, the POI may be any point-of-interaction device enabling the user to complete a transaction and/or transfer information using fob 102. POI device 110 may be in further communication with a user interface 118 (via data link 128) for entering at least a customer's identity verification information. In addition, POI device 110 may be in communication with a healthcare host network 112 (via data link 124) for processing any transaction and/or user information request. In this arrangement, information provided by RFID reader 104 is provided to the POI device 110 of healthcare system 130 via data link 122. POI device 110 may receive the information (and alternatively may receive any identity verifying information from user interface 118 via data link 128) and provide the information to host system 112 for processing.

A variety of conventional communications media and protocols may be used for data links 120, 122, 124, and 128. For example, data links 120, 122, 124, and 128 may be an Internet Service Provider (ISP) configured to facilitate communications over a local loop as is typically used in connection with standard modem communications, cable modems, dish networks, ISDN, Digital Subscriber Lines (DSL), or any wireless communication media. In addition, healthcare system 130, including POI device 110 and host network 112, may reside on a local area network which interfaces to a remote network (not shown) for remote authorization of an intended transaction. Healthcare system 130 may communicate with the remote network via a leased line, such as a T1, D3 line, or the like. Such communications lines are described in a variety of texts, such as, "Understanding Data Communications," by Gilbert Held, which is incorporated herein by reference.

An account number, as used herein, may include any identifier for an account (e.g., insurance, credit, charge debit, checking, savings, reward, loyalty, or the like) which may be maintained by a healthcare and/or transaction account provider (e.g., payment authorization center) and/or which may be used to complete a transaction. A typical account number (e.g., account data) may be correlated to an insurance account, a credit or debit account, loyalty account, or rewards account maintained and serviced by such entities as American Express®, Visa® and/or MasterCard® or the like. For ease in understanding, the present invention may be described with respect to a medical insurance account.

In addition, the account number (e.g., account data) may be associated with any device, code, or other identifier/indicia suitably configured to allow the user to interact or communicate with the system, such as, for example, authorization/access code, personal identification number (PIN), Internet code, digital certificate, biometric data, and/or other identification indicia. The account number may be optionally located on a medical insurance card, rewards card, charge card, credit card, debit card, prepaid card, telephone card, smart card, magnetic stripe card, bar code card, loyalty card and/or the like. The account number may be distributed and stored in any form of plastic, electronic, magnetic, audio device and/or optical device capable of transmitting or downloading data to a second device. A user account number may be, for example, a sixteen-digit credit card number, although each credit provider has its own numbering system, such as the fifteen-digit numbering system used by American Express®. Each company's credit card numbers comply with that company's standardized format such that the company using a sixteen-digit format will generally use four spaced sets of numbers, as represented by the number "0000 0000 0000 0000". In a typical example, the first five to seven digits are reserved for processing purposes and identify the issuing bank, card type and, etc. In this example, the last sixteenth digit is used as a sum check for the sixteen-digit number. The intermediary eight-to-ten digits are used to uniquely identify the customer.

In various exemplary embodiments of the present invention, one or more transaction accounts may be used to satisfy or complete a transaction. For example, the transaction may be only partially completed using the transaction account(s) correlating to the application tenant information stored on fob 102 with the balance of the transaction being completed using other sources. Cash may be used to complete part of a transaction and the transaction account associated with a user and fob 102, may be used to satisfy the balance of the transaction. Alternatively, the user may identify which transaction account, or combination of transaction accounts, stored on fob 102 the user desires to complete the transaction. Any known or new methods and/or systems configured to manipulate the transaction account in accordance with the invention may be used.

The account number may be stored as Track 1 and Track 2 data as defined in ISO/IEC 7813, and further may be made unique to fob 102. In one exemplary embodiment, the account number may include a unique fob serial number and user identification number, as well as specific application applets. The account number may be stored in fob 102 inside a database 214, as described more fully below. Database 214 may be configured to store multiple account numbers issued to fob 102 user by the same or different account providing institutions. Where the account data corresponds to a loyalty or rewards account, the database 214 may be configured to store the attendant loyalty or rewards points data.

Figure 2:
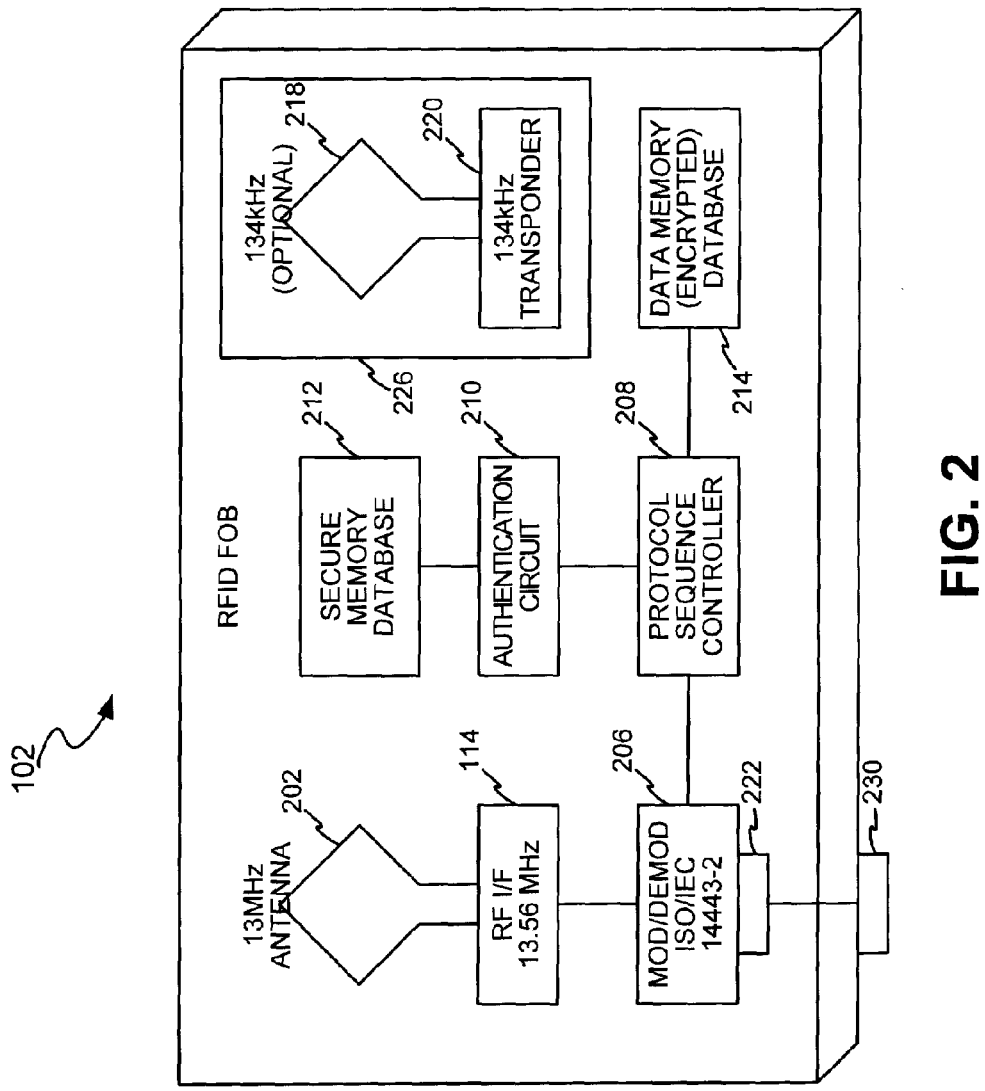
FIG. 2 is a schematic illustration of an exemplary fob in accordance with the present invention.

FIG. 2 illustrates a block diagram of the many functional blocks of an exemplary fob 102 in accordance with the present invention. Fob 102 may be a RFID fob 102 which may be presented by the user to facilitate an exchange of personal information such as medical information for facilitating healthcare services. As described herein, by way of example, fob 102 may be a RFID fob which may be presented for facilitating healthcare payment and/or services.

Fob 102 may include an antenna 202 for receiving an interrogation signal from RFID reader 104 via antenna 106 (or alternatively, via external antenna 108). Fob antenna 202 may be in communication with a transponder 114. In one exemplary embodiment, transponder 114 may be a 13.56 MHz transponder compliant with the ISO/IEC 14443 standard, and antenna 202 may be of the 13 MHz variety. The transponder 114 may be in communication with a transponder compatible modulator/demodulator 206 configured to receive the signal from transponder 114 and configured to modulate the signal into a format readable by any later connected circuitry. Further, modulator/demodulator 206 may be configured to format (e.g., demodulate) a signal received from the later connected circuitry in a format compatible with transponder 114 for transmitting to RFID reader 104 via antenna 202. For example, where transponder 114 is of the 13.56 MHz variety, modulator/demodulator 206 may be ISO/IEC 14443-2 compliant.

Modulator/demodulator 206 may be coupled to a protocol/sequence controller 208 for facilitating control of the authentication of the signal provided by RFID reader 104, and for facilitating control of the sending of fob 102 account number and/or other user information. In this regard, protocol/sequence controller 208 may be any suitable digital or logic driven circuitry capable of facilitating determination of the sequence of operation for fob 102 inner-circuitry. For example, protocol/sequence controller 208 may be configured to determine whether the signal provided by RFID reader 104 is authenticated, and thereby providing to RFID reader 104 the account number stored on fob 102.

Protocol/sequence controller 208 may be further in communication with authentication circuitry 210 for facilitating authentication of the signal provided by RFID reader 104. Authentication circuitry 210 may be further in communication with a non-volatile secure memory database 212. Secure memory database 212 may be any suitable elementary file system such as that defined by ISO/IEC 7816-4 or any other elementary file system allowing a lookup of data to be interpreted by the application on the chip.

Database 212 and any other database discussed herein may be any type of database, such as relational, hierarchical, graphical, object-oriented, and/or other database configurations. Common database products that may be used to implement the databases include DB2 by IBM (White Plains, N.Y.), various database products available from Oracle Corporation (Redwood Shores, Calif.), Microsoft Access or Microsoft SQL Server by Microsoft Corporation (Redmond, Wash.), or any other suitable database product. Moreover, the databases may be organized in any suitable manner, for example, as data tables or lookup tables. Each record may be a single file, a series of files, a linked series of data fields or any other data structure. Association of certain data may be accomplished through any desired data association technique such as those known or practiced in the art. For example, the association may be accomplished either manually or automatically. Automatic association techniques may include, for example, a database search, a database merge, GREP, AGREP, SQL, and/or the like. The association step may be accomplished by a database merge function, for example, using a "key field" in pre-selected databases or data sectors.

More particularly, a "key field" partitions the database according to the high-level class of objects defined by the key field. For example, certain types of data may be designated as a key field in a plurality of related data tables and the data tables may then be linked on the basis of the type of data in the key field. In this regard, the data corresponding to the key field in each of the linked data tables may be preferably the same or of the same type. However, data tables having similar, though not identical, data in the key fields may also be linked by using AGREP, for example. In accordance with one aspect of the present invention, any suitable data storage technique may be utilized to store data without a standard format. Data sets may be stored using any suitable technique, for example, storing individual files using an ISO/IEC 7816-4 file structure; implementing a domain whereby a dedicated file may be selected that exposes one or more elementary files containing one or more data sets; using data sets stored in individual files using a hierarchical filing system; data sets stored as records in a single file (for example, compression, SQL accessible, hashed via one or more keys, numeric, alphabetical by first tuple, etc.); block of binary (BLOB); stored as ungrouped data elements encoded using ISO/IEC 7816-6 data elements; stored as ungrouped data elements encoded using ISO/IEC Abstract Syntax Notation (ASN.1) as in ISO/IEC 8824 and 8825; and/or other proprietary techniques that may include fractal compression methods, image compression methods, etc.

In one exemplary embodiment, the ability to store a wide variety of information in different formats may be facilitated by storing the information as a Block of Binary (BLOB).

Thus, any binary information may be stored in a storage space associated with a data set. The BLOB method may store data sets as ungrouped data elements formatted as a block of binary via a fixed memory offset using either fixed storage allocation, circular queue techniques, or best practices with respect to memory management (e.g., paged memory, least recently used, etc.). By using BLOB methods, the ability to store various data sets that have different formats facilitates the storage of data associated with a wide variety of system components by multiple and unrelated owners of the data sets. For example, a first data set which may be stored may be provided by a first issuer, a second data set which may be stored may be provided by an unrelated second issuer, and yet a third data set which may be stored, may be provided by a third issuer unrelated to the first and second issuer. Each of these three exemplary data sets may contain different information that may be stored using different data storage formats and/or techniques. Further, each data set may contain subsets of data which also may be distinct from other subsets.

Information may be stored, accessed, and/or transmitted on database 214 and/or any other database described herein. For example the present invention provides a system and method for a RF operable transaction instrument configured to manage multiple data sets (e.g., "application tenants") of differing formats associated with a plurality of distinct transaction and/or healthcare account issuers. In this context, an "application tenant" may include all or any portion of any data sets which are substantially correlated to an account issuer, which the issuer may additionally use to substantially identify an instrument user or related account.

For example, where the account issuer provides application tenant information, the application tenant may include, for example, a healthcare identifier associated with a user enrolled in an issuer provided transaction account program, and all related subsets of data stored on fob 102. Where multiple application tenants are referred to herein, each tenant may constitute its own distinct data set, independent of any other application tenant data sets. For example, each application tenant may include a unique healthcare identifier and all associated subsets of data. Alternatively, an application tenant may include a healthcare identifier and an application for processing all data owned by an issuer. Thus, the data set or subset may include the processing application. Moreover, differing formats, as discussed herein, include differences in all or any portion of the formats. As such, "application tenant" and "distinct data set," and data set "owner," "healthcare issuer" and account "issuer" may be used interchangeably herein. Moreover, while reference may be made to healthcare, one skilled in the art will appreciate that the application similarly applies to other information.

As noted, in accordance with the invention, fob 102 is provided which permits the storage and presentment of at least one of a plurality of data sets for completing a transaction. The data sets may be stored on fob 102 itself, or on a remote database, as described below. The data sets stored with regard to fob 102 may be modified, deleted, added or augmented, as required by the healthcare issuer or the user. For example, as owner of the data, a healthcare issuer may modify a data set at the healthcare issuer's discretion. The healthcare issuer may modify the data, data subsets, member identifier and/or applications or data sets associated with its transaction account program. Such modifications may be completed or substantially completed in substantially real-time or at a later date, for example, when fob 102 is next presented.

In one exemplary embodiment, fob 102 itself is configured to store at least two data sets. In other exemplary embodiments, data sets may be stored in one or more databases and the data sets are affiliated with fob 102. For example, a central database on fob 102 may store multiple distinct data sets correlated with a unique healthcare provider. The data sets stored on the remote database may be stored thereon in such a manner as to mimic the corresponding data sets stored on fob 102. The multiple distinct data sets may be accessed, for example, by a healthcare system, whether stored on fob 102 or remote database stand alone device, and/or a computer user interface, via a network. In this example, fob 102 may include one or more user identifiers (e.g., insurance identifiers), which may be used to provide access to a subset of data included on fob 102.

Although all data sets associated with a particular fob 102 may be owned by the same owner, it is contemplated that in general, some of the data sets stored on fob 102 have different owners. Furthermore, the storage of data sets is configured to facilitate independent storage and management of the data sets on fob 102. Further still, the data sets may be stored in distinct differing formats provided by the distinct issuer or data set owner (also called "issuer" herein). The owners of data sets may include different individuals, entities, businesses, corporations, software, hardware, and/or the like. However, one skilled in the art will appreciate that the owners may also include different divisions or affiliates of the same corporation or entity.

A data set may contain any type of information stored in digital format. For example, a data set may include account numbers, programs/applications, scripts, cookies, instruments for accessing other data sets, and/or any other information.

As discussed above, many issuers of existing healthcare transaction instruments utilize predetermined formats for medical information, insurance numbers, account data, personal data and/or applications stored in association with fob 102. Similarly, the data storage media associated with these healthcare transaction instruments are typically configured to accommodate specific predetermined data formats. Thus, since the data format associated with a first issuer is often different from a data format of a second issuer, storage of multiple distinct data of differing formats on a single device provides complications for conventional systems. This is often true since, each issuer typically maintains an account processing system that uses a processing protocol different from other issuers, and the information stored on the transaction card relative to the issuer must be formatted accordingly. As such, to ensure the security and integrity of the issuer-owned data, the loading of data on fob 102 is typically performed by a healthcare provider, issuer or a third-party provider who typically uploads all related and similarly formatted data sets onto fob 102. However, since the third party may typically only be authorized by the issuer and/or healthcare provider to load issuer-owned data of similar format onto an issuer-provided fob 102, including differently formatted data sets on a single transaction device by the third party is often not permitted. More particularly, independent owners of data sets are often reluctant to conform their data set formats to a "standard format" because of the security advantages of maintaining a separate, distinct, often secreted format.

As stated above, in various embodiments of the present invention, the data may be stored without regard to a common format. However, in one exemplary embodiment of the present invention, the data set (e.g., BLOB) may be annotated in a standard manner when provided for manipulating the data onto the network. The annotation may comprise a short header, trailer, or other appropriate indicator related to each data set that may be configured to convey information useful in managing the various data sets. For example, the annotation may be called a "condition header," "header," "trailer," or "status," herein, and may comprise an indication of the status of the data set or may include an identifier correlated to a specific issuer or owner of the data. In one example, the first three bytes of each data set BLOB may be configured or configurable to indicate the status of that particular data set (e.g., LOADED, INITIALIZED, READY, BLOCKED, REMOVABLE, or DELETED). Subsequent bytes of data may be used to indicate for example, the identity of the user, user, account identifier or the like. Each of these condition annotations are further discussed herein.

The data may be used by protocol/sequence controller 208 for data analysis and used for management and control purposes, as well as security purposes. Authentication circuitry may authenticate the signal provided by RFID reader 104 by association of the RFID signal to authentication keys stored on database 212. Encryption circuitry may use keys stored on database 212 to perform encryption and/or decryption of signals sent to or from the RFID reader 104. Separate authentication keys may be used for each data set owner. The data set may consist of a directory file and/or an elementary file as defined in the ISO/IEC 7813 specification. A separate authentication key may be required to access the directory file and/or another key may be required for authentication to access the elementary file. The authentication keys may be supplemented with keys used to encrypt the data stored in the data set. The authentication and encryption keys may also be unique to the data set owner to prevent unauthorized access to the data. The RFID reader 104 and/or the terminal that is connected to the RFID reader 104 may contain the keys used to authenticate access to the data sets. The reader may also contain the encryption keys to decrypt the data in the data sets.

The data may be used by protocol/sequence controller 208 for data analysis and used for management and control purposes, as well as security purposes. Authentication circuitry may authenticate the signal provided by RFID reader 104 by association of the RFID signal to authentication keys stored on database 212. Encryption circuitry may use keys stored on database 212 to perform encryption and/or decryption of signals sent to or from RFID reader 104. For a basic introduction on cryptography, review a text written by Bruce Schneier entitled "Applied Cryptography: Protocols, Algorithms, and Source Code in C," published by John Wiley & Sons (second edition, 1995), herein incorporated by reference.

In addition, protocol/sequence controller 208 may be in communication with a database 214 for storing at least fob 102 transponder account data, and a unique fob 102 identification code. Protocol/sequence controller 208 may be configured to retrieve the account identifier from database 214 as desired. Database 214 may be of the same configuration as database 212 described above. The fob transponder account data and/or unique fob identification code stored on database 214 may be encrypted prior to storage. Thus, where protocol/sequence controller 208 retrieves the account data, and or unique fob identification code from database 214, the transponder account identifier may be encrypted when being provided to RFID reader 104. Further, the data stored on database 214 may include, for example, an unencrypted unique fob 102 identification code, a user identification, Track 1 and Track 2 data, as well as specific application applets.

For example, in accordance with another exemplary embodiment, the account number may be stored in magnetic stripe format. That is, where the account number may be in magnetic stripe format, the account number portions are governed by the International Standards Organization ISO/IEC 7811, et al. standard, which are hereby incorporated by reference. The standard requires the magnetic stripe information to be encoded in three "tracks" (i.e., track 1, track 2, and track 3).

Data stored in track 1 may be typically used to verify the user's identity. Track 1 may be reserved for encoding the transaction account identifier, the name of the accountholder, and at least the expiration date of the transaction account or the transaction device. The information encoded in track 1 may be alphanumeric and may be encoded at about 7 Bits/Character. In an exemplary layout of the data stored in track 1, track 1 may be segmented into several distinct predetermined portions (e.g., "fields") for encoding the various account identifying information. The following table may be useful for determining the field definitions of the information provided.

TABLE 1

Table of Field Codes for Track 1

SS = Start Sentinel "%"
FC = Format Code
PAN = Primary Acct. # (19 digits max)
FS = Field Separator " "
Name = 26 alphanumeric characters max.
Additional Data = Expiration Date, offset, encrypted PIN, etc.
ES = End Sentinel "?"
LRC = Longitudinal Redundancy Check Track 2 may be the track most commonly used by the American Banking Association associated banking institutions. Track 2 may be typically reserved for a duplicate version of the transaction account identifier and the expiration date of the transaction account or the transaction device stored in track 1. In addition, track 2 may include an encrypted Personal Identification Code, and other discretionary data. However, the data in track 2 may be encoded at a lower Bit per Character density than the data encoded in track 1. The data in track 2 may be numeric only and may be encoded at about 5 Bits/Character. The lower density ratio in track 2 may be designed to ensure compatibility with older technology readers and to provide redundancy when reading with newer technology readers. FIG. 17 illustrates an exemplary layout of the data stored in track 2, wherein track 2 may be segmented into several distinct predetermined portions for encoding the various account identifying information. As shown, the following table may be useful for determining the definitions of the information provided.

TABLE 2

Table of Field Codes for Track 2

SS = Start Sentinel "%"
SS = Start Sentinel ";"
PAN = Primary Acct. # (19 digits max)
FS = Field Separator "="
Additional Data = Expiration Date, offset, encrypted PIN, etc.
ES = End Sentinel "?"
LRC = Longitudinal Redundancy Check Track 3 may be of similar description as Track 2. With the International Standards Organization adoption of standard ISO/IEC 4909, track 3 of the magnetic stripe format was no longer used by the banking industry. However, other transaction devices including a magnetic stripe, such as drivers licenses, use track 3, which may include both numeric only and alphanumeric characters. Track 3 may be unique in that track 3 was intended to have data read and WRITTEN on it. Cardholders would have account information UPDATED right on the magnetic stripe. The present invention anticipates that a fob user's travel-related information profile and/or account information may be updated using track 3. Unfortunately, track 3 may be almost an orphaned standard, since most readers currently in operation are not configured to write data from track 3. The original design of track 3 was to control off-line ATM transactions by recording transaction data for later reference by the banking institution. But since ATMs are now on-line, the usage of track 3 has been drastically reduced.

The most common technique used to encode data in magnetic stripe format may be known as Aiken Biphase, or 'two-frequency coherent-phase encoding.' The American National Standards Institute (ANSI) and the International Standards Organization (ISO) have chosen two standards to guide the encoding process. The ISO encoding protocol specifies that each of tracks 1, 2 and 3 must begin and end with a length of all Zero bits, called CLOCKING BITS. These are used to synch the self-clocking feature of bi-phase decoding. In addition, most transaction devices which use magnetic stripe encoding protocol use either the ANSI/ISO ALPHA Data format or the ANSI/ISO BCD Data format. For example, track 1 may be typically encoded in ANSI/ISO ALPHA Data format which may be a 7 bit, 6 data bits+1 parity bit (odd) format, where the data may be read least significant bit first. The ANSI/ISO ALPHA format character set contains 64 characters, 43 alphanumeric, 3 framing/field characters and 18 control/special characters. On the other hand, tracks 2 and 3 are typically encoded in ANSI/ISO BCD Data format, which may be a 5 bit, 4 data bits+1 parity bit(odd) format. The character set for the ANSI/ISO BCD Data format character set contains 16 characters, 10 alphanumeric, 3 framing/field characters and 3 control/special characters.

Ordinarily, a proxy account number (e.g., a portion of the transaction account number) includes essential identifying information, such as, for example, any information that may be common to the account provider. The common information (also called "common character," herein) may include the account provider routing number, or common source indicator such as the character spaces reserved to indicate the identification of the issuing bank. Thus, where the proxy transaction account identifier corresponds to an American Express account, the proxy transaction account identifier may include the common prefix number 3715, encoded the field location where such common character may be ordinarily encoded in traditional magnetic stripe format. The prefix 3715 is an example of the required set of digits in the account number required to identify the issuer as American Express. Each credit card issuer has a unique set of digits commonly agreed upon between institutions that identifies the issuer.

FIG. 18 illustrates the encoding of which would ordinarily be done by an entity, such as, for example, MasterCard in track 2 format. FIG. 18 shows the encoding of a MasterCard account number 3111 2222 3333 4444 with expiration date 12/99 in traditional track 1 format. Since MasterCard uses the number 3111 to identify its transaction accounts, the proxy account identifier may also use the number 3111 so that the receiving system (e.g., RFID reader 104 or merchant system 130, or account provider) further recognizes that the proxy account identifier may be from a MasterCard transaction device. It should be noted that in this example, the "3" and the "101" may be common characters to all MasterCard transaction accounts. For a more detailed explanation of magnetic stripe format data exchange, see U.S. patent application Ser. No. 10/810,473, filed Mar. 26, 2004, entitled "SYSTEM AND METHOD FOR ENCODING INFORMATION IN MAGNETIC STRIPE FORMAT FOR USE IN RADIO FREQUENCY IDENTIFICATION TRANSACTIONS," incorporated herein by reference.

Fob 102 may be configured to respond to multiple interrogation frequency transmissions provided by RFID reader 104. That is, as described more fully below, RFID reader 104 may provide more than one RF interrogation signal. In this case, fob 102 may be configured to respond to the multiple frequencies by including in fob 102 one or more additional RF signal receiving/transmitting units 226. RF signal receiving/transmitting unit 226 may include an antenna 218 and transponder 220 where the antenna 218 and transponder 220 are compatible with at least one of the additional RF signals provided by RFID reader 104. For example, in one exemplary embodiment, fob 102 may include a 134 KHz antenna 218 configured to communicate with a 134 KHz transponder 220. In this exemplary configuration, an ISO/IEC 14443-2 compliant modulator/demodulator may not be required. Instead, the 134 KHz transponder may be configured to communicate directly with the protocol/sequence controller 208 for transmission and receipt of authentication and account number signals as described above.

In another embodiment, fob 102 may further include a universal serial bus (USB) connector 132 for interfacing fob 102 to a user interface 134. User interface 134 may be further in communication with a POI device 110 via a network 136. Network 136 may be the Internet, an intranet, or the like as is described above with respect to network 112. Further, the user interface 134 may be similar in construction to any conventional input devices and/or computing systems aforementioned for permitting the system user to interact with the system. In one exemplary embodiment, fob 102 may be configured to facilitate online Internet payments. A USB converter 222 may be in communication with a USB connector 232 for facilitating the transfer of information between the modulator/demodulator 206 and USB connector 132. Alternatively, USB converter 222 may be in communication with protocol/sequence controller 208 to facilitate the transfer of information between protocol/sequence controller 208 and USB connector 132.

Where fob 102 includes a USB connector 132, fob 102 may be in communication with, for example, a USB port on user interface 134. The information retrieved from fob 102 may be compatible with credit card and/or smart card technology enabling usage of interactive applications on the Internet. No RFID reader may be required in this embodiment since the connection to POI device 110 may be made using a USB port on user interface 134 and a network 136.

Fob 102 may include means for enabling activation of the fob by the user. In one exemplary embodiment, a switch 230 which may be operated by the user of fob 102. The switch 230 on fob 102 may be used to selectively or inclusively activate fob 102 for particular uses. In this context, the term "selectively" may mean that switch 230 enables the user to place fob 102 in a particular operational mode. For example, the user may place fob 102 in a mode for enabling purchase of a good or of a service using a selected account number. Alternatively, the fob may be placed in a mode as such that the fob account number is provided by USB port 132 (or serial port) only and fob transponder 114 is disabled. In addition, the term "inclusively" may mean that fob 102 is placed in an operational mode permitting fob 102 to be responsive to the RF interrogation and interrogation via the USB connector 132. In one particular embodiment, switch 230 may remain in an OFF position ensuring that one or more applications or accounts associated with fob 102 are non-reactive to any commands issued by RFID reader 104. As used herein, the OFF position may be termed the "normal" position of activation switch 230, although other normal positions are contemplated.

In another exemplary embodiment, when switch 230 is moved from the OFF position, fob 102 may be deemed activated by the user. That is, switch 230 may activate internal circuitry in fob 102 for permitting the fob to be responsive to RF signals (e.g., commands from RFID reader 104). In this way, switch 230 may facilitate control of the active and inactive states of fob 102. Such control increases the system security by preventing inadvertent or illegal use of fob 102.

In one exemplary embodiment, switch 230 may be a simple mechanical device in communication with circuitry which may electrically prevent the fob from being powered by a RFID reader. That is, when switch 230 is in its normal position, switch 230 may provide a short to fob 102 internal circuitry, preventing fob 102 from being responsive to interrogation by RF or via the USB connector 132. In this arrangement, switch 230 may be, for example, a "normally closed" (NC) configured switch, which may be electrically connected to antenna 202 at the interface of antenna 202 and transponder 114. Switch 230 may be depressed, which may open switch 230 fully activating antenna 202.

In yet another exemplary embodiment, fob 102 may include a biometric sensor and biometric membrane configured to operate as switch 230 and activate fob 102 when provided biometric signal from fob 102 user. Such biometric signal may be the digital reading of a fingerprint, thumbprint, or the like. Typically, where biometric circuitry is used, the biometric circuitry may be powered by an internal voltage source (e.g., battery). In this case, the switch may not be a simple mechanical device, but a switch which is powered. In yet another exemplary embodiment, switch 230 may be battery powered though no biometric circuitry is present in fob 102.

In yet another embodiment, switch 230 may be a logic switch. Where switch 230 is a logic switch 230 control software may be read from sequence controller 208 to selectively control the activation of the various fob 102 components.

Figure 3:
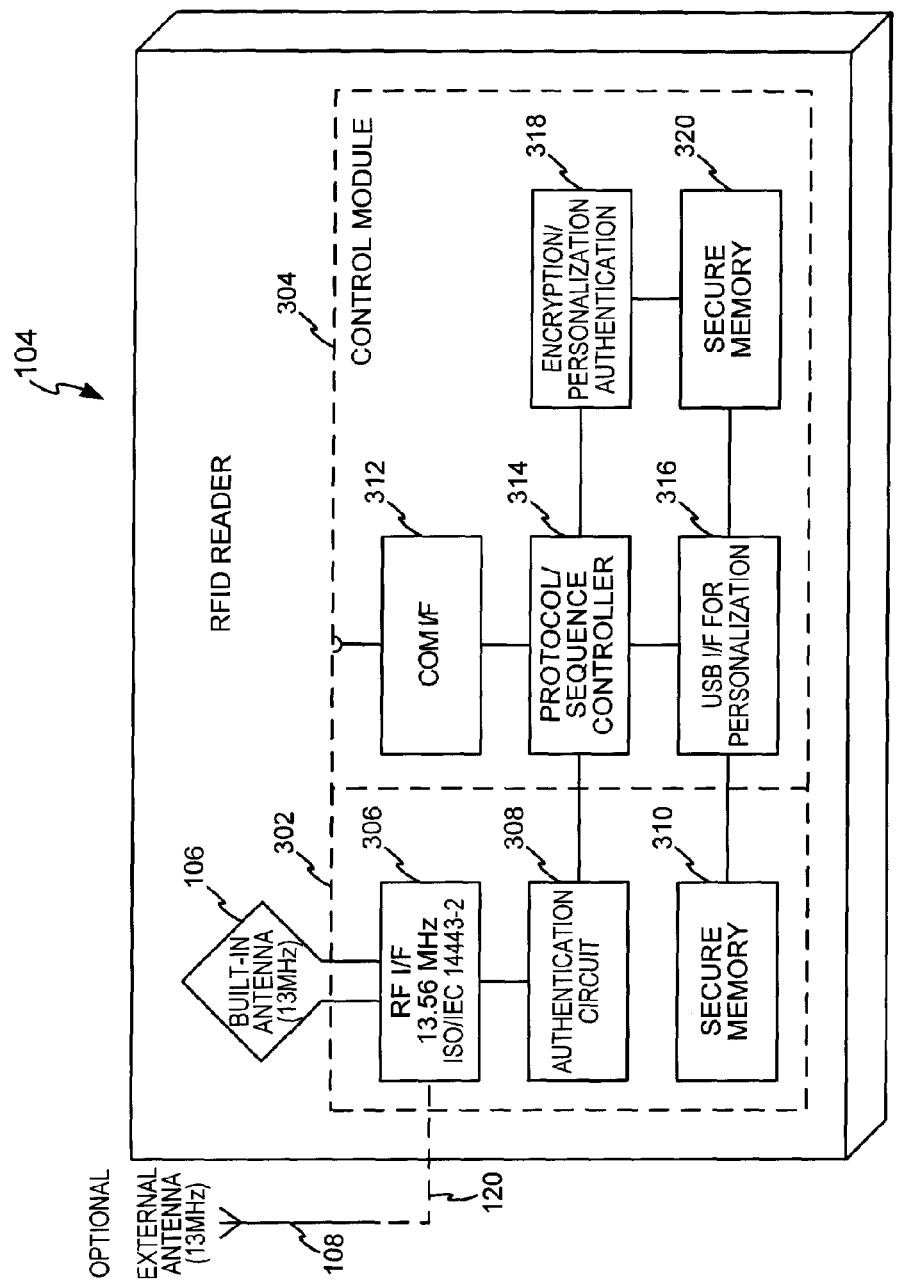
FIG. 3 is a schematic illustration of an exemplary RFID reader in accordance with the present invention.

FIG. 3 illustrates an exemplary block diagram of RFID reader 104 in accordance with an exemplary embodiment of the present invention. RFID reader 104 includes, for example, an antenna 106 coupled to a RF module 302, which is further coupled to a control module 304. In addition, RFID reader 104 may include an antenna 108 positioned remotely from RFID reader 104 and coupled to RFID reader 104 via a suitable cable 120, or other wire or wireless connection.

RF module 302 and antenna 106 may be suitably configured to facilitate communication with fob 102. Where fob 102 is formatted to receive a signal at a particular RF frequency, RF module 302 may be configured to provide an interrogation signal at that same frequency. For example, in one exemplary embodiment, fob 102 may be configured to respond to an interrogation signal of about 13.56 MHz. In this case, RFID antenna 106 may be 13 MHz and may be configured to transmit an interrogation signal of about 13.56 MHz. That is, fob 102 may be configured to include a first and second RF module (e.g., transponder) where the first module may operate using a 134 kHz frequency and the second RF module may operate using a 13.56 MHz frequency. RFID reader 104 may include two receivers which may operate using the 134 kHz frequency, the 13.56 MHz frequency or both. When RFID reader 104 is operating at 134 kHz frequency, only operation with the 134 kHz module on fob 102 may be possible. When RFID reader 104 is operating at the 13.56 MHz frequency, only operation with the 13.56 MHz module on fob 102 may be possible. Where RFID reader 104 supports both a 134 kHz frequency and a 13.56 MHz RF module, fob 102 may receive both signals from RFID reader 104. In this case, fob 102 may be configured to prioritize selection of the one or the other frequency and reject the remaining frequency. Alternatively, RFID reader 104 may receive signals at both frequencies from fob 102 upon interrogation. In this case, RFID reader 104 may be configured to prioritize selection of one or the other frequency and reject the remaining frequency.

Further, a protocol/sequence controller 314 may include an optional feedback function for notifying the user of the status of a particular healthcare information transaction. For example, the optional feedback may be in the form of an LED, LED screen and/or other visual display which is configured to light up or display a static, scrolling, flashing and/or other message and/or signal to inform a user using fob 102 that a healthcare information transaction is initiated (e.g., fob is being interrogated), the fob is valid (e.g., fob is authenticated), a healthcare information transaction is being processed, (e.g., fob transponder account identifier is being read by RFID reader 104) and/or the transaction is accepted or denied (e.g., account identifiers approved or disapproved). Such an optional feedback may or may not be accompanied by an audible indicator (or may present the audible indicator singly) for informing fob 102 user of the healthcare information transaction status. The audible feedback may be a simple tone, multiple tones, musical indicator, and/or voice indicator configured to signify when fob 102 is being interrogated, the healthcare information transaction status, or the like.

RFID antenna 106 may be in communication with a transponder 306 for transmitting an interrogation signal and receiving at least one of an authentication request signal and/or an account data from fob 102. Transponder 306 may be of similar description as transponder 114 of FIG. 2. In particular, transponder 306 may be configured to send and/or receive RF signals in a format compatible with antenna 106 in similar manner as was described with respect to fob transponder 114. For example, where transponder 306 is 13.56 MHz RF rated antenna 106 may be 13.56 MHz compatible. Similarly, where transponder 306 is ISO/IEC 14443 rated, antenna 106 may be ISO/IEC 14443 compatible.

RF module 302 may include, for example, transponder 306 in communication with authentication circuitry 308 which may be in communication with a secure database 310. Authentication circuitry 308 and database 310 may be of similar description and operation as described with respect to authentication circuitry 210 and secure memory database 212 of FIG. 2. For example, database 310 may store data corresponding to fob 102 which may be used to authorize the tracking of user performance over system 100. Database 310 may additionally store RFID reader 104 identifying information and/or provide such information to fob 102 for use in authenticating whether RFID reader 104 is authorized to be provided the fob transponder account identifier stored on fob database 214.

Authentication circuitry 308 may be of similar description and operation as authentication circuitry 210. That is, authentication circuitry 308 may be configured to authenticate the signal provided by fob 102 in a similar manner that authentication circuitry 210 may be configured to authenticate the signal provided by RFID reader 104. As is described more fully below, fob 102 and RFID reader 104 engage in mutual authentication. In this context, "mutual authentication" may mean that operation of the system 100 may not take place until fob 102 authenticates the signal from RFID reader 104, and RFID reader 104 authenticates the signal from fob 102.

Figure 4:
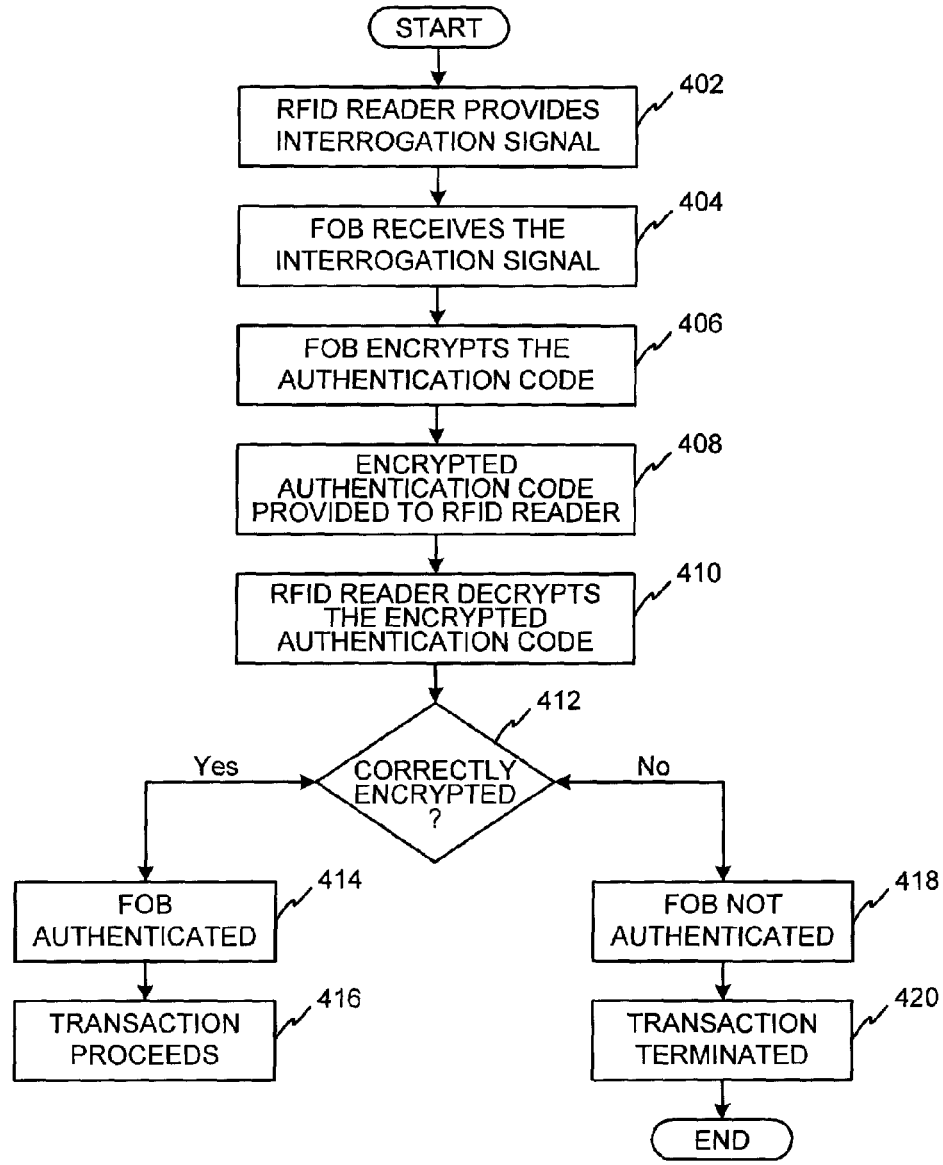
FIG. 4 is an exemplary flow diagram of an exemplary authentication process in accordance with the present invention.

FIG. 4 depicts a flowchart of an exemplary authentication process in accordance with the present invention. The authentication process is depicted as one-sided. That is, the flowchart depicts the process of RFID reader 104 authenticating fob 102, although similar steps may be followed in the instance that fob 102 authenticates RFID reader 104.

As noted, database 212 may store security keys for encrypting or decrypting signals received from RFID reader 104. In an exemplary authentication process, where RFID reader 104 is authenticating fob 102, RFID reader 104 may provide an interrogation signal to fob 102 (step 402). The interrogation signal may include a random code generated by the RFID reader authentication circuit 210, which is provided to fob 102 and which is encrypted using an unique encryption key corresponding to the unique fob 102 identification code. For example, protocol/sequence controller 314 may provide a command to activate the authentication circuitry 308. Authentication circuitry 308 may provide from database 310 a fob interrogation signal including a random number as a part of the authentication code generated for each authentication signal. The authentication code may be an alphanumeric code which is recognizable (e.g., readable) by RFID reader 104 and fob 102. The authentication code may be provided to fob 102 via the RFID RF interface 306 and antenna 106 (or alternatively antenna 108).

Fob 102 receives the interrogation signal (step 404). The interrogation signal including the authorization code may be received at RF interface 114 via antenna 202. Once fob 102 is activated, the interrogation signal including the authorization code may be provided to the modulator/demodulator circuit 206 where the signal may be demodulated prior to providing the signal to protocol/sequence controller 208. Protocol/sequence controller 208 may recognize the interrogation signal as a request for authentication of fob 102, and provide the authentication code to authentication circuit 210. Fob 102 may then encrypt the authentication code (step 406). In particular, encryption may be done by authentication circuit 210, which may receive the authentication code and encrypt the code prior to providing the encrypted authentication code to protocol/sequence controller 208. Fob 102 may then provide the encrypted authentication code to RFID reader 104 (step 408). That is, the encrypted authentication code may be provided to RFID reader 104 via modulator/demodulator circuit 206, RF interface 114 (e.g., transponder 114) and antenna 106.

RFID reader 104 may then receive the encrypted authentication code and decrypt it (step 410). That is, the encrypted authentication code may be received at antenna 106 and RF interface 306 and may be provided to authentication circuit 308. Authentication circuit 308 may be provided a security authentication key (e.g., transponder system decryption key) from database 310. The authentication circuit may use the authentication key to decrypt (e.g., unlock) the encrypted authorization code. The authentication key may be provided to the authentication circuit based on the unique fob 102 identification code. For example, the encrypted authentication code may be provided along with the unique fob 102 identification code. The authentication circuit may receive the unique fob 102 identification code and retrieve from database 310 a transponder system decryption key correlative to the unique fob 102 identification code for use in decrypting the encrypted authentication code.

Once the authentication code is decrypted, the decrypted authentication code is compared to the authentication code provided by RFID reader 104 at step 402 (step 412) to verify its authenticity. If the decrypted authorization code is not readable (e.g., recognizable) by the authentication circuit 308, fob 102 is deemed to be unauthorized (e.g., unverified) (step 418) and the operation of system 100 is terminated (step 420). Contrarily, if the decrypted authorization code is recognizable (e.g., verified) by fob 102, the decrypted authorization code is deemed to be authenticated (step 414), and the transaction is allowed to proceed (step 416). In one particular embodiment, the proceeding transaction may mean that fob 102 may authenticate RFID reader 104 prior to RFID reader 104 authenticating fob 102, although, it should be apparent that RFID reader 104 may authenticate fob 102 prior to fob 102 authenticating RFID reader 104.

It should be noted that in an exemplary verification process, authorization circuit 308 may determine whether the unlocked authorization code is identical to the authorization code provided in step 402. If the codes are not identical then fob 102 is not authorized to access system 100. Although the verification process is described with respect to situations where identical codes are used, in other embodiments identical codes are not required. For example, authentication circuit 308 may verify the decrypted code through any protocol, steps, or process for determining whether the decrypted code corresponds to authorized fob 102.

Figure 5:
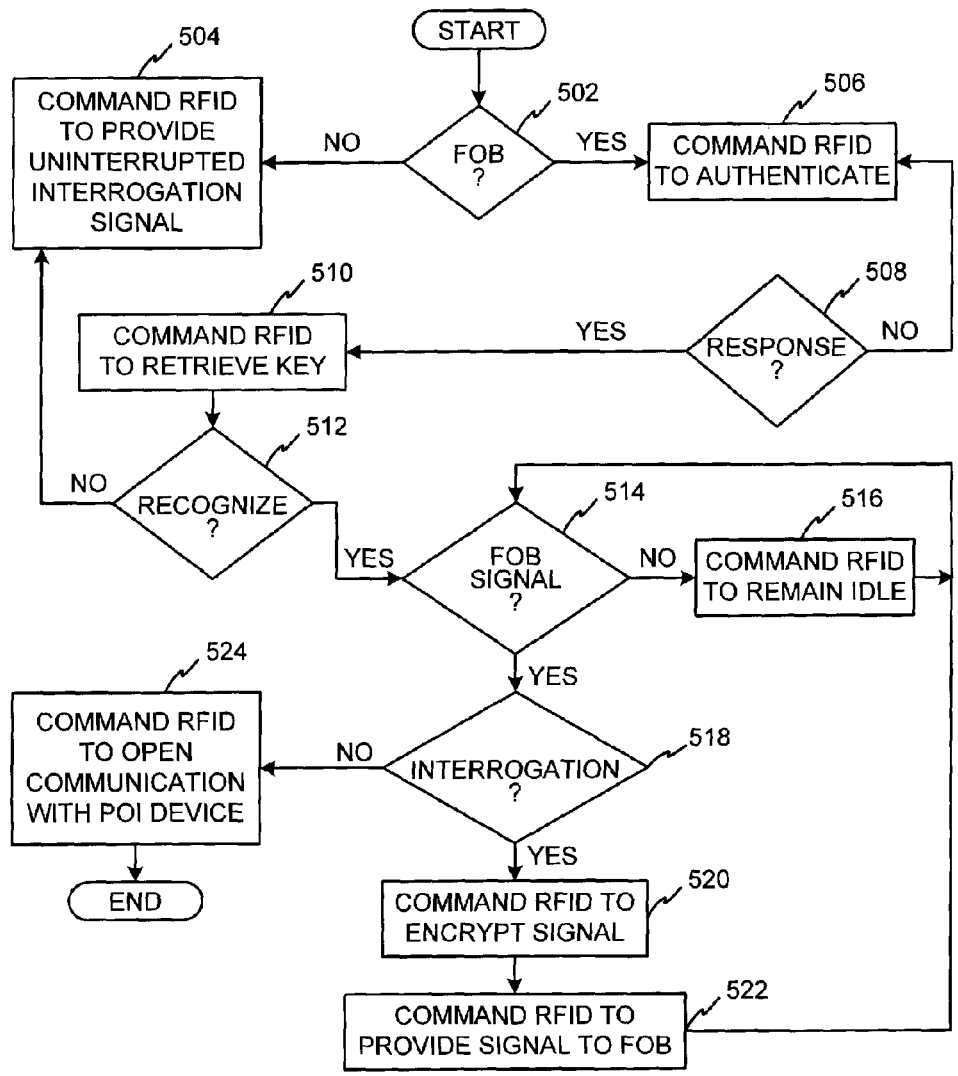
FIG. 5 is an exemplary flow diagram of an exemplary decision process for a protocol/sequence controller in accordance with the present invention.

Authentication circuitry 308 may additionally be in communication with protocol/sequence controller 314 of similar operation and description as protocol/sequence controller 208 of FIG. 2. That is, protocol/sequence device controller 314 may be configured to determine the order of operation of RFID reader 104 components. For example, FIG. 5 illustrates an exemplary decision process under which protocol/sequence controller 314 may operate. Protocol/sequence controller 314 may command the different components of RFID reader 104 based on whether fob 102 is present (step 502). For example, if fob 102 is not present, then protocol/sequence controller 314 may command RFID reader 104 to provide an uninterrupted interrogation signal (step 504). That is, protocol/sequence controller 314 may command authentication circuit 308 to provide an uninterrupted interrogation signal until the presence of fob 102 is realized. If fob 102 is present, the protocol/sequence controller 314 may command RFID reader 104 to authenticate fob 102 (step 506).

As noted above, authentication may mean that protocol/sequence controller 314 may command authentication circuit 308 to provide fob 102 with an authorization code. If a response is received from fob 102, protocol/sequence controller may determine if the response is a response to RFID reader 104 provided authentication code, or if the response is a signal requiring authentication (step 508). If the signal requires authentication, then protocol/sequence controller 314 may activate the authentication circuit as described above (step 506). On the other hand, if fob 102 signal is a response to the provided authentication code, then protocol/sequence controller 314 may command RFID reader 104 to retrieve the appropriate security key for enabling recognition of the signal (step 510). That is, protocol/sequence controller 314 may command authentication circuit 308 to retrieve from database 310 a security key (e.g., transponder system decryption key), unlock the signal, and compare the signal to the signal provided by RFID reader 104 in the authentication process (e.g., step 506). If the signal is recognized, protocol/sequence controller 314 may determine that fob 102 is authorized to access system 100. If the signal is not recognized, then fob 102 is considered not authorized (step 512), in which case, protocol/sequence controller 314 may command the RFID controller to interrogate for authorized fobs (step 504).

Once protocol/sequence controller 314 determines that fob 102 is authorized, protocol/sequence controller 314 may seek to determine if additional signals are being sent by fob 102 (step 514). If no additional signal is provided by fob 102, then protocol/sequence controller 314 may provide all the components of RFID reader 104 to remain idle until such time as a signal is provided (step 516). Contrarily, where an additional fob 102 signal is provided, protocol/sequence controller 314 may determine if fob 102 is requesting access to engine 130 POI terminal 110 or if fob 102 is attempting to interrogate RFID reader 104 for return (e.g., mutual) authorization (step 518). Where fob 102 is requesting access to engine 130 POI terminal 110, protocol/sequence controller 314 may command RFID reader 104 to open communications with POI terminal 110 (step 524). In particular, protocol/sequence controller 314 may command POI terminal communications interface 312 to become active, permitting transfer of data between RFID reader 104, engine 130, and POI terminal 110.

On the other hand, if protocol/sequence controller 314 determines that fob 102 signal is a mutual interrogation signal, then protocol/sequence controller 314 may command RFID reader 104 to encrypt the signal (step 520). Protocol/sequence controller 314 may command encryption authentication circuit 318 to retrieve from database 320 the appropriate encryption key in response to fob 102 mutual interrogation signal. Protocol/sequence controller 314 may then command RFID reader 104 to provide the encrypted mutual interrogation signal to fob 102. Protocol/sequence controller 314 may command authentication circuit 318 to provide an encrypted mutual interrogation signal for fob 102 to mutually authenticate (step 522). Fob 102 may then receive the encrypted mutual interrogation signal and retrieve from authentication circuitry 212 a RFID reader 104 decryption key.

Although an exemplary decision process of protocol/sequence controller 314 is described, it should be understood that a similar decision process may be undertaken by protocol/sequence controller 208 in controlling the components of fob 102. Indeed, as described above, protocol/sequence controller 314 may have similar operation and design as protocol/sequence controller 208. In addition to the above, protocol/sequence controllers 208 and 314 may incorporate in the decision process appropriate commands for enabling USB interfaces 222 and 316, when the corresponding device is so connected.

Encryption/decryption component 318 may be further in communication with a secure account identifier database 320 which stores the security keys necessary for decrypting the encrypted fob account identifier. Upon appropriate request from protocol/sequence controller 314, encryption/decryption component (e.g., circuitry 318) may retrieve the appropriate security key, decrypt the fob account identifier and forward the decrypted account identifier to protocol/sequence controller 314 in any format readable by any later connected POI terminal 110. In one exemplary embodiment, the account identifier may be forwarded in a conventional magnetic stripe card format compatible with the ISO/IEC 7813 standard. That is, in accordance with the invention, there is no need to translate or correlate the account identifier to traditional magnetic stripe format as is done with the prior art. The invention processes the user and/or healthcare information request directly, as if the card associated with the account has been presented for storing user and/or healthcare information.

Upon receiving the account identifier in magnetic stripe format, protocol/sequence controller 314 may forward the account identifier to POI terminal 110 via communications interface 312 and data link 122, as best shown in FIG. 1A. POI terminal 110 may receive the decrypted account identifier and forward the magnetic stripe formatted account identifier to host network 112 for processing under the employer's business as usual standard. In this way, the present invention eliminates the need of a third-party server. Further, where POI terminal 110 receives a response from host network 112 (e.g., healthcare information authorized or denied), protocol/sequence controller 314 may provide the network response to RF module 302 for optically and/or audibly communicating the response to fob 102 user.

RFID reader 104 may additionally include USB interface 316, in communication with the protocol/sequence controller 314. In one embodiment, the USB interface may be a RS22 serial data interface. Alternatively, RFID reader 104 may include a serial interface such as, for example, a RS232 interface in communication with protocol/sequence controller 314. USB connector 316 may be in communication with a personalization system 116 (shown in FIG. 1B) for initializing RFID reader 104 to system 100 application parameters. That is, prior to operation of system 100, RFID reader 104 may be in communication with personalization system 116 for populating database 310 with a listing of security keys belonging to authorized fobs 102, and for populating database 320 with the security keys to decrypt fob 102 account identifiers placing the account identifiers in ISO/IEC 7813 format. In this way, RFID reader 104 may be populated with a unique identifier (e.g., serial number) which may be used by fob authentication circuitry 210 to determine if RFID reader 104 is authorized to receive fob 102 encrypted account identifier.

Figure 1B:
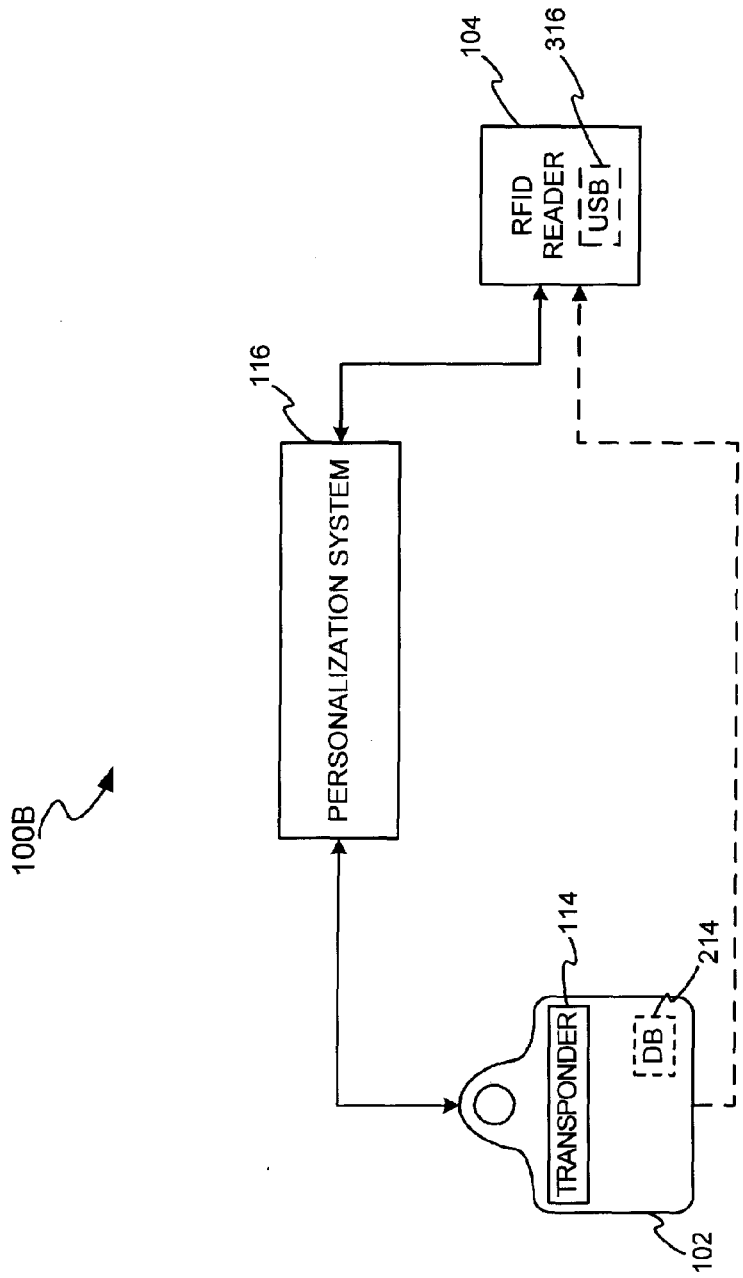
FIG. 1B illustrates an exemplary personalization system in accordance with the present invention.

FIG. 1B illustrates an exemplary personalization system 100B, in accordance with the present invention. In general, typical personalization system 100B may be any system for initializing RFID reader 104 and fob 102 for use in system 100A. With reference to FIG. 1B, the similar personalization process for fob 102 may be illustrated. For example, personalization system 116 may be in communication with fob 102 via RF ISO 14443 interface 114 for populating fob database 212 with the security keys for facilitating authentication of the unique RFID reader 104 identifier. In addition, personalization system 116 may populate on database 212 a unique fob 102 identifier for use by RFID reader 104 in determining whether fob 102 is authorized to access system 100. Personalization system 116 may populate (e.g., inject) the encrypted fob 102 account identifier into fob database 214 for later providing to an authenticated RFID reader 104.

In one exemplary embodiment, personalization system 116 may include any standard computing system as described above. For example, personalization system 116 may include a standard personal computer containing a hardware security module operable using any conventional graphic user interface. Prior to populating the security key information account identifier and unique identifying information into fob 102 or RFID reader 104, the hardware security module may authenticate fob 102 and RFID reader 104 to verify that the components are authorized to receive the secure information.

Figure 6A:
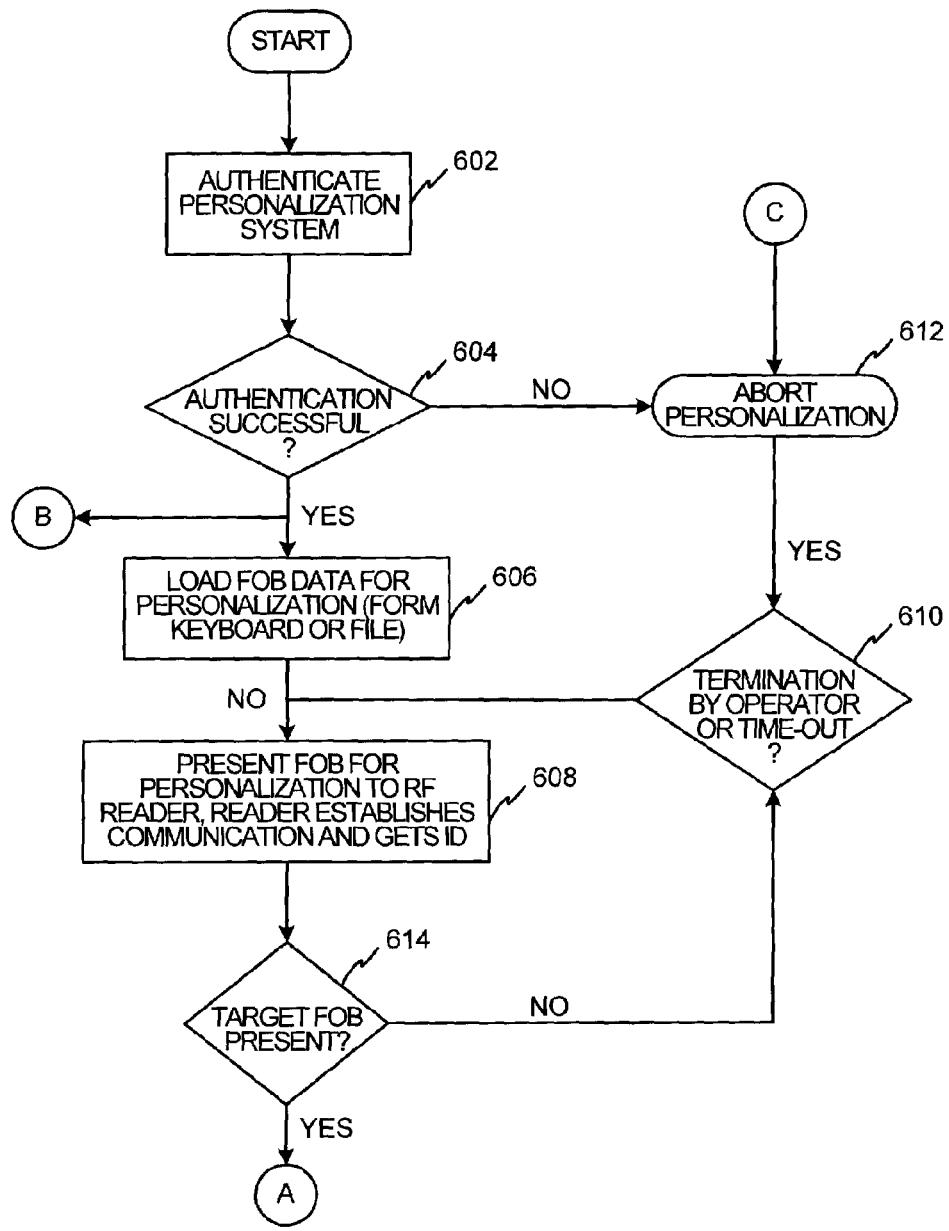
FIGS. 6A-B are an exemplary flow diagram of a fob personalization process in accordance with the present invention.
Figure 6B:
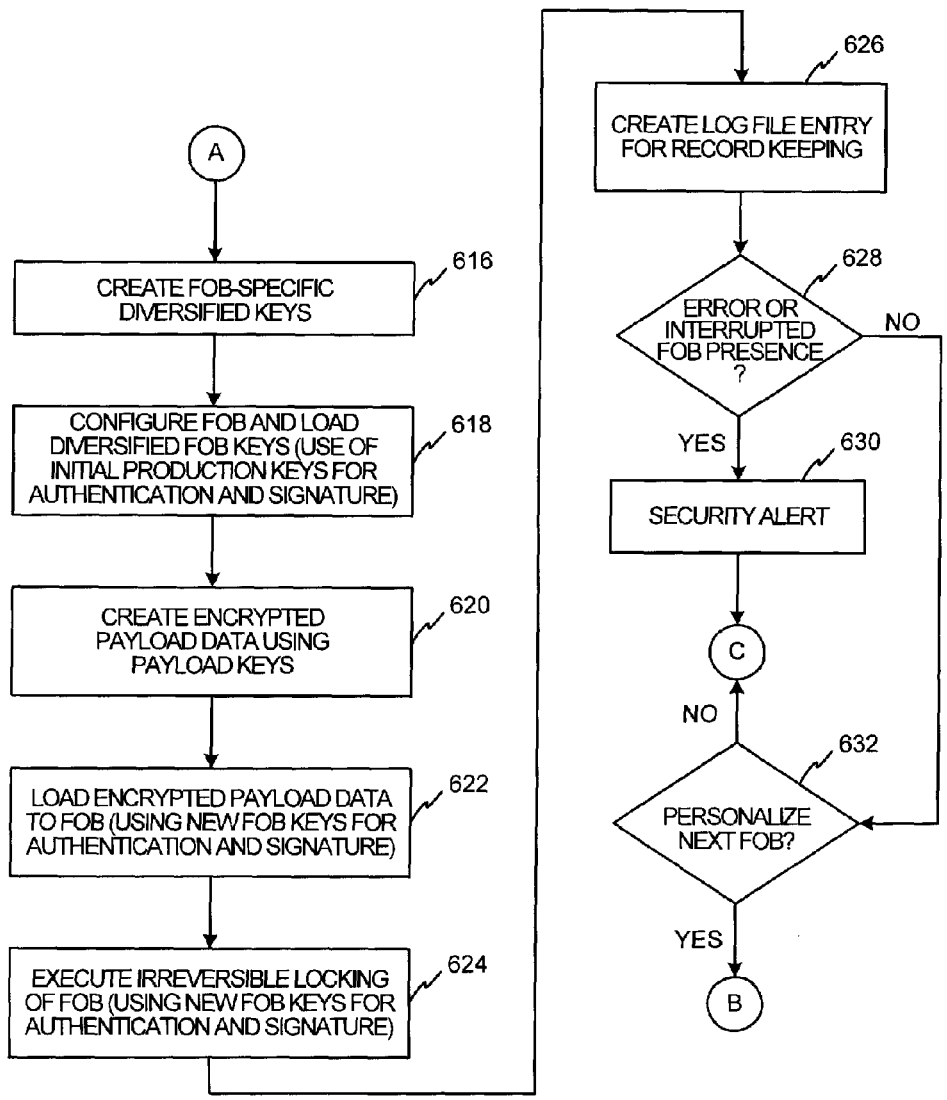

FIGS. 6A-B illustrate an exemplary flowchart of a personalization procedure which may be used to personalize fob 102 and/or RFID reader 104. Although the following description discusses mainly personalization of fob 102, RFID reader 104 may be personalized using a similar process. The personalization process, which occurs between personalization system 116 and the device to be personalized (e.g., fob 102 or RFID reader 104), may begin, for example at step 602. Mutual authentication may occur between personalization system 116 and the device to be authenticated in much the same manner as was described above with regard to fob 102 mutually authenticating with RFID reader 104. That is, personalization system 116 may transmit a personalization system 116 identifier to the device to be authenticated which is compared by the device authentication circuitry 210, 308 against personalization system identifiers stored in the device database 212, 310. Where a match does not occur (step 604), the personalization process may be aborted (step 612). Where a match occurs (step 604), personalization system 116 may prepare a personalization file to be provided to the device to be personalized (step 606). If personalization system 116 is operated manually, the personalization file may be entered into personalization system 116 using any suitable system interface such as, for example, a keyboard (step 606). Where personalization system 116 operator elects to delay the preparation of the personalization files, personalization system 116 may abort the personalization process (step 610). In this context, the personalization file may include the unique fob 102 or RFID reader 104 identifier, security key for loading into database 212 and 310, and/or security keys for decrypting a fob transponder account identifier which may be loaded in database 320.

Fob 102 may be personalized by direct connection to personalization system 116 via RF ISO/IEC 14443 interface 114, or fob 102 may be personalized using RFID reader 104. Personalization system 116 and RFID reader 104 may engage in mutual authentication and RFID reader 104 may be configured to transmit the fob personalization file to fob 102 via RF. Once fob 102 is presented to RFID reader 104 (steps 608, 614) for personalization, fob 102 and RFID reader 104 may engage in mutual authentication (step 614). Where fob 102 is not presented to RFID reader 104 for personalization, the personalization process may be terminated (step 610).

If fob 102 is detected, personalization system 116 may create as a part of the personalization file, a unique identifier for providing to fob 102 (step 616). The identifier is unique in that one identifier may be given only to a single fob. That is, no other fob may have that same identifier. Fob 102 may then be configured and loaded with that identifier (step 618).

The encrypted fob 102 transponder account identifier may be populated into fob 102 in the same manner as is described with respect to the unique fob 102 identifier. That is, personalization system 116 may pre-encrypt the account data (step 620) and inject the encrypted account into fob database 214 (step 622). The encrypted account data may be loaded (e.g., injected) into fob 102 using RFID reader 104 as discussed above.

Once the personalization file is populated into fob 102, the populated information is irreversibly locked to prevent alteration, unauthorized reading and/or unauthorized access (step 624). Personalization system 116 may then create a log of the personalization file information for later access and analysis by the personalization system 116 resource (step 626).

It should be noted that in the event the personalization process is compromised or interrupted (step 628), personalization system 116 may send a security alert to the user (step 630) and the personalization process may be aborted (step 612). On the other hand, where no such compromising or interruption exists, personalization system 116 may be prepared to begin initialization on a second device to be personalized (step 632).

Figure 7A:
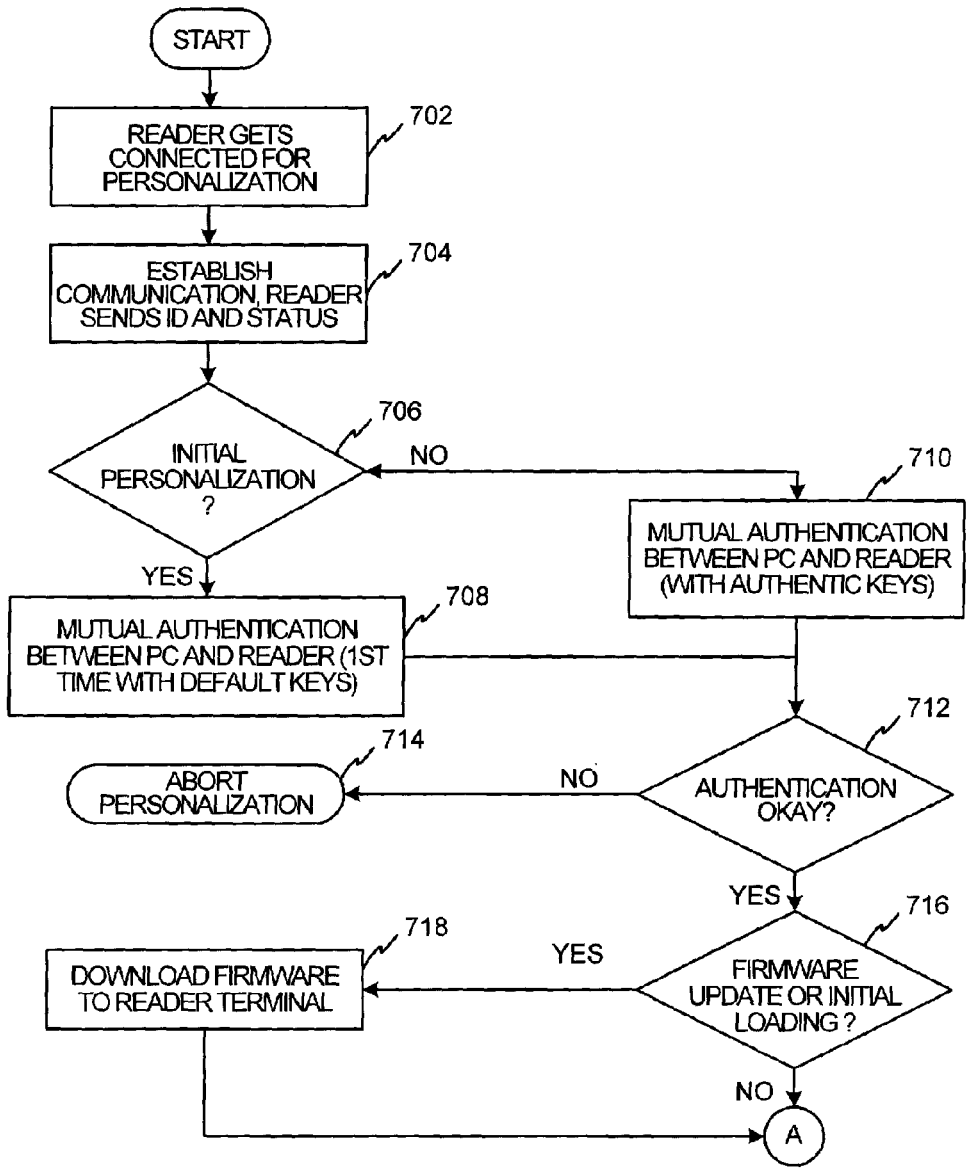
FIGS. 7A-B are an exemplary flow diagram of a RFID reader personalization process in accordance with the present invention.
Figure 7B:
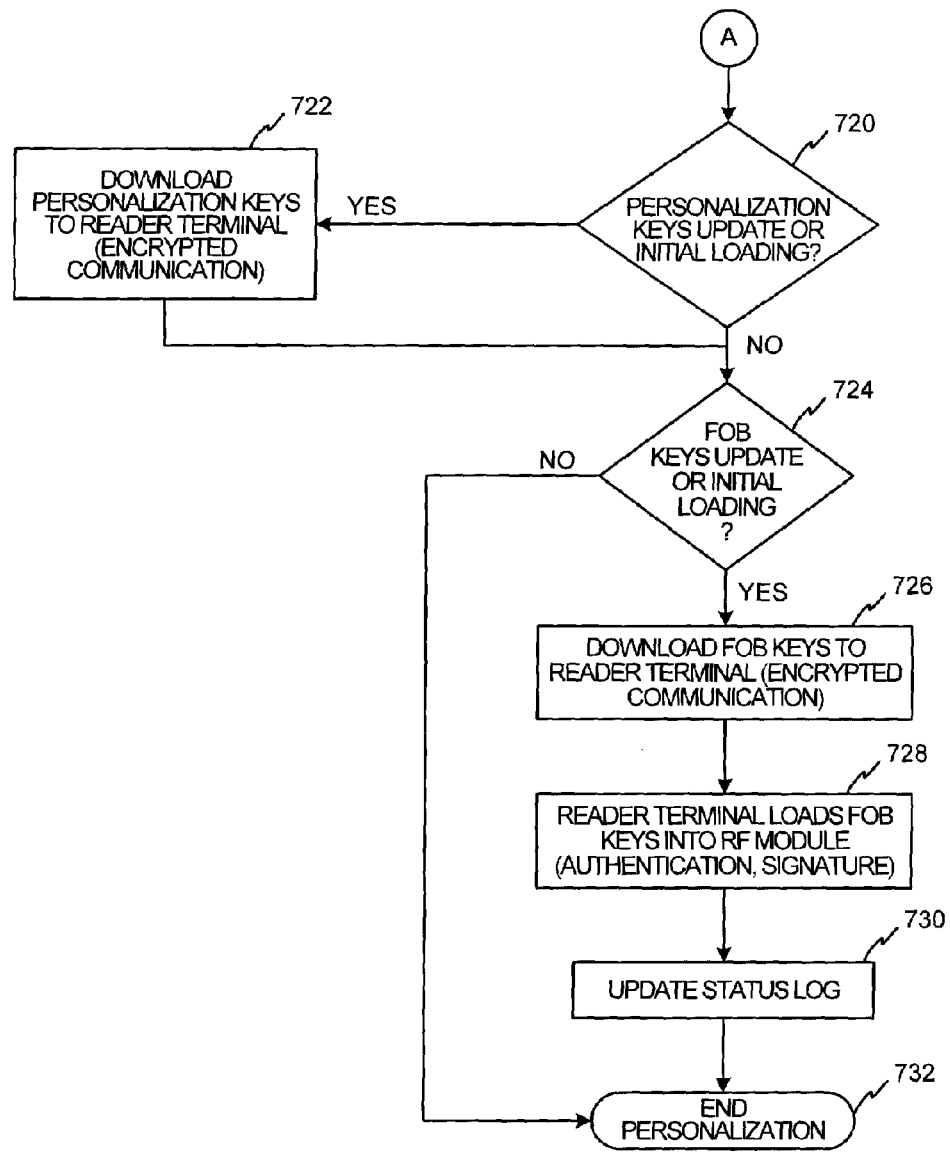

FIGS. 7A-B illustrate another exemplary embodiment of a personalization process which may be used to personalize RFID reader 104. RFID reader 104 may be in communication with personalization system 116 via RFID reader USB connection 316 (step 702). Once connected, personalization system 116 may establish communications with RFID reader 104 and RFID reader 104 may provide personalization system 116 any RFID reader 104 identification data presently stored on RFID reader 104 (step 704). In accordance with step 708, where RFID reader 104 is being personalized for the first time (step 706), RFID reader 104 and personalization system 116 may engage in mutual authentication as described above with respect to FIGS. 6A-B. After the mutual authentication is complete, personalization system 116 may verify that RFID reader 104 is properly manufactured or configured to operate within system 100A. The verification may include evaluating the operation of RFID reader 104 by determining if the RFID reader will accept predetermined default settings. That is, personalization system 116 may then provide RFID reader 104 a set of default settings (step 708) and determine if RFID reader 104 accepts those settings (step 712). If RFID reader 104 does not accept the default settings, personalization system 116 may abort the personalization process (step 714).

If the personalization system 116 determines that the personalization process is not the first personalization process undertaken by RFID reader 104 (step 706), personalization system 116 and RFID reader 104 may engage in a mutual authentication process using the existing security keys already stored on RFID reader 104 (step 710). If authentication is unsuccessful (step 712), personalization system 116 may abort the personalization process (step 714).

Where personalization system 116 and RFID reader 104 successfully mutually authenticate, personalization system 116 may update RFID reader 104 security keys (step 716). Updating the security keys may take place at any time as determined by a system 100 manager. The updating may take place as part of a routine maintenance or merely to install current security key data. The updating may be performed by downloading firmware into RFID reader 104 (step 718). In the event that personalization system 116 determines in step 706 that RFID reader 104 is undergoing an initial personalization, the firmware may be loaded into RFID reader 104 for the first time. In this context, "firmware" may include any file which enables the RFID reader 104 to operate under system 100 guidelines. For example, such guidelines may be directed toward the operation of RFID reader protocol/sequence controller 314.

Personalization system 116 may then determine if the personalization keys (e.g., security keys, decryption keys, RFID identifier) need to be updated or if RFID reader 104 needs to have an initial installation of the personalization keys (step 720). If so, then personalization system 116 may download the personalization keys as appropriate (step 722).

Personalization system 116 may then check RFID reader 104 to determine if fob 102 identifiers and corresponding security keys should be updated or initially loaded (step 724). If no updating is necessary personalization system 116 may end the personalization procedure (step 732). Contrarily, if personalization system 116 determines that fob 102 identifiers and corresponding keys need to be updated or installed, personalization system 116 may download the information onto RFID reader 104 (step 726). The information (e.g., fob security keys and identifiers) may be downloaded in an encrypted format and RFID reader 104 may store the information in RFID reader database 310 as appropriate (step 728). Personalization system 116 may then create or update a status log cataloging for later use and analysis by personalization system 116 user (step 730). Upon updating the status log, the personalization process may be terminated (step 732).

It should be noted that, in some instances it may be necessary to repeat the RFID reader personalization process in a similar manner as described above. In that instance, the personalization process described in FIGS. 7A and 7B may be repeated.

Figure 8:
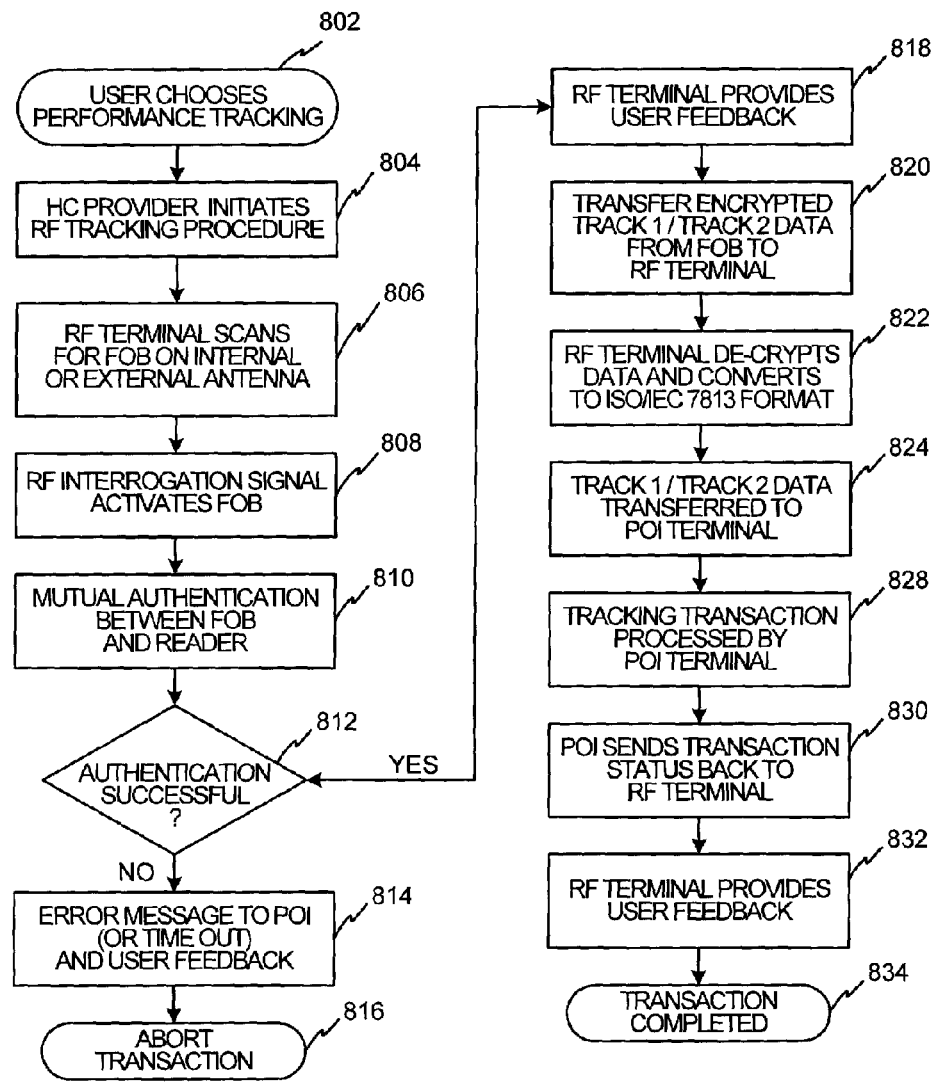
FIG. 8 is a flow diagram of an exemplary healthcare information process in accordance with the present invention.

FIG. 8 illustrates an exemplary flow diagram for the operation of system 100A. The operation may be understood with reference to FIG. 1A, which depicts the elements of system 100A which may be used in an exemplary transaction. The process is initiated when a user desires to present fob 102 for storing and/or accessing user information such as healthcare information (step 802). Upon presentation of fob 102, a healthcare provider initiates the RF healthcare information transaction via RFID reader 104 (step 804). In particular, RFID reader 104 sends out an interrogation signal to scan for the presence of fob 102 (step 806). The RF signal may be provided via RFID reader antenna 106 or optionally via external antenna 108. The RF interrogation signal then activates fob 102 (step 808).

Fob 102 and RFID reader 104 may then engage in mutual authentication (step 810). Where the mutual authentication is unsuccessful, an error message may be provided to the user via the RFID optical and/or audible indicator (step 814) and the healthcare information transaction may be aborted (step 816). Where the mutual authentication is successful (step 812), a transaction will be initiated. That is, RFID reader 104 may provide the user with an appropriate optical and/or audible message (e.g., "healthcare information processing" or "wait") (step 818). Fob protocol/sequence controller 208 may then retrieve from database 214 an encrypted fob account identifier and provide the encrypted account identifier to RFID reader 104 (step 820).

RFID reader 104 may then decrypt the account identifier and convert the account identifier into magnetic stripe (ISO/IEC 7813) format (step 822) and provide the unencrypted account identifier to engine 130 (step 824). In particular, the account identifier may be provided to POI terminal 110 for transmission to host network 112 for processing (step 828). Processing healthcare information will be discussed in greater detail herein. Upon processing, POI terminal 110 may then send an optical and/or audible healthcare information transaction status message to RFID reader 104 (step 830) for communication to the user (step 832). Once the user receives the status message, the transaction is completed (step 834.)

Figure 9:
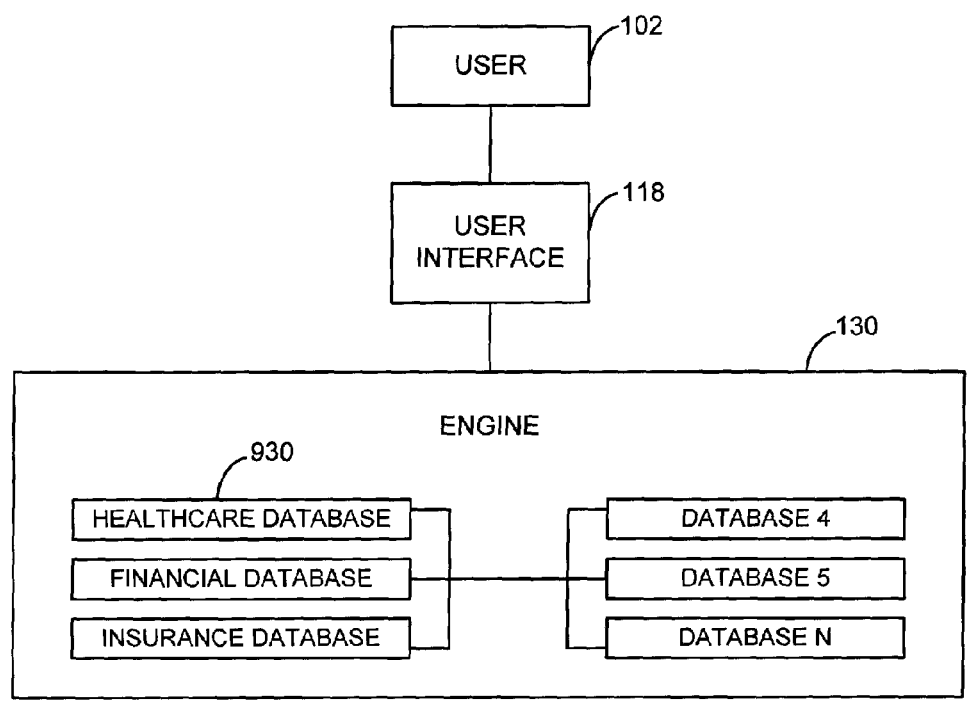
FIG. 9 includes a flowchart illustrating an exemplary healthcare engine system configured to facilitate storing, accessing and transmitting user information.

Processing user information may be achieved by several methods and systems. For example, in accordance with another aspect of the present invention, and with reference to FIG. 9, user 102 may access a remote personal information engine 130 through user interface 118 to facilitate the managing, storing, accessing, and/or other manipulation of user information such as healthcare information.

More particularly, engine 130 may comprise a variety of subprograms and/or databases that facilitate managing, storing, accessing, and/or other manipulation of user information such as healthcare information. Engine 130 may interface with various subprograms or databases, wherein the subprograms may be part of host network 112 and/or network 136. One skilled in the art will appreciate that engine 130 may additionally interface with components directly, through a LAN network or indirectly via any other system or network.

The databases and/or data sets comprising engine 130 may be interconnected such that information from one database and/or data set may be accessed by one, two, three or more other databases and/or data sets. By the term "access," the databases may transmit, receive, obtain, link, view, connect, associate, interface, share, route, acquire, ascertain, retrieve, and/or gain information from one database to another. Thus, any information updated, received and/or sent to one database such as, for example, healthcare database 930, may be automatically updated throughout all or any portion of the other databases that are accessed by healthcare database 930. In addition, the databases comprising engine 130 may be configured with limited access rights/privacy rights. That is, a database owner may permit and/or prohibit other users, owners, issuers, and/or other third parties from accessing information stored on the database.

Figure 10:
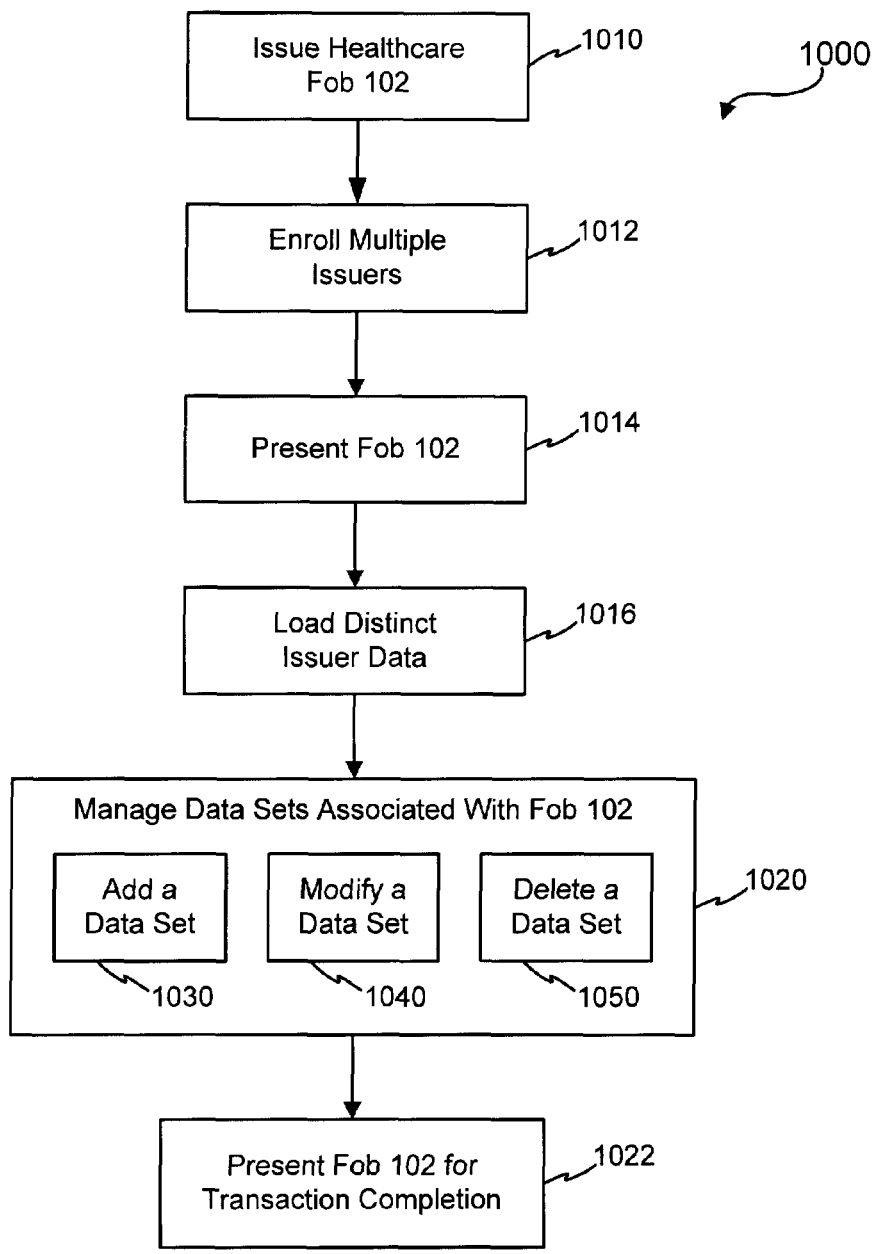
FIG. 10 includes a flowchart illustrating an exemplary method for enrolling and managing multiple data set owners in accordance with the present invention.

In general, systems and methods disclosed herein, are configured to facilitate the management of multiple distinct data sets associated with fob 102. Management of data sets may include such steps as adding, augmenting, updating and/or deleting data sets associated with fob 102. Such manipulations of the data may occur without replacing or reissuing fob 102. With reference to FIG. 10, an exemplary method 1000 according to the present invention is shown. Method 1000 may include issuing a healthcare fob 102 to a fob user (step 1010), enrolling multiple data set owners in a multiple account on fob 102 program (step 1012), and managing data sets associated with fob 102 (step 1020). In managing the data, method 1000 may determine, for example, whether the data should be added to a data set (step 1030), modified (step 1040) or deleted (step 1050), as described more fully below. Once the data is appropriately managed, fob 102 user may present the data contained on fob 102 to a healthcare system for completion of a transaction.

The system may be further configured such that, during an exemplary transaction, data sets associated with fob 102 may be managed. For example, the user may be prompted (e.g., on a screen, by electronic voice, by a store clerk, by a signal and/or the like) as to the possibility of adding, for example, a loyalty account to the same healthcare fob 102 and the user may also be presented with terms and/or conditions in a similar or different manner. The prompt may be configured to activate after the transaction terminal checks for a loyalty account, and discovers that none is present. The user may be prompted at any time during the transaction, and in one embodiment, the user is prompted at the completion of the transaction. If the user accepts the invitation to add data to fob 102, a new data set may be added (step 1030) and/or an existing data set is updated (step 1040). For example, if data is to be updated, the stand alone device may locate appropriate data to be updated on fob 102, and execute the updates ("modifications") in accordance with data owner instructions, and the user, or clerk, may use the POS terminal for the transaction by selecting from a menu. If the data is to be added, the stand alone device may be configured to provide any account information (e.g., account identifier, security code, data owner routing number, etc.) to fob 102 for storage thereon. The stand alone may locate an appropriate (i.e., unused) database location on transaction instrument for storing the added data. The stand alone device facilitates storage of the data in a distinct location on fob 102 database, where the data is stored independently of any other data. In one embodiment of the invention, the data is added to a database location on fob 102 which may be reserved for independently storing all data owned by a particular data set owner (e.g., a BLOB), associated with a key for general data storage. Alternatively, the data may be stored in a distinct location on fob 102, which may be a separate location that is used to store any other data set. Further still, the data set may be stored in accordance with any storage format, and permitting the data to be stored and retrieved independently of other data.

The adding and updating of the data may be verified by the issuer, prior to executing the modifications. That is, the transaction location may be configured to send a message to the issuer, and then the issuer may apply its edit rules before sending a verification (or non-verification). If verified, all databases containing the data set to be updated or a mirror image of the data set to be updated, are modified in accordance with the user or issuer provided instructions, and/or the issuer defined data storage protocol or format.

In one exemplary embodiment, multiple account issuers may be enrolled in a multiple account management program using fob 102 in accordance with the invention (step 1012).

That is, one or more issuers may supply the account number that they are using for the user, along with any other data (either ISO or BLOB). Permission for adding account issuer owned data may be obtained from the data set owner. The data set owner may then be requested to provide account information to be stored on a transaction instrument. The data set owner may then provide account information relative to a distinct user account for loading onto fob 102 in accordance with the present invention. The issuers may be enrolled prior to issuance of fob 102 or the issuers may be enrolled after issuance. By enrolling in the management program, the issuer may provide authorization for including the issuer-owned data on fob 102. The issuer-owned data may be included (e.g., added, deleted, modified, augmented, etc.) on fob 102 using a stand alone interaction device, POI 110, or user personal computer interface upon presentment of fob 102 to the POI 110 (step 1014). POI 110 may manipulate the issuer-owned data while preserving a format recognizable by an issuer account management system (step 1016). For example, POI 110 may identify the appropriate header or trailer associated with the data and add, delete or modify the data accordingly. POI 110 may manipulate the data using any manipulation instruction or protocol as provided by the data set owner so that the resulting manipulated data is still in a format recognizable by the data set owner system. POI 110 may be configured to manipulate the data based on the header. That is, POI 110 may be configured to recognize the format required by the data (e.g. the header describes the format of the data). In this way, POI 110 may manipulate the data while maintaining the data set owner's format. Alternatively, POI 110 may store the issuer-owned data on the fob 102 in any format, provided that the issuer-owned data is provided to the issuer system (or to healthcare system) in an issuer system (or healthcare system) recognizable format.

It should be noted that fob 102 may be issued with or without one or more data sets stored thereon. Fob 102 may be issued using various techniques and practices now known or hereinafter developed wherein an instrument is prepared (e.g., embossed and/or loaded with data) and made available to a user for effecting transactions. Although the present invention may contemplate managing data sets (step 1020) before issuing fob 102 (step 1010), in various exemplary embodiments, by way of illustration, the data sets are described herein as being managed (step 1020) after issuance (step 1010).

At any time after issuance (step 1010) of the healthcare fob 102, fob 102 may be used in a healthcare and/or commercial transaction. In one exemplary embodiment, a user communicates with a healthcare provider, indicates a desire to participate in a issuer/healthcare provided healthcare program. The user may communicate with the healthcare provider by, for example, presenting fob 102 to the healthcare provider and indicating a desire to complete a healthcare transaction. The healthcare data may be preloaded on fob 102. The user may indicate his desire to complete a transaction using any conventional process used by the healthcare provider. The user may further indicate that the user wishes to complete the transaction using fob 102. During completion of the transaction, the user may present fob 102 to a healthcare provider system (step 1022). Fob 102 is configured to communicate with the healthcare provider, using any conventional method for facilitating a transaction over a network.

In various exemplary embodiments, the steps of adding, deleting, augmenting, and/or modifying data sets may be repeated. For example, first, second, and additional data sets may be added (step 1030) to fob 102 in any order. In one exemplary embodiment of the present invention, the first data set is owned by a first data set owner (i.e., first issuer) and the second data set is owned by a second data set owner (i.e., second issuer). Furthermore, the system may include replacing any portion of a first data set with any portion of a subsequent data set by deleting any portion of a data set (step 1050), then adding any portion of a data set (step 1030).

Figure 11:
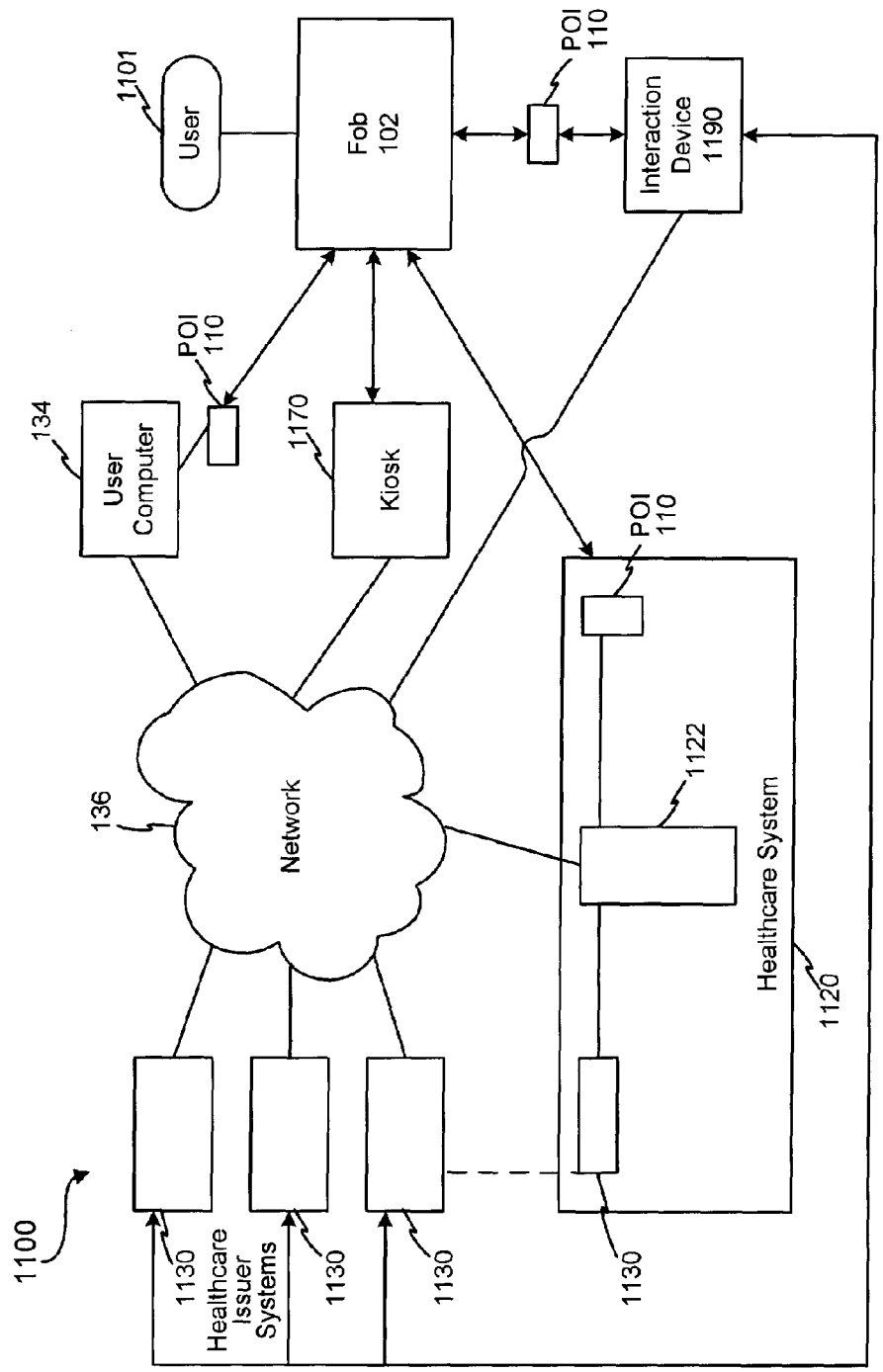
FIG. 11 includes a depiction of an exemplary data set management system in accordance with the present invention.

With reference now to FIG. 11, in one exemplary embodiment, a data set management system ("management system") 1100 comprises a healthcare system 1120, various healthcare issuer systems 1130, and fob 102. Management system 1100 may further be accessed by a user 1101 on a self-service interaction device, such as, for example, user computer 134 or via a transaction device such as, for example, one or more POIs 110, kiosk 1170, stand-alone interaction device 1190, automated teller, or the like. Healthcare issuer systems 1130 are configured to interact with fob 102 to receive and/or exchange data facilitating a transaction. Healthcare system 1120 may be operated, controlled and/or facilitated by any hospital, healthcare provider, medical entity, or merchant that facilitates the transfer of data and/or payment to fob 102.

The self-service user interaction device may be any device suitable for interacting with fob 102, and receiving information from fob 102 user and providing the information to a healthcare provider, insurance carrier, merchant, account issuer, account manager, data set owner, hospital point-of-interaction and the like. For example, a user may use a self-service device configured with a PC to provide healthcare information to a physician via a website (e.g., WebMD®) to obtain medical care. In one example, the self-service user interaction device may be configured to communicate information to and from the transaction device and to manipulate the data sets stored thereon. The self-service interaction device may be in communication with the various components of the invention using any suitable communications protocol.

The self-service interaction device may be initialized prior to use. For example, the self-service interaction device may be any system which may be initialized ("configured") to communicate with healthcare system 1120. Where the self-service interaction device is not initialized prior to attempting communications with the healthcare system 1120 or fob 102, the self-service interaction device may be initialized at the healthcare system 1120 location. The interaction device may be initialized using any conventional method for configuring device communication protocol.

User 1101 may communicate with the healthcare provider and/or healthcare system 1120 in person (e.g., at the hospital), or electronically (e.g., from a user computer 134 via network 136 and/or network 112). During the interaction, the healthcare provider and/or healthcare system 1120 may offer healthcare services and/or products to user 1101 and/or transmit and/or receive information from user 1101. The healthcare provider and/or healthcare system 1120 may also offer user 1101 the option of completing the transaction using fob 102. The healthcare provider and/or healthcare system 1120 may provide the options to user 1101 using interactive user interface, suitable website or other Internet-based graphical user interface that is accessible by users.

Healthcare issuer systems 1130 may be configured to manipulate a transaction account associated with the corresponding issuer-owned data stored on fob 102 (or database 214, discussed herein) in accordance with a related transaction. For example, healthcare issuer system 1130 may receive "transaction information" and manipulate an account status or balance in accordance with the information received. In accordance with the transaction amount, healthcare issuer system 1130 may, for example, diminish a value available for completing a transaction associated with the account, or healthcare issuer system 1130 may alter the information relative to the account user (e.g., medical insurance information, personal information, etc.).

It should be noted that healthcare issuer systems 1130 may also be configured to interact with fob 102, directly or indirectly via database 214, POI 110, and/or interaction device 1190 to individually manage data sets on fob 102. For example, healthcare issuer systems 1130 may manage data sets on database 214. In some embodiments, the data sets on database 214 may then be stored on fob 102 when fob 102 is presented. In other embodiments, healthcare issuer systems 1130 may store data set information within their own systems which may communicate with fob 102 via user computer 134, kiosk 1170, or healthcare system 1120. In such embodiments, healthcare issuer system 1130 may be configured to push the data set to the fob 102 via the POI 110, or healthcare system 1120, kiosk 1170, interaction device 1190 or computer 134 which may be configured to pull such information from healthcare issuer system 1130.

POI 110 and/or interaction device 1190 may provide instructions to the healthcare issuer systems 1130 for requesting receipt of issuer-owned data, such as for example, account data, user identification data, user demographic data, user insurance data or the like, which the issuer wishes to store on fob 102. POI 110 and/or interaction device 1190 may communicate with healthcare issuer systems 1130 using an issuer recognizable communications protocol, language, methods of communication and the like, for providing and receiving data. In one exemplary embodiment, issuer-owned data is received by POI 110 and/or interaction device 1190 from healthcare issuer systems 1130, and stored onto the fob 102. In one exemplary embodiment, the issuer-owned data is stored using healthcare issuer system 1130 format which may be later formatted in healthcare system 1120 recognizable protocol when provided to the healthcare system 1120. In one embodiment, the issuer-owned information is stored on fob 102 in the identical format with which it was provided by healthcare issuer system 1130.

In a typical example of healthcare issuer modification of the data sets, one or more data sets may be modified by healthcare issuer system 1130 directly via the healthcare issuer systems 1130, upon presentment of fob 102 to system 1130. That is, user 1101 may present fob 102 to healthcare issuer system 1130, and healthcare issuer system 1130 may modify the issuer data stored thereon, using any issuer defined protocol. Alternatively, the modifications, or instructions for modification, may be initiated at healthcare issuer system 1130, and provided to network 136. The modifications and/or modification instructions may additionally be provided to a suitable device configured to communicate with fob 102, receive information regarding the data stored on fob 102, and to write or overwrite the information contained on fob 102. For example, as noted, POI 110 and/or interaction device 1190 may be suitable interaction devices which may be used to provide information to fob 102 to modify the information stored thereon. POI 110 and/or interaction device 1190 may be any devices capable of receiving data management instructions from healthcare issuer systems 1130 and for updating the data stored on fob 102, in accordance with the instructions received. In this regard, POI 110 and/or interaction device 1190 may include any electronic components, databases, processors, servers and the like which may be used to modify the data stored on fob 102 using any suitable data modification protocol as is found in the art. Preferably, POI 110 and/or interaction device 1190 is configured to modify the data on fob 102 in accordance with a data owner defined protocol.

In one exemplary embodiment, POI 110 and/or interaction device 1190, may be configured to modify fob's 102 issuer-owned data when fob 102 is initially configured, prior to providing fob 102 to user 1101. POI 110 and/or interaction device 1190 may additionally be configured to modify the issuer data on fob 102 when fob 102 is next presented, for example, to POI 110. In this regard, POI 110 and/or interaction device 1190 may receive from multiple distinct healthcare issuer systems 1130, via the network 136, the issuer provided modifications/instructions and may update fob 102 in real-time or substantially real-time. The modifications may be provided to POI 110 and/or interaction device 1190 for storage and later use when fob 102 is next presented. Alternatively, POI 110 and/or interaction device 1190 may be configured to retrieve the instructions from healthcare issuer system 1130 when fob 102 is next presented to POI 110 and/or interaction device 1190. Further, where other devices, such as, for example, kiosk 1170, or the like, are likewise configured to modify the issuer data on fob 102, the invention contemplates that the real-time or substantially real-time modifications noted above may be made using those devices in similar manner as is described with POI 110 and/or interaction device 1190.

Alternatively, the device to which fob 102 may be presented, may not be equipped for updating or modifying the data stored on fob 102. For example, healthcare system 1120 may be any conventional healthcare provider system which communicates to healthcare issuer system 1130, and which permits user 1101 to complete a financial transaction, but which is not configured to modify the healthcare issuer data contained on fob 102. In general, conventional healthcare provider systems are not configured to write or overwrite data included on fobs 102 presented to the healthcare provider system for processing. That is, healthcare system 1120 may include little or no additional software to participate in an online transaction supported by network 136. Management of the data sets on fob 102 may be performed independent of the operation of healthcare system 1120 (e.g., via healthcare issuer system 1130 or interaction device 1190). As such, the present invention may require no retrofitting of healthcare system 1120, to accommodate system 1100 operation. Thus, where healthcare system 1120 is not configured to modify the data on fob 102, such modifications may be executed as described above with respect to modifications being executed at interaction device 1190, POI 110 and/or by the issuer at healthcare issuer 1130 system.

Healthcare system 1120, kiosk 1170, interaction device 1190, and/or POI 110 may include additional systems and methods for permitting fob 102 user 1101 to self-manage the data stored on fob 102. In this case, the systems 1120, 1170, 1190 and 110 may include an additional user interface for use by user 1101 to identify the modification action to be taken. Where the systems 1120, 1170, 1190 and/or 110 are configured to communicate with fob 102 and to modify the data thereon, the modifications may be completed or substantially completed in real-time or substantially real-time. For example, user 1101 may present fob 102 to one of systems 1120, 1170, 1190 and 110, provide instructions to systems 1120, 1170, 1190 and/or 110 for modifying the data on fob 102. The instructions may include, for example, "ADD," "DELETE," MODIFY," and systems 1120, 1170, 1190 and/or 110 may modify the data stored on fob 102 in accordance therewith. These instructions will be described in greater detail herein. The modifications may be made on fob 102 in real-time or substantially real-time, for example, prior to permitting fob 102 to be used by user 1101. Alternatively, the modifications or instructions for modification may be provided by user 1101 to healthcare system 1120 or kiosk 1170, and healthcare system 1120 or kiosk 1170 may further provide the modifications/instructions to network 136 for use in later modifying the data. For example, the modifications/instructions may be provided by system 1120 and/or 1170 to healthcare issuer system 1130 managed by the issuer owning the data to be modified. Healthcare issuer system 1130 may provide the modifications to, for example, interaction device 1190, for updating fob 102 when next presented. The modifications/instructions may additionally be provided from network 136 to a remote database, where the issuer-owned data corresponding to fob 102 and the issuer may be additionally stored (i.e., on engine 130, described herein). In one exemplary embodiment, the modifications/instructions may be stored at healthcare issuer system 1130, until such time as fob 102 is next presented to a device configured to modify the data on fob 102. Once presented, the modifications/instructions may be provided to the device (e.g., computer 134, interaction device 1190, etc.) for modifying fob 102 data.

In another exemplary embodiment, user 1101 may self-manage the data sets by, for example, modifying the data sets using a conventional computer system 134, which may be in communication with network 136. Computer system 134 may or may not be configured to interact with fob 102. Where computer system 134 is not configured to interact with fob 102, user 1101 may provide modifications or instructions to healthcare issuer system 1130 for later use in modifying the corresponding fob 102 data, for example, when fob 102 is next presented in similar manner as described above. Where computer 134 is configured to interact with fob 102 to modify the data stored thereon, user 1101 may provide modifications/instructions to computer 134 for modifying the data on the financial instrument in real-time or substantially real-time. That is, computer 134 may be configured to interact with, read, add, delete, and/or modify the data sets on fob 102. Consequently, computer 134 may receive modifications/instructions from user 1101 and perform the modifications accordingly, and may modify the data in real-time or substantially real-time. User computer 134 may additionally be configured to receive authorization of the modifications/instructions from healthcare issuer system 1130 prior to executing user 1101 requested changes. In one exemplary arrangement, user 1101 may provide the modifications/instructions via network 136 which may be additionally provided to healthcare issuer system 1130. Healthcare issuer system 1130 may receive user 1101 modifications/instructions and verify whether the identified updates are available to user 1101 or if the identified updates are valid. If the identified updates are authorized, healthcare issuer system 1130 may update a data storage area associated with fob 102. For example, healthcare issuer system 1130 may update an issuer database (not shown) containing data corresponding to the issuer-owned data associated with fob 102. Alternatively, healthcare issuer system 1130 may provide modifications/instructions to a database positioned remotely to healthcare issuer system 1130 for use in modifying the data stored thereon, which is associated to fob 102. As such, in accordance with the present invention, user 1101 may self-manage the data via, for example, user computer 134, kiosk 1170, healthcare system 1120, and/or a POI 110.

In one exemplary method of self-management, user 1101 logs onto a website via user computer 134, or onto a stand alone device, such as, for example, interaction device 1190 or kiosk 1170, and selects options for configuring data sets on fob 102. The changes may be transmitted to fob 102 RFID reader 104 configured to communicate the data to fob 102. In this context, RFID reader 104 may be any conventional transponder device reader or writer.

As noted, modifications to the data stored on fob 102 may be made in real-time, substantially real-time or batch process when fob 102 is presented to interaction device 1190, POI 110 and/or to RFID reader 104. However, as noted, various embodiments of the invention include a remote database 930 on engine 130 in communication with healthcare issuer system 1130 via network 136. The remote database 930 may additionally be in communication with one of user computer 134, kiosk 1170, healthcare system 1120 and/or interaction device 1190, for variously receiving modifications or instructions for performing modifications to the data stored thereon. In addition, database 930 may contain a data storage area which "mirrors" the data stored on fob 102. In this context "mirrored" or "mirror" may mean that the data is stored on database 930 in substantially identical configuration and format as stored on fob 102. As such, the present invention may be configured to permit modifications made to fob 102 data to be mimicked on corresponding data locations on database 930. For example, user 1101 may self-manage the data on database 930 via a user interface in communication with database 930 via network 136. In one exemplary embodiment, user 1101 may communicate with a "website" which is used to manage database 930, wherein database 930 is a database including unique locations for storing the issuer provided data and data sets correlative to the data and data sets stored on fob 102. The website may include an account management application which permits user 1101 to select which user accounts to add, delete, or modify with respect to fob 102. That is, user 1101 may provide unique identifying information to user computer 134 which may be recognized by the system (e.g., healthcare issuer system 1130 and/or remote system managing database 930) thereby permitting user 1101 to access the data corresponding to the unique identifying information stored on database 930. Further, prior to permitting modifications to database 930, the issuer owning the data may require authorization that such modifications may be performed. Further still, the present invention contemplates that database 930 may be self-managed by user 1101 in a similar manner, where healthcare system 1120, kiosk 1170 and/or interaction device 1190 are configured to provide modifications/instructions to the healthcare issuer systems 1130 and database 930.

As noted, in some exemplary embodiments of the invention, authorization must be obtained from healthcare issuer systems 1130 prior to executing any modifications to the data contained on fob 102 and/or database 930. Authorization may be obtained by requesting the authorization during the modification process. Authorization may be given where user 1101 provides the more appropriate security information, which is verified by healthcare issuer system 1130. The security information may be, for example, a security code granting access to the issuer-owned data on fob 102 or database 930. For example, POI 110 and/or RFID reader 104 may be configured to allow the input of a code, or an answer to a prompt which is provided to and verified by healthcare issuer system 1130. Once verified the modification requested may be made to the data contained on fob 102.

It should be noted that the authorization code may be used to permit user 1101 to select which issuer provided data to utilize for completion of a transaction. For example, POI 110 and/or RFID reader 104 may be programmed to search fob 102 for a data set containing a particular insurance data set, or to locate all available data sets for providing to user 1101 display available data sets to user 1101, thereby permitting user 1101 to select which data set to use to complete a healthcare transaction. If no data set is found, POI 110 and/or RFID reader 104 may alert user 1101 or prompt the healthcare provider to alert user 1101 of the possibility of adding issuer-owned data to fob 102. A positive response to this alert may cause POI 110 and/or RFID reader 104 to add an issuer data set to fob 102.

It is noted that user 1101 may already be a carrier of a certain type of insurance and/or healthcare program managed by a healthcare issuer system 1130 in which case the associated user 1101 insurance data may be assigned to user 1101 for inclusion on fob 102. As such, user 1101 may be permitted to add the insurance data set to fob 102. Alternatively, the user may become an insurance holder by selecting to add the insurance information to fob 102, using, for example, interactive device 1190. In some embodiments, changes made to the data sets stored on fob 102 may be updated to fob 102 in real-time or substantially real-time, where device 1190 is in communication with fob 102. Or the changes may be made the next time user 1101 presents fob 102 to POI 110, RFID reader 104 or to kiosk 1170, healthcare system 1120, or the like.

In another exemplary embodiment of the present invention, healthcare system 1120, kiosk 1170, and/or user computer 134 may be configured to interact with fob 102 via RFID reader 104.

In exemplary embodiment, management of data sets is facilitated by annotating the data set with a status indicator (e.g., condition header); (e.g., LOADED, INITIALIZED, READY, BLOCKED, REMOVABLE or DELETED).

In this regard, a data set may have a LOADED status when the information related to that data set has been stored in association with fob 102, but remains dormant. For example, an insurance account may have been added to fob 102 that has not yet been activated. In some instances, the loaded data set needs to be further configured before it is ready to be used. For example, the data set may be modified to include a particular hospital in a chain of hospitals, the identification of user's 1101 primary care physician, or to reflect user's 1101 medical allergies. In another example, a particular healthcare program may be added in association with fob 102, and the data set marked LOADED. In another example, user 1101 may interact with kiosk 1170 or the like to input personal information and configure the healthcare program data set. Once such a data set has been configured, it may be annotated with an INITIALIZED status.

The status of a data set may be set as READY when the data set is ready to be utilized. For example, user 1101 may enter a secret code to indicate that user 1101 is ready to use the data set. In one example, the data set may be marked as READY when that data set is first accessed to receive a healthcare service. It will be noted that in accordance with other embodiments of the present invention, the status of a data set may be set at READY the moment it is loaded to fob 102. Furthermore, it is possible to change the status between READY, LOADED, and INITIALIZED, under appropriate circumstances. Thus, the data sets may be managed through any one or more of these states and in various orders.

It may also be desirable to prevent use of a data set and/or the associated functionality for a period of time. Thus, the status indicator may be set to BLOCKED. The setting of the status indicator to BLOCKED may, for example, disable the use of the data set. In one exemplary embodiment, an appropriately configured RFID reader 104 may be configured to recognize the BLOCKED status indicator when accessing the data set and to prevent use of that data set example.

In addition, for various reasons, user 1101 may desire to remove a data set from fob 102. User 1101 may, for example, desire to use the available space on fob 102 for other data sets, or may remove the data set for security reasons. Furthermore, circumstances may arise where the owner of the data set desires to remove the data set from one or more fobs 102, such as when a insurance program expires. In these instances, the data set may be marked as REMOVABLE. Under these circumstances, the memory associated with the data set is available to receive information associated with future added data sets, but for the moment retains the old data set. A REMOVABLE data set may again be made READY under various configurations.

The REMOVABLE data set may subsequently be removed from fob 102 and marked DELETED. A DELETED status indicator may be used to indicate that a portion of fob 102 is available to store one or more data sets. It is noted that data sets may be directly deleted without going through the step of making the data set REMOVABLE. In one example, a data set may be removed from fob 102 if the security of the account associated with the data set is compromised (e.g., stolen password). Furthermore, as appropriate, the status of data sets may be changed to different states. Under appropriate circumstances one or more of any of the six status indicators LOADED, INITIALIZED, READY, BLOCKED, REMOVABLE, or DELETED or other suitable status indicators may be used to annotate a BLOB or other similar data set.

Although the data sets described herein may be managed without status indicators, nevertheless, such status indicators facilitate management of data. For example, regardless of a first data set owner's ability to interpret the information stored in a data set owned by another party, the first owner may interpret the status indicator to determine whether the data set is LOADED, DELETED, or the like. The determination that a data set is DELETED facilitates the addition of new data sets by independent owners without overwriting other data sets on fob 102. In addition, the use of tags or status indicators may facilitate the use of global rules, which may simplify operations and/or commands. Status indicators may also enhance interoperability between data sets. Nevertheless, a data set owner may chose not to use a status indicator even if the opportunity is available.

Figure 12:
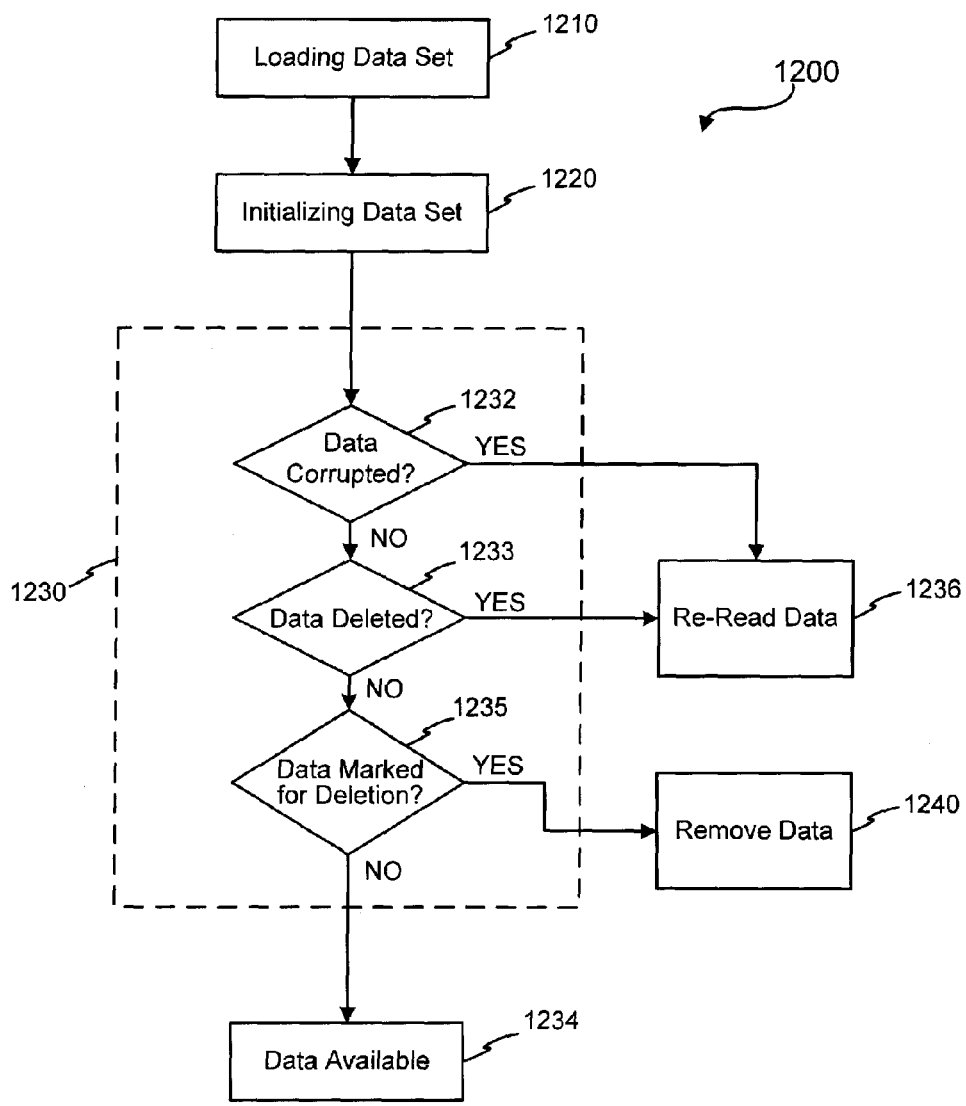
FIG. 12 illustrates a general overview of an exemplary data set management method in accordance with the present invention.

FIG. 12 illustrates a general overview of an exemplary data set management method 1200 comprising the steps of: loading a data set (step 1210), initializing a data set (step 1220), verifying availability of data set (step 1230), and deleting a data set (step 1240). In this manner, a data set may be added to fob 102 and utilized until it is deleted. The adding and deleting steps are described in further detail with reference to FIGS. 13 and 19. Furthermore, the ability to update, modify, replace and/or delete a data set may be subject to security requirements.

In one embodiment, the various processes may include user 1101 facilitating the input of information into a data management system to cause the data set to be loaded. The information may be inputted by fob 102, keypad, magnetic stripe, smart card, electronic pointer, touchpad and/or the like, into a user computer 134, POI terminal 110, kiosk 1170, ATM terminal and/or directly into healthcare system 1120 via a similar terminal or computer associated with healthcare provider server 1122. The information may be transmitted via any network 136 discussed herein to healthcare system 1120 or healthcare issuer systems 1130. In another embodiment, the healthcare provider may enter the information into healthcare issuer system 1130 on behalf to user 1101. This may occur, for example, when user 1101 and/or healthcare issuer system 1130 authorizes the management of data sets on fob 102 over a telephone and the service representative inputs the information. In this embodiment, fob 102 may be updated at the next presentment opportunity such as when user 1101 attempts to compete a transaction using fob 102.

Any suitable procedures may be utilized to determine whether a data set is currently ready for use and available (step 1230). In one example, when fob 102 is presented, the availability of the data set is verified by checking whether the data set has been corrupted or blocked (step 1232), or deleted (step 1233). For example, the data set may be checked to determine if the data set has been accessed or altered without permission ("corrupted") or if the data set exists or has been removed from fob 102 ("deleted"). The check may be performed using any suitable protocol or comparing data. If the answer to these questions is no, then the data set is available and ready for use (step 1234). If the data is corrupted or blocked, subroutines may be used to attempt to retry reading the data (step 1236). If the data set is marked deleted or removable, subroutines will prevent access to the data set (step 1235) and remove the data set (step 1240). For example, a suitable subroutine may place a DELETE "marker" on the data set which prevents the data from being transmitted during completion of a healthcare transaction. The data set may then be marked for deletion and deleted from fob 102 at the next presentment of the device. In similar manner, where the data set is corrupted, a CORRUPTED marker may be appended to the data set and the data set is prevented from being transmitted during completion of a healthcare transaction. The marker may be a header or trailer as discussed herein.

Figure 13:
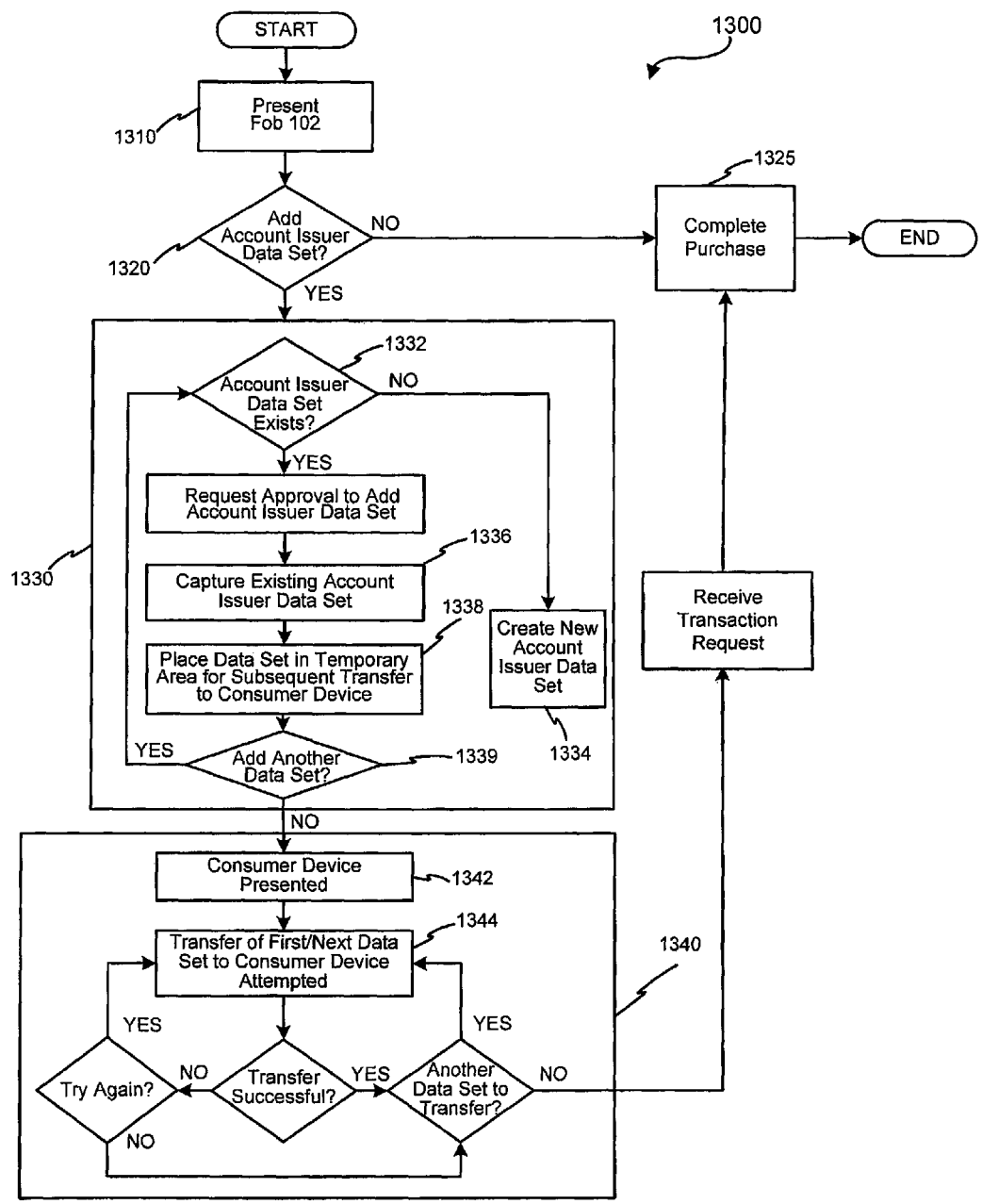
FIG. 13 illustrates an exemplary method of adding a data set to a fob in accordance with the present invention.

Various methods may be used to add a data set to fob 102 or to replace a data set on fob 102. FIG. 13 illustrates an exemplary method of adding a data set to fob 102, including the general steps of presenting fob 102 (step 1310), verifying the addition of the data set to fob 102 (step 1320), placing the data set in a temporary holding area (step 1330), and adding the data set (step 1340).

More particularly, user 1101 presents fob 102 (step 1310) to RFID reader 104 configured to communicate with fob 102. User 1101 may present fob 102 at a point-of-purchase or to an interaction device 1190 and/or kiosk 1170. For example, user 1101 may wave fob 102 in front of POI 110 in a hospital, which is configured to receive data from fob 102. Alternatively, user 1101 may present fob 102 at a self-service location such as a kiosk 1170 in a mall. Moreover, user 1101 may present fob 102 to a peripheral device associated with a personal computer, or the like.

User 1101 is then given the opportunity to add a data set to fob 102. For example, RFID reader 104 may detect the absence of a particular data set on fob 102 by searching fob 102 data base and comparing the existing data sets to the data set to be added. If the data set to be added is not found on the data base, user 1101 may be prompted to confirm the addition of this data set to fob 102 (step 1320). The user may be prompted via an interactive user interface displaying the option to add the data set. In one example, when user 1101 presents fob 102 to a healthcare provider, RFID reader 104 may detect the absence of an insurance data set and provide a message on a display to user 1101 or the hospital clerk indicating that the insurance data set can be added if desired. User 1101 may answer in the negative and complete the healthcare transaction using typical transaction methods (step 1125). Alternatively, if user 1101 provides an affirmative response, the algorithm may prepare a data set for communication with fob 102 (step 1130). The process may determine whether the data set (or information that could be used to create the data set) exists in some form or on some device other than on fob 102 (step 1132). Determining whether a data set exists may involve querying a healthcare issuer system 1130, database 930, or the like. For example, healthcare issuer system 1130 may compare the data set to other data sets healthcare issuer system 1130 has assigned to a particular user 1101. If the data set is not assigned to a particular user, then issuer system may determine that the data set is available for adding to fob 102. Determining whether a data set exists may also take place when a store clerk verbally asks (or a screen prompts) user 1101 to present an insurance card containing the information. For example, the data set may exist on a an insurance card, it may be stored in magnetic stripe form, bar code, and/or the like.

If the data set exists in an accessible form, the data set may be captured (step 1336). In this example, user 1101 may present the insurance card and the data read from the insurance card may then be stored in a data set associated with fob 102. For example, user 1101 may desire to add a dental insurance card to the user's 1101 fob 102. User 1101 may swipe, scan or otherwise present the dental insurance card such that the data set from the dental insurance card is captured. The system may be further configured such that the healthcare provider, kiosk 1170, or computer system may access healthcare issuer system 1130 to obtain information for creating the data set. Thus, if user 1101 does not have the insurance card on user's 1101 person, system 1130 may prompt the clerk to request identifying/security information and to access the user's 201 account and therefore facilitate adding an insurance data set associated with user's 1101 fob 102. Any other suitable methods of capturing data sets may also be used.

If the data set does not exist, a new data set may be created (step 1334) for inclusion on fob 102. Creation of the data set may, for example, involve filling out an application, providing name and address, creating an account, and/or the like. In either event, the pre-existing or newly created data set is temporarily held in a storage area (e.g., database 930, local memory or the like) for transfer to fob 102 (step 1338). Additional data sets may be prepared for transmittal to fob 102 (step 1339).

In this exemplary embodiment, fob 102 is presented again to RFID reader 104 (step 1342). RFID reader 104 is configured to attempt to transfer the data set(s) to fob 102 (step 1344). For example, existing RFID reader 104 may be configured with software and/or hardware upgrades to transmit data to fob 102. In one exemplary embodiment, if the data sets were not transferred correctly, the process may try the transfer again. In another exemplary embodiment, data sets are added one at a time or altogether. Thus, user 1101 may wave fob 102 past RFID reader 104 one or more times during the addition process. The transaction may be completed (step 1325) using the new data set or another selected method of payment. The same steps may be used in a self-service embodiment, however, in one embodiment, no healthcare transaction takes place along with the addition of data sets. It should also be noted that under appropriate circumstances, user 1101 could add data sets at a point-of-interaction without actually completing a transaction.

In various exemplary embodiments, user 1101 and/or the owner of the data set may manage the data set (i.e., steps 1332-1339) in advance of presenting fob 102. For example, user 1101 on user computer 134 may choose to add or delete data sets via a website configured for management of data sets. In another example, healthcare issuer system 1130 may add functionality to an account and may desire to update the data set associated with that account. In either example, data sets that have been prepared in advance, may be ready for transmission upon presentment of fob 102. The transmission of the data sets may be transparent to user 1101. For example, user 1101 may present fob 102 (step 1342) to complete a healthcare transaction and the waiting data sets may automatically be added to the user's 1101 fob 102 (step 1340).

Similar steps may be taken to replace or update data sets with new information. For example, user 1101 at a point-of-interaction may be informed of an upgrade in functionality associated with an account or other data set. Following similar steps as discussed with reference to FIG. 13, the existing data set on fob 102 is replaced with a new data set. Moreover, depending on permission rights and/or hierarchies in place, if any, an existing data set may be replaced with an unrelated data set. Other methods of adding and replacing data sets may also be used to manage data sets on fob 102.

Figure 19:
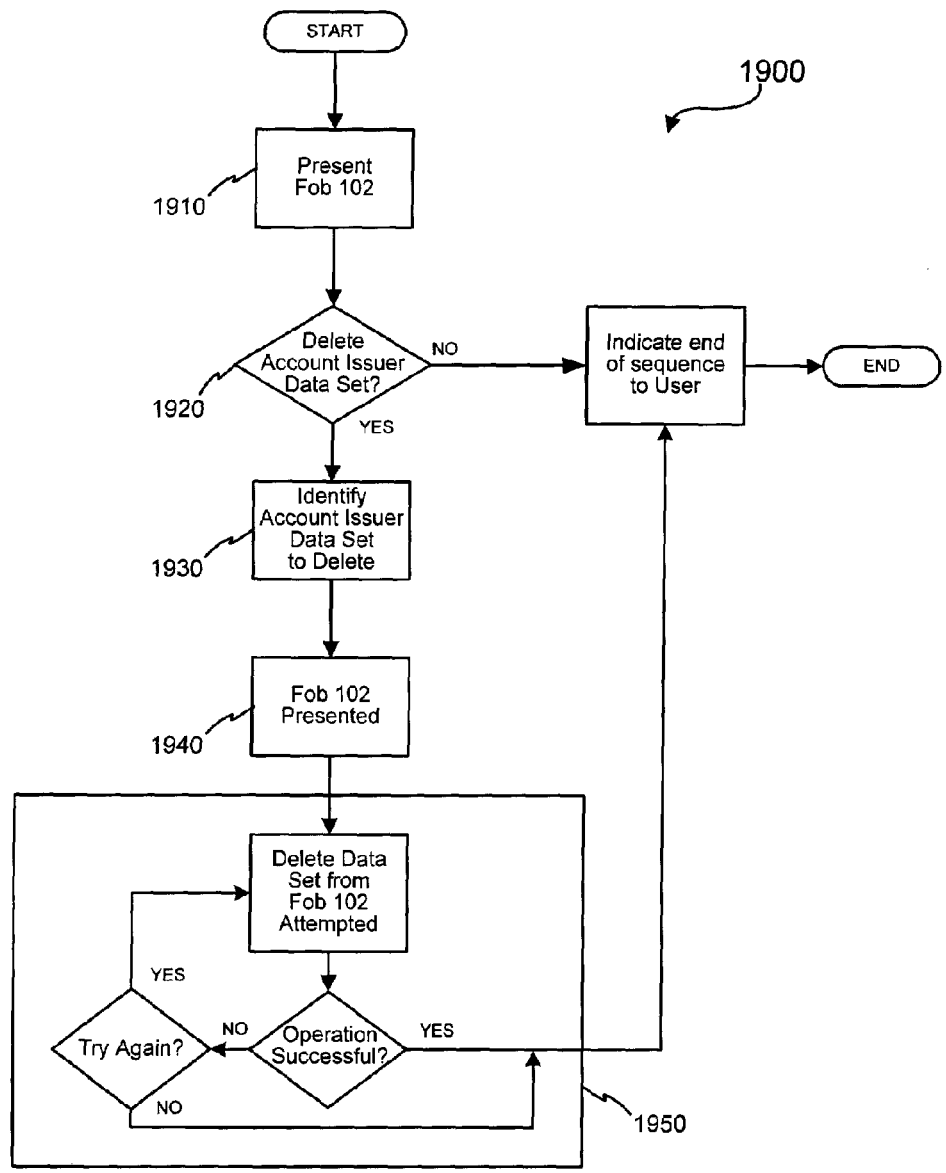
FIG. 19 illustrates an exemplary data set management method for deleting data sets in accordance with an exemplary embodiment of the present invention.

Furthermore, data sets may be deleted using any suitable techniques. For example, FIG. 19 illustrates an exemplary data set deletion method 1900. User 1101 presents fob 102 at a point-of-interaction 110, self-service location, or the like (step 1910). POI 110 may be configured to facilitate user 1101 providing input regarding deletion of a data set (step 1920). For example, POI 110 may ask user 1101, via a test screen, whether user 1101 desires to manage the data sets on fob 102. Through a series of menus and/or questions, user 1101 may identify data sets that user 1101 desires to delete.

Furthermore, POI 110 may be configured to interrogate database 214 or specific healthcare issuer systems 1130 to determine whether the deletion of a data set has been requested earlier. If user 1101 requests deletion of one or more data sets, the data sets are then identified (step 1930). It will be noted that step 1930 may occur concurrently with step 1920 or user 1101 may request deletion of a specific account at this step. In other embodiments, accounts may be deleted per predefined rules or policies, and/or the like. Upon presenting fob 102 again, the identified data set(s) are removed from fob 102 (steps 1940 and 1950). Other methods of deleting data sets may also be used to manage data sets on fob 102.

In an exemplary embodiment, management of the data sets may further include selecting preferences for use of the data sets. For example, user 1101 may indicate a desire to use data set A, associated with a primary insurance carrier, as a first option, but to use data set B, associated with a secondary insurance carrier when data set A is not available. In another example, one data set may be used for hospital transactions while another data set may be used for private physician transactions. User's 1101 data set preferences may be stored on fob 102 as a data set. In this example, when fob 102 is presented, all available data sets are read and RFID reader 104 determines which data sets are to be used based in part on the preferences stored on fob 102, which preferences may be updated from time to time.

In another embodiment, fob 102 may be configured to comprise two or more antennae that are both configured to send and receive information and fob 102 may be responsive to different RF frequencies. In this exemplary embodiment, each antenna may be configured to communicate using a particular protocol and/or frequency. Thus, fob 102 may be configured to communicate with two or more RFID readers 104 that each communicate with fob 102 using different transmission frequencies. For more information on dual antenna fobs, see U.S. patent application Ser. No. 10/192,488, filed Jul. 9, 2002, by inventors Michael J. Berardi, et al., and entitled "SYSTEM AND METHOD FOR PAYMENT USING RADIO FREQUENCY IDENTIFICATION IN CONTACT AND CONTACTLESS TRANSACTIONS" and its progeny, which are hereby incorporated by reference.

Figure 20:
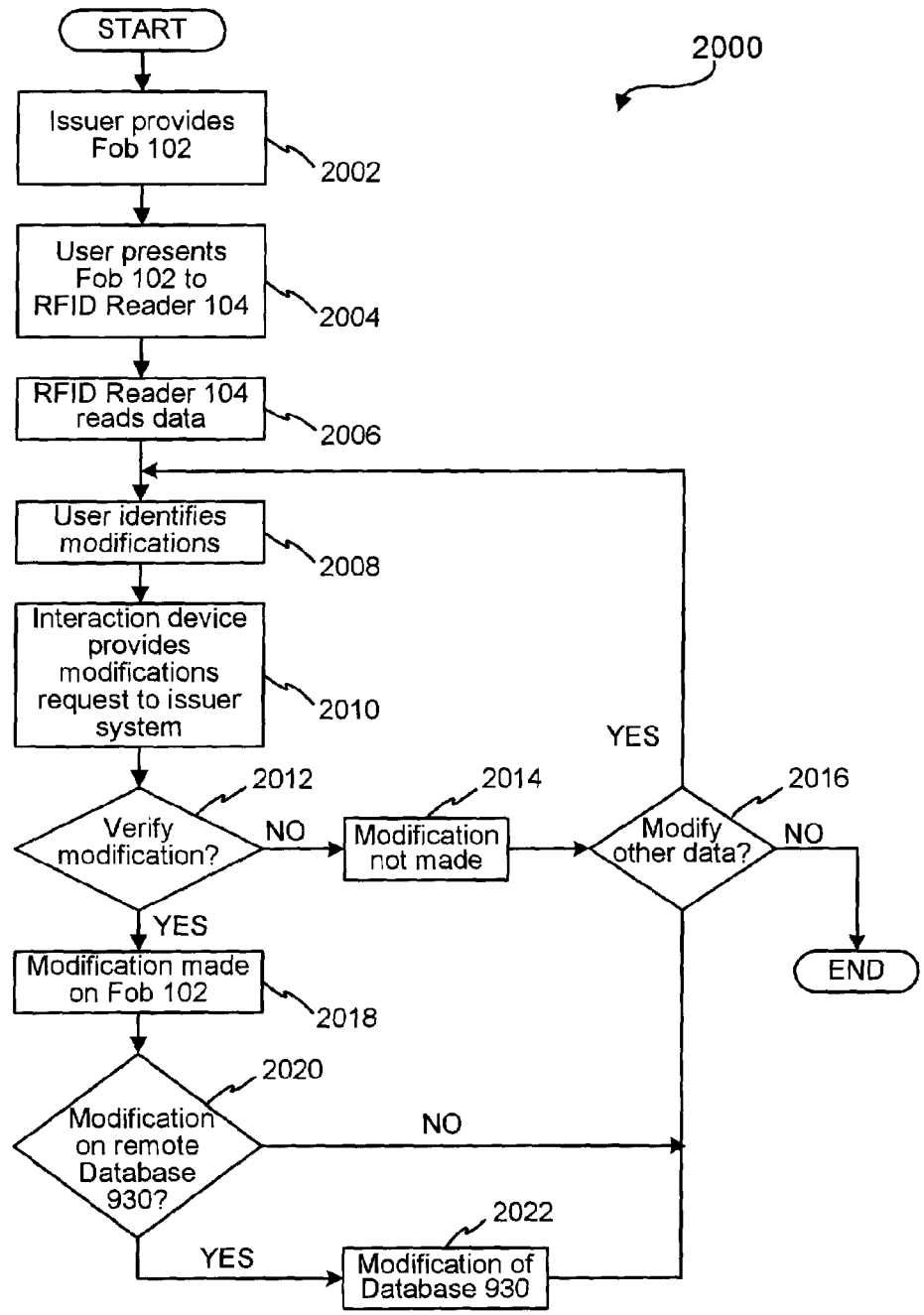
FIG. 20 illustrates an exemplary method for user self-management of data sets in accordance with an exemplary embodiment of the present invention.
Figure 21:
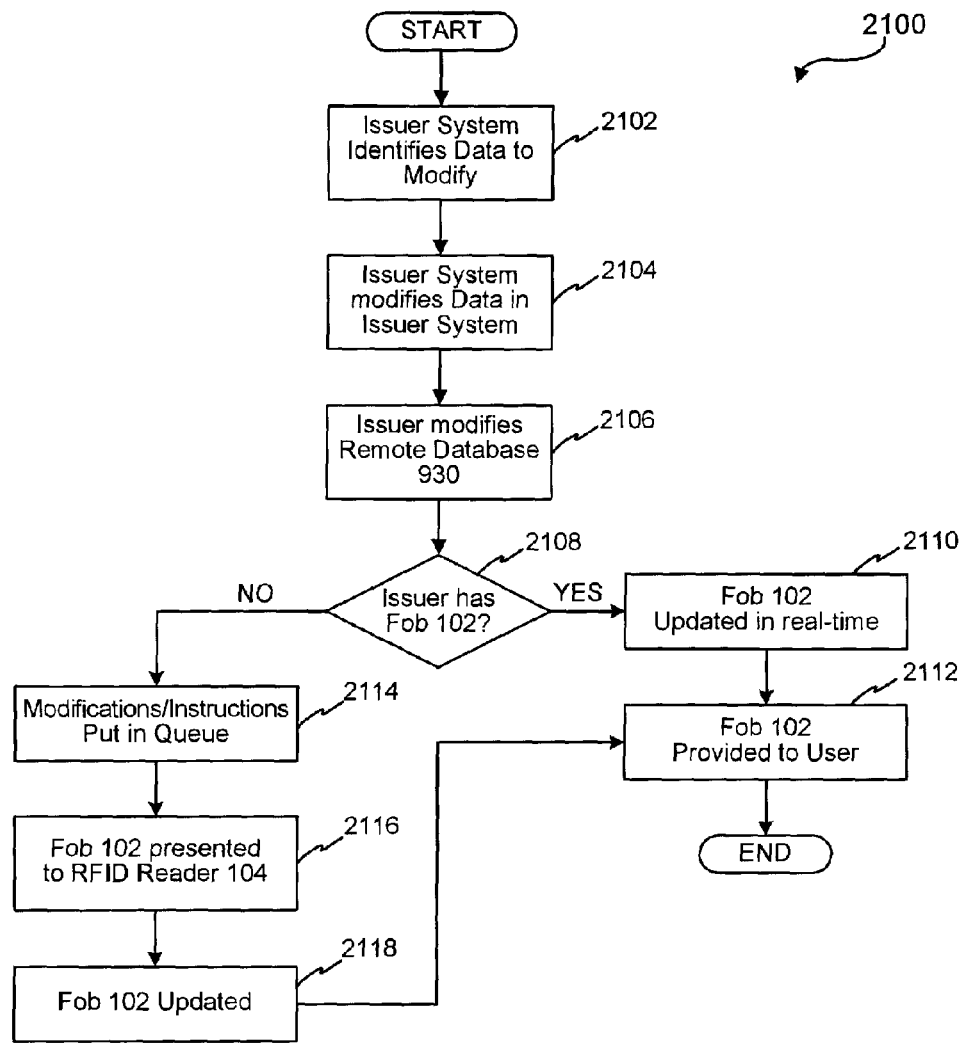
FIG. 21 illustrates an exemplary method for issuer management of data sets in accordance with the present invention.

As noted, the data associated with fob 102 may be modified by user 1101 and/or by healthcare issuer system 1130. FIGS. 20 and 21 respectively, depict exemplary methods for user 1101 and healthcare issuer system 1130 data management. For example, with respect to user 1101 self-management, healthcare issuer system 1130 may provide user 1101 with fob 102 (step 2002). Fob 102 may be provided with pre-stored issuer-owned data, or fob 102 may be configured to permit user 1101 to add the data at a later date. User 1101 may the present fob 102 to RFID reader 104 for initiating the self-management process (step 2004). RFID reader 104 may then read the data on fob 102, and provide the data to interaction device 1190 and/or POI 110 for displaying to user 1101 (step 2006). Alternatively, interaction device 1190 and/or POI 110 may provide user 1101 a list of available data to be added to fob 102.

User 1101 may then be permitted to identify which data user 1101 wishes to modify (step 2008). Identification of the data may include providing the data with a trailer or header indicating the action to be taken (e.g., add, delete, augment, overwrite, etc.). The header and an indicator of the data to be modified may then be provided to healthcare issuer system 1130 (step 2010) for verification as to whether such desired modifications are available to user 1101 (step 2012). If the desired modifications are not available, the modifications will not be made and user 1101 is notified accordingly (step 2014). User 1101 may then be permitted to identify whether other data is to be modified (step 2016). If so (step 2008), interaction device 1190 and/or POI 110 may provide a request for modification to healthcare issuer system 1130 (step 2010) and the verification process is repeated.

Alternatively, where healthcare issuer system 1130 verifies that the modifications may be made (step 2012), interaction device 1190 and/or POI 110 may make the modifications to the appropriate data on fob 102 (step 2018). Additionally, where the system 1100 includes a remote database 930 for storing a mirror image of the data contained on fob 102 (step 2020), interaction device 1190, POI 110 and/or healthcare issuer system 1130, may facilitate modification of remote database 930 (step 2022). User 1101 may then be permitted to select other data sets to modify (step 2016), in similar manner as was described above.

In either case, where the modifications are complete, user 1101 may then present fob 102 to a healthcare provider for use in completing a transaction.

FIG. 21 depicts an exemplary method 2100 wherein healthcare issuer system 1130 manages the data contained on fob 102. For example, the issuer may identify on healthcare issuer system 1130 which data sets are to be modified (step 2102). The modifications may then be made to the corresponding data set stored on healthcare issuer system 1130 (step 2104). Where system 1100 includes remote database 930, healthcare issuer system 1130 may provide the modifications/instructions to database 214 for updating database 930 accordingly (step 2106).

In addition, healthcare issuer system 1130 may query as to whether healthcare issuer system 1130 is in possession of fob 102 for executing the modifications to the data set on fob 102 in real-time or substantially real-time (step 2108). If so, the modifications are made accordingly (step 2110) and fob 102 may then be provided to user 1101 for use in completing a healthcare transaction using the distinct data sets modified (step 2112).

Where healthcare issuer system 1130 is not in possession of fob 102 at the time the healthcare issuer determines that modifications to the data on fob 102 are to be made (step 2108), the modifications may be made on healthcare issuer system 1130 (step 2104), and may be placed in queue, for uploading to fob 102 when it is next presented to healthcare issuer system 1130 or to the appropriate RFID reader 104 (step 2114). When fob 102 is presented thusly (step 2116), healthcare issuer system 1130 may be notified that fob 102 is available for modifying, and healthcare issuer system 1130 may then provide the instructions for modification (e.g., modified data including headers) to the appropriate RFID reader 104 for modifying fob 102 (step 2118). Fob 102 may then be provided to user 1101 for use in completing a transaction (step 2112).

Figure 22:
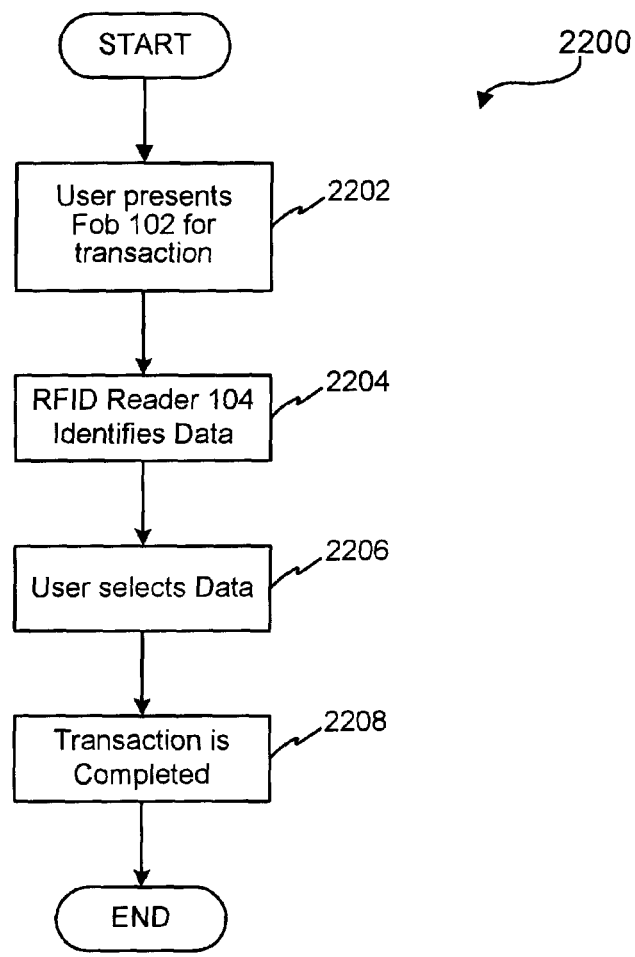
FIG. 22 illustrates an exemplary data set selection method for use in completing a transaction.

As noted, fob 102 may include multiple data sets which correspond to distinct healthcare issuer systems 1130, and which may be used to complete a healthcare transaction. User 1101 may be permitted to choose which data set to use for healthcare transaction completion. FIG. 22 illustrates an exemplary method 2200 by which user 1101 may choose which of the data sets to use to complete a healthcare transaction. For example, user 1101 may present fob 102 to healthcare system 1120 for use in completing a healthcare transaction (step 2202). Healthcare system 1120 may then read the data stored on fob 102 and report to user 1101 all distinct data sets which may be used to complete a healthcare transaction (2204). User 1101 may then select the appropriate data set (step 2206) and the healthcare transaction is completed accordingly (step 2208).

It should be noted that completion of a healthcare transaction may be performed under any business as usual standard employed by the healthcare provider and/or healthcare issuer system 1130. For example, the healthcare provider server 1122 may be configured to communicate transaction data to the appropriate healthcare issuer system 1130, in real-time or substantially real-time, or by using batch processing at the end of each day. Any suitable means for delivering the transaction data to the healthcare issuer systems 1130 may be used. In one exemplary embodiment of the present invention, the transaction data may be delivered to healthcare issuer system 1130 via network 136. Healthcare issuer system 1130 may receive the transaction information and process the transaction under issuer defined protocol independent of any other protocol used by other issuers to process a transaction. Healthcare issuer system 1130 may receive the transaction data and provide the healthcare provider with the appropriate satisfaction for the transaction.

In another exemplary embodiment of the present invention, system 100A may be configured with one or more biometric scanners, processors and/or systems. A biometric system may include one or more technologies, or any portion thereof, such as, for example, recognition of a biometric. As used herein, a biometric may include a user's voice, fingerprint, facial, ear, signature, vascular patterns, DNA sampling, hand geometry, sound, olfactory, keystroke/typing, iris, retinal or any other biometric relating to recognition based upon any body part, function, system, attribute and/or other characteristic, or any portion thereof. Certain of these technologies will be described in greater detail herein. Moreover, while some of the examples discussed herein may include a particular biometric system or sample, the invention contemplates any of the biometrics discussed herein in any of the embodiments.

The biometric system may be configured as a security system and may include a registration procedure in which a user of transaction instrument (e.g., fob 102) proffers a sample of his fingerprints, DNA, retinal scan, voice, and/or other biometric sample to an authorized sample receiver (ASR). An ASR may include a local database, a remote database, a portable storage device, a host system, an issuer system, a healthcare provider system, a fob issuer system, a healthcare system, an employer, a financial institution, a non-financial institution, a loyalty point provider, a company, the military, the government, a school, a travel entity, a transportation authority, a security company, and/or any other system or entity that is authorized to receive and store biometric samples and associate the samples with specific biometric databases and/or transaction instruments (e.g., fobs 102). As used herein, a user of a fob, fob user, or any similar phrase may include the person or device holding or in possession of the fob, or it may include any person or device that accompanies or authorizes the fob owner to use the fob.

Figure 14:
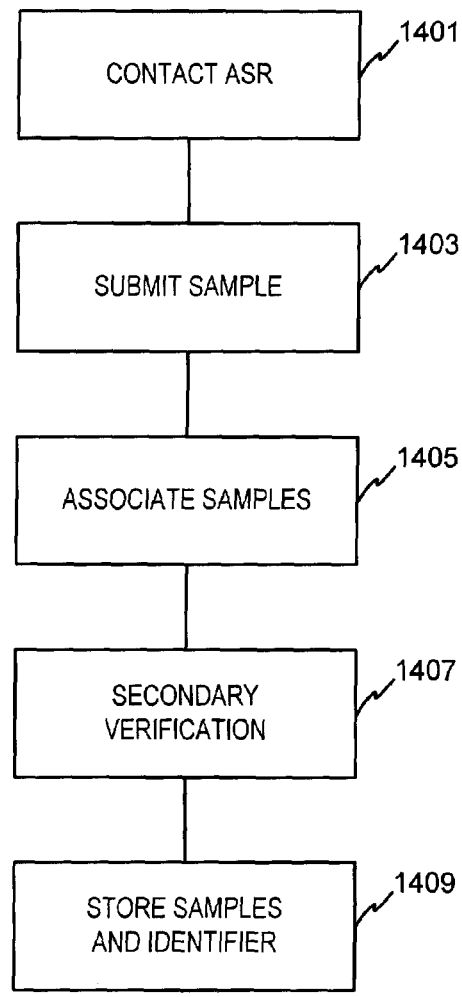
FIG. 14 is a depiction of an exemplary biometrics process in accordance with the present invention.

FIG. 14 illustrates an exemplary registration procedure in accordance with the present invention. In one embodiment, a fob user may contact an ASR to submit one or more biometric samples to an ASR (step 1401). The fob user may contact the ASR and submit a sample in person, through a computer and/or Internet, through software and/or hardware, through a third-party biometric authorization entity, through a kiosk and/or biometric registration terminal, and/or by any other direct or indirect means, communication device or interface for a person to contact an ASR.

A fob user may then proffer a biometric sample to the ASR (step 1403). As used herein, a biometric sample may be any one or more of the biometric samples or technologies, or portion thereof, described herein or known in the art. By proffering one or more biometric samples, a biometric may be scanned by at least one of a retinal scan, iris scan, fingerprint scan, hand print scan, hand geometry scan, voice print scan, vascular scan, facial and/or ear scan, signature scan, keystroke scan, olfactory scan, auditory emissions scan, DNA scan, and/or any other type of scan to obtain a biometric sample. Upon scanning the sample, the system may submit the scanned sample to the ASR in portions during the scan, upon completing the scan or in batch mode after a certain time period. The scanned sample may include a hardcopy (e.g., photograph), digital representation, an analog version or any other configuration for transmitting the sample. The ASR receives the sample and the ASR may also receive copies of a fob user's biometric data along with the sample or at a different time (or within a different data packet) from receiving the sample.

The ASR and/or fob user 102 may store the sample in digital and/or any storage medium known in the art and correlate and/or register the sample with fob user information. By storing the sample in digital format, the ASR may digitize any information contained in one of the biometric scans described herein. By storing the sample in any storage medium, the ASR may print and/or store any biometric sample. Hardcopy storage may be desirable for back-up and archival purposes. As used herein, registered samples may include samples that have been proffered, stored and associated with user information.

The biometric sample may also be associated with user information (step 1405). The sample may be associated with user information at any step in the process such as, for example, prior to submission, during submission and/or after submission. In one embodiment, the user may input a PIN number or zip code into the POI terminal, then scan the biometric to create the biometric sample. The local POI system may associate the biometric sample data with the PIN and zip code, then transmit the entire packet of information to the ASR. In another embodiment, the POI may facilitate transmitting the sample to an ASR, and during the transmission, the sample may be transmitted through a third system which adds personal information to the sample.

The information associated with the biometric sample may include any information such as, for example, fob user information, fob 102 information, fob 102 identifier information, fob 102 vender information, fob 102 operability information, and/or fob 102 manufacturing information. Fob 102 information is not limited to transponder information and may include information related to any healthcare information and/or any transaction instrument such as smart cards, credit cards, debit cards, healthcare provider-specific cards, loyalty point cards, cash accounts and any other transaction instruments and/or accounts. The fob user information may also contain information about the user including personal information—such as name, address, and contact details; financial information—such as one or more financial accounts associated with the fob user; loyalty point information—such as one or more loyalty point accounts (e.g., airline miles, charge card loyalty points, frequent diner points) associated with the fob user; and/or non-financial information—such as employee information, employer information, medical information, family information, and/or other information that may be used in accordance with a fob user.

For example, fob user may have previously associated a medical insurance account and a dental insurance account with his biometric sample which is stored at an ASR. Later, when fob user desires to access healthcare information stored on the fob, fob user may submit his biometric sample while using fob 102 for accessing information at the POI. The POI may facilitate sending the biometric sample to the ASR such that the ASR authorizes the biometric sample and checks a look-up table in the ASR database to determine if any information is associated with the sample. If information (e.g., insurance accounts) is associated with the sample, the ASR may transmit the information to the POI terminal. The POI terminal may then present fob user with a list of the two accounts associated with the biometric sample. Fob user and/or a healthcare administrator may then chose one of the accounts in order to continue and finalize the information transaction.

In another embodiment, fob user may associate each account and/or type of information with a different biometric sample. For example, during registration, fob user may submit a sample of his right index fingerprint, and request that the system primarily associate this sample with a particular credit card and/or account. Fob user may additionally submit a sample of his left index fingerprint and request that the system primarily associate the sample with a particular medical insurance account. Additionally, fob user may submit his right thumbprint and request that the system primarily associate that sample with a particular dental insurance account. By "primarily" associating a sample with an account, the system initially associates the sample with that account. For example, fob user submitting his right index fingerprint for a financial transaction may have money for a healthcare transaction taken from his credit card account. Fob user may additionally specify which accounts should be secondarily associated with a sample. For example, fob user may have a medical insurance account secondarily associated with his right index fingerprint. As a result, if fob user submits his right index fingerprint for a transaction, and the primary account associated with the sample may be used to pay the account, while the secondary account may be accessed in order to provide further information for the transaction.

While primary and secondary account association is described herein, any number of accounts may be associated with a sample. Moreover, any hierarchy or rules may be implemented with respect to the association. For example, the fob user may instruct the system to access a medical insurance account when it receives a right index fingerprint sample, the transaction involves the use of a debit card and the transaction involves paying a co-pay amount. While fingerprint samples are discussed herein, any biometric sample may have one or more accounts associated with it and may be used to facilitate a transaction using any of the routines discussed herein.

The ASR and/or fob user may associate a specific fob 102 identifier with the biometric sample by any method known in the art for associating an identifier (e.g., through the use of software, hardware and/or manual entry.) The ASR may additionally verify the fob user and/or fob 102 by using one or more forms of the user's secondary identification (step 1407). For example, the ASR may verify the fob user by matching the fob information to information retrieved from scanning information from a fob user's driver's license, medical insurance card, and/or other form of secondary identification. The ASR may verify fob 102 by contacting the vendor of fob 102 to confirm that fob 102 was issued to a specific fob user. In another embodiment, the ASR may activate fob 102 during the registration procedure to confirm that fob 102 transponder identifier and other information is properly associated with the fob user and the fob user's specific biometric samples. The ASR may additionally employ one or more verification methods to confirm that the biometric sample belongs to the user, such as, for example, the ASR may request from the user demographic information, further biometric samples and/or any other information. As used herein, "confirm", "confirmation" or any similar term includes verifying or substantially verifying the accuracy, existence, non-existence, corroboration, and/or the like of the information, component, or any portion thereof. The ASR may additionally employ one or more additional processing methods in order to facilitate association of a biometric sample. As used herein, the term processing may include scanning, detecting, associating, digitizing, printing, comparing, storing, encrypting, decrypting, and/or verifying a biometric and/or a biometric sample, or any portion thereof.

Upon association, authentication and/or verification of the biometric sample and fob 102, the system may store the sample and fob 102 identifier (step 1409) in one or more databases on and/or in communication with system 100 via a network, server, computer, or any other means of communicating as described herein. The database(s) may be any type of database described herein. For example, a biometric sample stored on fob 102 may be stored in database 212 and/or on databases found in engine 130. The database(s) may be located at or operated by any of the entities discussed herein such as, for example, the ASR and/or by a third-party biometric database operator.

The information stored in the database may be sorted or stored according to one or more characteristics associated with the sample in order to facilitate faster access to the stored sample. For example, fingerprint samples may be stored in a separate database than voice prints. As another example, all fingerprints with certain whirl patterns may be stored in a separate sub-database and/or database from fingerprints with arch patterns.

The biometric samples may also be stored and/or associated with a personal identification number (PIN) and/or other identifier to facilitate access to the sample. The PIN may be fob user selected or randomly assigned to the biometric sample. The PIN may consist of any characters such as, for example, alphanumeric characters and/or foreign language characters.

The system may further protect the samples by providing additional security with the sample. The security may include, for example, encryption, decryption, security keys, digital certificates, firewalls and/or any other security methods known in the art and discussed herein. One or more security vendors may utilize the security methods to store and/or access the biometric samples. The present invention anticipates that storage of the biometric samples may be such that a sample is first encrypted and/or stored under a security procedure, such that the sample may only be accessed by a vendor with the proper level of access or security which corresponds to or provides access to the stored sample. The samples may be accessible by certain vendors such as, for example, fob 102 transaction account provider system, a healthcare system, an issuer system, a healthcare provider system, a fob issuer system, an employer, a financial institution, a non-financial institution, a loyalty-point provider, a company, the military, the government, a school, a travel entity, a transportation authority, and/or a security company.

Figure 15:
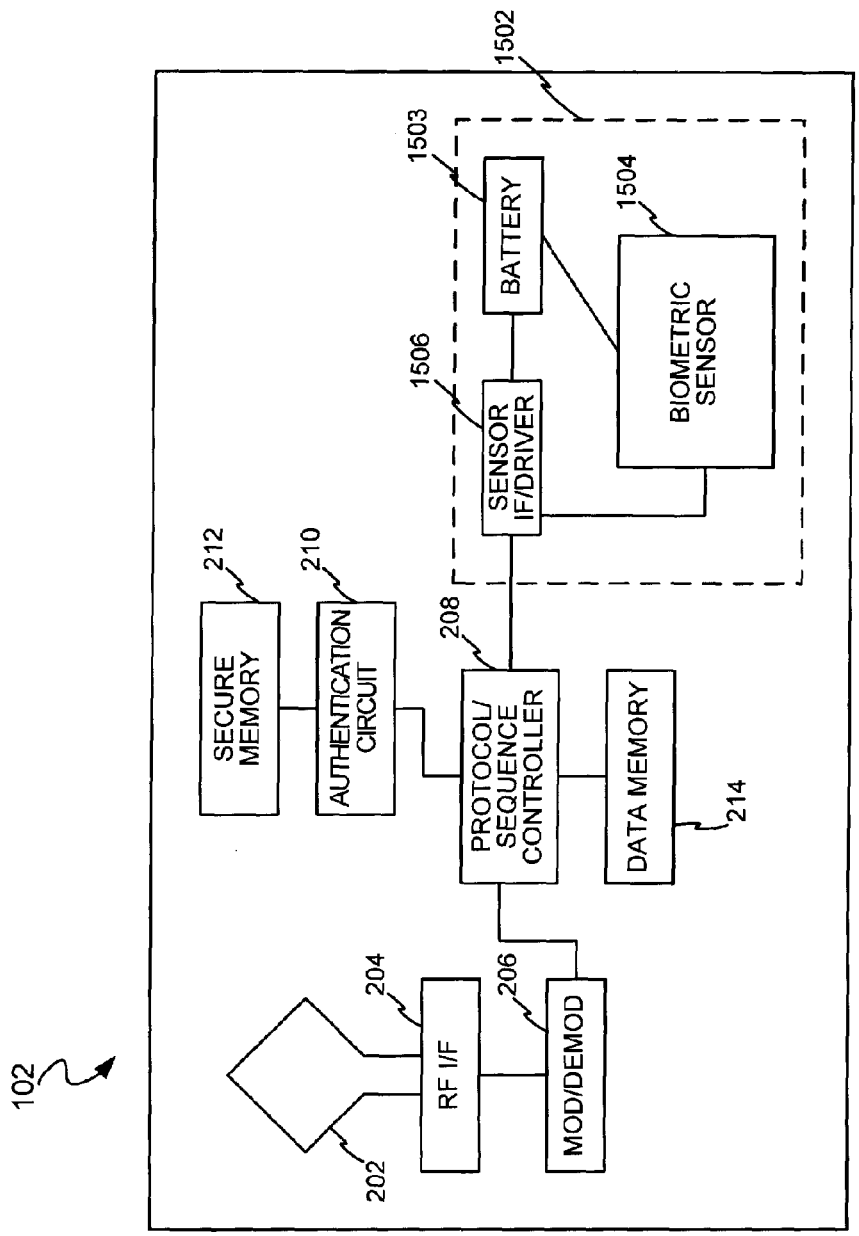
FIG. 15 is another schematic illustration of an exemplary fob in accordance with the present invention.
Figure 16:
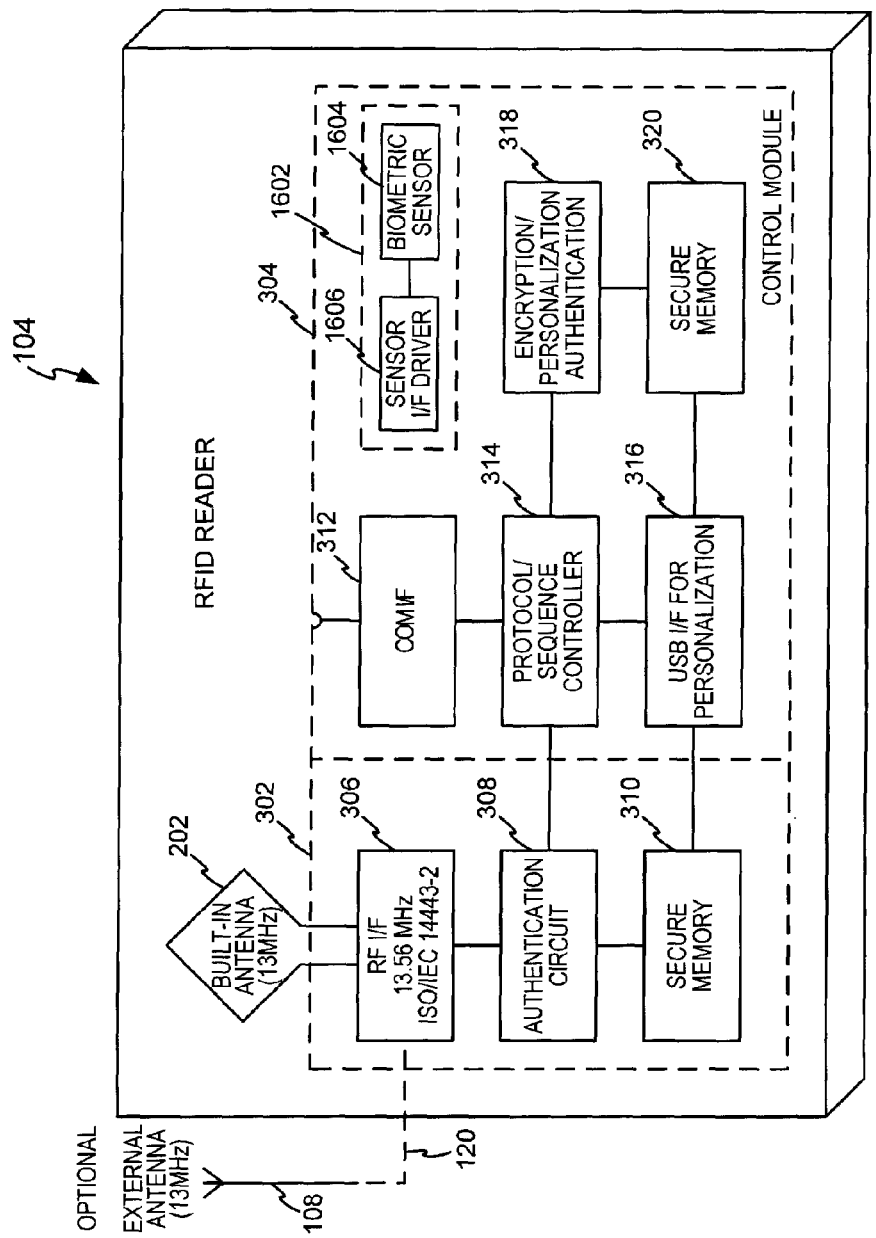
FIG. 16 another schematic illustration of an exemplary fob in accordance with the present invention.

The fob of the invention may include a particular security system wherein the security system incorporates a particular biometric system. As shown in FIG. 15, fob 102 includes a biometric security system 1502 configured for facilitating biometric security using, for example, fingerprint samples. Alternatively, as shown in FIG. 16, RFID reader 104 includes a biometric security system 1602 configured for facilitating biometric security using biometric samples. As used herein, fingerprint samples may include samples of one or more fingerprints, thumbprints, palmprints, footprints, and/or any portion thereof. Biometric security system 1502, 1602 may include a biometric sensor 1504, 1604 which may be configured with a sensor and/or other hardware and/or software for acquiring and/or processing the biometric data from the person such as, for example, optical scanning, capacitance scanning, or otherwise sensing the portion of fob user. In one embodiment, biometric sensor 1504, 1604 of the security system 1502, 1602 may scan a finger of a fob user in order to acquire his fingerprint characteristics into fob 102. Biometric sensor 1504, 1604 may be in communication with a sensor interface/driver 1506, 1606 such that sensor interface 1506, 1606 receives the fingerprint information and transmits a signal to controller 208, 308 to facilitate activating the operation of fob 102. A power source (e.g., battery 1503) may be in communication with biometric sensor 1504, 1604 and sensor interface 1506, 1606 to provide the desired power for operation of the biometric security system components.

In one exemplary application of fob 102 incorporating biometric security system 1502, the user may place his finger on the biometric sensor to initiate the mutual authentication process between fob 102 and RFID reader 104, and/or to provide verification of the user's identity. Fob 102 may digitize the fingerprint and compare it against a digitized fingerprint stored in a database (e.g., security database 212) included on fob 102. The fingerprint information may additionally be compared with information from one or more third-party databases communicating with fob 102 through any communication software and/or hardware, including for example, RFID reader 104, a USB connection, a wireless connection, a computer, a network and/or any other means for communicating. This transfer of information may include use of encryption, decryption, security keys, digital certificates and/or other security devices to confirm the security of the sample. Fob 102 may additionally communicate with third-party databases to facilitate a comparison between fob 102 identifier and other fob identifiers stored with the biometric samples. As used herein, "compare," "comparison" and similar terms may include determining similarities, differences, existence of elements, non-existence of elements and/or the like.

Protocol/sequence controller 208 may facilitate the local comparison to authenticate the biometric and authentication circuit 210 may validate the information. Any of the embodiments may alternatively or additionally include remote comparisons performed or controlled by one or more third-party security vendors. One or more comparison techniques and/or technologies may be used for comparisons. For example, for fingerprint comparisons, protocol/sequence controller 208 may utilize an existing database to compare fingerprint minutia such as, for example, ridge endings, bifurcation, lakes or enclosures, short ridges, dots, spurs and crossovers, pore size and location, Henry System categories such as loops, whorls, and arches, and/or any other method known in the art for fingerprint comparisons.

Fob 102 may additionally be configured with secondary security procedures to confirm that fake biometric samples are not being used. For example, to detect the use of fake fingers, fob 102 may be further configured to measure blood flow, to check for correctly aligned ridges at the edges of the fingers, and/or any other secondary procedure to reduce biometric security fraud. Other security procedures for ensuring the authenticity of biometric samples may include monitoring pupil dilation for retinal and/or iris scans, pressure sensors, blinking sensors, human motion sensors, body heat sensors and/or any other procedures known in the art for authenticating the authenticity of biometric samples.

After verifying the biometric information, fob 102 and RFID reader 104 may begin mutual authentication, and the information and/or financial transaction may proceed accordingly. However, the invention contemplates that the verification of biometric information may occur at any point in the transaction such as, for example, after the mutual authentication. At any point in the transaction, the system may additionally request fob user to enter a PIN and/or other identifier associated with the transaction account and/or biometric sample to provide further verification of fob user's identification. As part of the transaction, fob user payor may be requested to select from one of the insurance accounts, healthcare accounts, financial accounts, loyalty accounts, credit accounts, debit account, and/or other accounts associated with the biometric sample. The user may be presented with a list of account options on a display associated with RFID reader 104, fob 102, a third-party security device and/or any other financial or transaction device association with a transaction. In another embodiment, a payee may select one of the accounts. For example, a hospital payee may manually and/or automatically select a specific medical insurance account, if available, for a transaction.

RFID reader 104 may also be configured with secondary security procedures biometric to confirm that fake biometric samples are not being used. For example, RFID reader 104 may be further configured to measure blood flow, body heat and/or any other secondary procedure to reduce biometric security fraud. Other security procedures for ensuring the authenticity of biometric samples may include monitoring pupil dilation for retinal and/or iris scans, pressure sensors, blinking sensors, human motion sensors, and/or any other procedures known in the art for authenticating the authenticity of biometric samples. After verifying the biometric information, fob 102 and RFID reader 104 may begin mutual authentication, and the transaction may proceed accordingly.

While the biometric safeguard mechanisms describe fob 102 and/or RFID reader 104 configured with a biometric safeguard mechanism, any part of system 100 may be equipped with a biometric safeguard system. For example, the invention contemplates receiving a biometric sample only at the reader, only at the fob, at both the fob and the reader, or at any other combination of location or device. As such, any scanner or database discussed herein may be located within or associated with another device. For example, the fob may scan a user biometric, but the database used for comparison may be located within the reader or healthcare server. In other embodiments, the biometric security device may be located away from the point-of-interaction device and/or provide other functions. In one embodiment, the biometric security device may be located outside of an emergency room intake area to allow a user to not only start the authentication process before check-in, but also to allow expedited insurance authentication of a patient for medical procedures. In this regard, the biometric security device may communicate the information to the point-of-interaction device so the POI may verify that the person that checked into the hospital is the same person that is now receiving medical attention. In another embodiment, any portion of system 100 may be configured with a biometric security device. The biometric security device may be attached and/or free-standing. Biometric security devices may be configured for local and/or third-party operation. For example, the present invention contemplates the use of third-party fingerprint scanning and security devices such as those made by Interlink Electronics, Keytronic, Identix Biotouch, BIOmetricID, onClick, and/or other third-party vendors.

In yet another embodiment, the database used for comparison may contain terrorist and/or criminal information. As used herein, terrorists and/or criminals may include terrorists, felons, criminals, convicts, indicted persons, insurgents, revolutionaries and/or other offenders. The information may include biometric information, personal information as described herein, arrest records, aliases used, country of residence, affiliations with gangs and terrorist groups, and/or any other terrorist and/or criminal information.

As an example of a secondary security procedure in accordance with the present invention, the biometric sensor 1504, 1604 and/or RFID reader 104 may be configured to allow a finite number of scans. For example, biometric sensor 1504, 1604 may be configured to only accept data from a single scan. As a result, biometric sensor 1504, 1604 may turn off or deactivate fob 102 and/or RFID reader 104 if more than one scan is needed to obtain a biometric sample. Biometric sensor 1504, 1604 may also be configured to accept a preset limit of scans. For example, biometric sensor 1504, 1604 may receive three invalid biometric samples before it turns off and/or deactivates fob 102 and/or RFID reader 104.

The sensor or any other part of system 100 may also activate upon sensing a particular type or group of biometric samples. The activation may include sending a signal, blinking, audible sound, visual display and/or the like. For example, if the sensor detects information from a specific insurance holder, the system may display a special information on the POI terminal. In another embodiment, the system may send a signal to a primary account holder or any other person or device to notify them that the fob is being used or that a condition or rule is being violated (e.g., certain user information is being accessed).

Any of the biometric security systems described herein may additionally be configured with a fraud protection log. That is, a biometric security system, such as biometric security system 1502, 1602 may be configured to log all biometric samples submitted on fob 102 and/or RFID reader 104 and store the log information on databases on and/or communicating with system 1502, 1602. If a new and/or different biometric sample is submitted that differs from the log data, biometric security system 1502, 1602 may employ a security procedure such as deactivation, warning authorities, requesting a secondary scan, and/or any other security procedure.

Biometric security system 1502, 1602 and/or the biometric security system configured with system 100 may also be configured to obtain a plurality of biometric samples for verification and/or other security purposes. For example, after biometric security system 1502, receives a first biometric sample (e.g., scans one finger), it may be configured to receive a second biometric sample (e.g., scans a second finger). The first and second biometric samples may be compared with stored biometric samples by any of the methods disclosed herein. The second biometric sample may be the only sample compared with stored biometric samples if the first sample is unreadable or inadequate.

While the biometric safeguard mechanisms described herein use fingerprint scanning and retinal scanning for biometric sample verification for exemplification, any biometric sample may be submitted for verification, authorization and/or any other safeguard purpose. For example the present invention contemplates the use of voice recognition, facial and/or ear recognition, signature recognition, vascular patterns, DNA sampling, hand geometry, auditory emissions recognition, olfactory recognition, keystroke/typing recognition, iris scans, and/or any other biometric known in the art.

In yet another exemplary application of the present invention, fob 102 may be configured for use with global positioning technologies. For example, fob 102 may include any combination of positioning technology such as global position system (GPS), wireless assisted GPS, wireless assisted protocol (WAP) based location, geography markoff language (GML) based location, differential GPS, enhanced observed time difference (E-OTD), enhanced cell identification, and uplink time difference of arrival (U-TDOA) technologies. Fob 102 may be configured to communicate its positional information to one or more servers on network 136 and/or engine 130 to provide information based on the location of fob 102. For example, a user may be use a GPS-enabled fob 102 to determine the nearest location of a healthcare provider.

The preceding detailed description of exemplary embodiments of the invention makes reference to the accompanying drawings, which show the exemplary embodiment by way of illustration. While these exemplary embodiments are described in sufficient detail to enable those skilled in the art to practice the invention, it should be understood that other embodiments may be realized and that logical and mechanical changes may be made without departing from the spirit and scope of the invention. For example, the steps recited in any of the method or process claims may be executed in any order and are not limited to the order presented. Further, the present invention may be practiced using one or more servers, as necessary. Thus, the preceding detailed description is presented for purposes of illustration only and not of limitation, and the scope of the invention is defined by the preceding description, and with respect to the attached claims.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as critical, required, or essential features or elements of any or all the claims. As used herein, the terms "comprises," "comprising," or any other variations thereof, are intended to cover a non-exclusive inclusion, such that a process, method, article, or apparatus that comprises a list of elements does not include only those elements but may include other elements not expressly listed or inherent to such process, method, article, or apparatus. Further, no element described herein is required for the practice of the invention unless expressly described as "essential" or "critical."

What is claimed is:

1. A method comprising:
receiving, at a Radio Frequency (RF) reader, a transaction request from an RF Transaction device configured to store a first data set associated with a first data set owner in a first data storage area on the RF transaction device;
searching the RF transaction device to determine if at least one of the first data set or a second data set is available for use in connection with the transaction request;
receiving an add request from the RF transaction device to add the second data set to the RF transaction device in response to the second data set not being available for use;
allocating a second data storage area on the RF transaction device in response to the add request from the RF transaction device and in response to an issuer system indicating that the first data set is available for addition to the RF transaction device;
receiving, at the RF reader, the second data set from a point of interaction terminal of the merchant system, wherein the second data set is inputted into the point of interaction terminal by a transaction device distinct from the RF transaction device;
adding, by the RF reader, the second data set to the RF transaction device in the second data storage area, wherein the second data storage area is reserved for use by a second data set owner distinct from the first data set owner; and
processing the transaction request in response to the adding the second data set.

2. The method of claim 1, further comprising displaying a message on a user interface of the RF Identification (RFID) reader in response to the second data set not being available.

3. The method of claim 1, further comprising storing a first transaction device account code in the first data storage area, and storing a second transaction device account code in the second data storage area.

4. The method of claim 2, further comprising receiving the add request in response to the displaying the message on the RFID reader user interface.

5. The method of claim 1, wherein at least one of the first data set or the second data set includes healthcare information to facilitate a healthcare transaction.

6. The method of claim 1, further comprising enrolling the first data set owner and the second data set owner in multiple transaction accounts on the RF transaction device.

7. The method of claim 1, wherein the processing the transaction request comprises processing the transaction request with a first account identifier stored in the first data set.

8. The method of claim 1, wherein the processing the transaction request comprises processing the transaction request with a second account identifier stored in the second data set.

9. The method of claim 5, wherein the healthcare information includes at least one of personal information, medical history, medical information, insurance information, and financial information.

10. The method of claim 1, wherein the first data set includes multiple healthcare transaction accounts associated with a single healthcare account identifier.

11. The method of claim 1, further comprising receiving the second data set from the issuer system.

12. A non-transitory memory element having stored thereon a plurality of instructions for execution by a processor, the plurality of instructions comprising:
instructions to receive, at a Radio Frequency identification (RFID) reader, a transaction request from an RF transaction device configured to store a first data set associated with a first data set owner in a first data storage area on the RF transaction device;
instructions to search the RF transaction device to determine if at least one of the first data set or a second data set is available for use in connection with the transaction request;
instructions to receive an add request from the RF transaction device to add the second data set to the RF transaction device in response to the second data set not being available for use;
instructions to allocate a second data storage area on the RF transaction device in response to the add request from the RF transaction device and in response to an issuer system indicating that the first data set is available for addition to the RF transaction device;
instructions to receive, at the RF reader, the second data set from a point of interaction terminal of the merchant system, wherein the second data set is inputted into the point of interaction terminal by a transaction device distinct from the RF transaction device;
instructions to add, by the RF reader, the second data set to the RF transaction device in the second data storage area, wherein the second data storage area is reserved for use by a second data set owner distinct from the first data set owner; and
instructions to process the transaction request in response to the instructions to add the second data set.

13. The method of claim 1, further comprising modifying the first data set without involving the second data set owner.

14. The method of claim 1, wherein the transaction device includes at least one of a credit card, a debit card, and an insurance card.

15. The method of claim 1, wherein the first data storage area is not accessible by the second data set owner, and wherein the second data storage area is not accessible by the first data set owner.

16. The method of claim 1, further comprising instructing a control device on the RF transaction device to allocate the second data storage area on the RF transaction device.

* * * * *